US010130701B2

(12) United States Patent
Bickerton et al.

(10) Patent No.: US 10,130,701 B2
(45) Date of Patent: Nov. 20, 2018

(54) CORONAVIRUS

(71) Applicant: THE PIRBRIGHT INSTITUTE, Pirbright, Woking (GB)

(72) Inventors: Erica Bickerton, Woking (GB); Sarah Keep, Woking (GB); Paul Britton, Woking (GB)

(73) Assignee: THE PIRBRIGHT INSTITUTE, Woking, Pirbright (GB)

( * ) Notice: Subject to any disclaimer, the term of this patent is extended or adjusted under 35 U.S.C. 154(b) by 0 days.

(21) Appl. No.: 15/328,179

(22) PCT Filed: Jul. 23, 2015

(86) PCT No.: PCT/GB2015/052124
§ 371 (c)(1),
(2) Date: Jan. 23, 2017

(87) PCT Pub. No.: WO2016/012793
PCT Pub. Date: Jan. 28, 2016

(65) Prior Publication Data
US 2017/0216427 A1 Aug. 3, 2017

(30) Foreign Application Priority Data
Jul. 23, 2014 (GB) .................................. 1413020.7

(51) Int. Cl.
| | |
|---|---|
| *A61K 39/215* | (2006.01) |
| *C12N 7/00* | (2006.01) |
| *C12N 9/12* | (2006.01) |
| *A61K 39/00* | (2006.01) |

(52) U.S. Cl.
CPC .............. *A61K 39/215* (2013.01); *C12N 7/00* (2013.01); *C12N 9/127* (2013.01); *C12Y 207/07048* (2013.01); *A61K 2039/5254* (2013.01); *A61K 2039/54* (2013.01); *C12N 2770/20021* (2013.01); *C12N 2770/20022* (2013.01); *C12N 2770/20034* (2013.01); *C12N 2770/20051* (2013.01); *C12N 2770/20062* (2013.01)

(58) Field of Classification Search
CPC .................................................... A61K 39/215
See application file for complete search history.

(56) References Cited

U.S. PATENT DOCUMENTS 7,452,542 B2 * 11/2008 Denison ............... C07K 14/005
424/221.1

FOREIGN PATENT DOCUMENTS

| WO | WO-2004/092360 A2 | 10/2004 |
|---|---|---|
| WO | WO-2005/049814 A2 | 6/2005 |
| WO | WO-2007/078203 A1 | 7/2007 |
| WO | WO-2011/004146 A1 | 1/2011 |

OTHER PUBLICATIONS

Sperry Journal of Virology, 2005, vol. 79, No. 6, pp. 3391-3400.*
Altschul et al., Basic local alignment search tool. *J. Mol. Biol.* 215: 403-10 (1990).
Ammayapppan et al., Identification of sequence changes responsible for the attenuation of avian infectious bronchitis virus strain Arkansas DPI, Arch. Virol., 154(3):495-9 (2009).
Anonymous: "EM_STD:KF377577", Oct. 30, 2013.
Armesto et al., A recombinant avian infectious bronchitis virus expressing a heterologous spike gene belonging to the 4/91 serotype, PLoS One, 6(8):e24352 (2011).
Armesto et al., The replicase gene of avian coronavirus infectious bronchitis virus is a determinant of pathogenicity, PLoS One, 4(10):e7384 (2009).
Armesto et al., Transient dominant selection for the modification and generation of recombinant infectious bronchitis coronaviruses, Methods Mol. Biol., 454:255-73 (2008).
Ausubel et al., Short Protocols in Molecular Biology, 4th edition, Chapter 18 (1999).
Britton et al., Generation of a recombinant avian coronavirus infectious bronchitis virus using transient dominant selection, J. Virol. Methods, 123(2):203-11 (2005).
Britton et al., Modification of the avian coronavirus infectious bronchitis virus for vaccine development, Bioeng. Bugs., 3(2):114-9 (2012).
Casais et al., Recombinant avian infectious bronchitis virus expressing a heterologous spike gene demonstrates that the spike protein is a determinant of cell tropism, J. Virol., 77(16):9084-9 (2003).
Casais et al., Reverse genetics system for the avian coronavirus infectious bronchitis virus, J. Virol., 75(24):12359-69 (2001).
Devereux et al., A comprehensive set of sequence analysis programms for the VAX. Nucl. Acids Res.12: 387-95 (1984).
Cavanagh et al., Manipulation of the infectious bronchitis coronavirus genome for vaccine development and analysis of the accessory proteins, Vaccine, 25(30):5558-62 (2007).
International Preliminary Report on Patentability, International Application No. PCT/GB2015/052124, dated Jan. 24, 2017.
International Search Report and Written Opinion, International Application No. PCT/GB2015/052124, dated Oct. 9, 2015.
Larkin et al., Clustal W and Clustal X version 2.0, Bioinformatics, 23(21):2947-8 (2007).
Menachery et al., Attenuation and restoration of severe acute respiratory syndrome coronavirus mutant lacking 2'-o-methyltransferase activity, J. Virol., 88(8):4251-64 (2014).
Tatusova et al., BLAST 2 Sequences, a new tool for comparing protein and nucleotide sequences, FEMS Microbiol. Lett., 174(2):247-50 (1999).

(Continued)

*Primary Examiner* — Bao Q Li
(74) *Attorney, Agent, or Firm* — Marshall, Gerstein & Borun LLP

(57) ABSTRACT

The present invention provides a live, attenuated coronavirus comprising a variant replicase gene encoding polyproteins comprising a mutation in one or more of non-structural protein(s) (nsp)-10, nsp-14, nsp-15 or nsp-16. The coronavirus may be used as a vaccine for treating and/or preventing a disease, such as infectious bronchitis, in a subject.

25 Claims, 15 Drawing Sheets

Specification includes a Sequence Listing.

(56) References Cited

OTHER PUBLICATIONS

Wang et al., Attenuation of porcine reproductive and respiratory syndrome virus strain MN184 using chimeric construction with vaccine sequence, Virology, 371(2):418-29 (2008).

Wei et al., Development and characterization of a recombinant infectious bronchitis virus expressing the ectodomain region of S1 gene of H120 strain, Appl. Microbiol. Biotechnol., 98(4):1727-35 (2014).

* cited by examiner

Nsp14

CORONAVIRUS

FIELD OF THE INVENTION

The present invention relates to an attenuated coronavirus comprising a variant replicase gene, which causes the virus to have reduced pathogenicity. The present invention also relates to the use of such a coronavirus in a vaccine to prevent and/or treat a disease.

BACKGROUND TO THE INVENTION

Avian infectious bronchitis virus (IBV), the aetiological agent of infectious bronchitis (IB), is a highly infectious and contagious pathogen of domestic fowl that replicates primarily in the respiratory tract but also in epithelial cells of the gut, kidney and oviduct. IBV is a member of the Order Nidovirales, Family Coronaviridae, Subfamily Corona virinae and Genus *Gammacoronavirus*; genetically very similar coronaviruses cause disease in turkeys, guinea fowl and pheasants.

Clinical signs of IB include sneezing, tracheal rales, nasal discharge and wheezing. Meat-type birds have reduced weight gain, whilst egg-laying birds lay fewer eggs and produce poor quality eggs. The respiratory infection predisposes chickens to secondary bacterial infections which can be fatal in chicks. The virus can also cause permanent damage to the oviduct, especially in chicks, leading to reduced egg production and quality; and kidney, sometimes leading to kidney disease which can be fatal.

IBV has been reported to be responsible for more economic loss to the poultry industry than any other infectious disease. Although live attenuated vaccines and inactivated vaccines are universally used in the control of IBV, the protection gained by use of vaccination can be lost either due to vaccine breakdown or the introduction of a new IBV serotype that is not related to the vaccine used, posing a risk to the poultry industry.

Further, there is a need in the industry to develop vaccines which are suitable for use in ovo, in order to improve the efficiency and cost-effectiveness of vaccination programmes. A major challenge associated with in ovo vaccination is that the virus must be capable of replicating in the presence of maternally-derived antibodies against the virus, without being pathogenic to the embryo. Current IBV vaccines are derived following multiple passage in embryonated eggs, this results in viruses with reduced pathogenicity for chickens, so that they can be used as live attenuated vaccines. However such viruses almost always show an increased virulence to embryos and therefore cannot be used for in ova vaccination as they cause reduced hatchability. A 70% reduction in hatchability is seen in some cases.

Attenuation following multiple passage in embryonated eggs also suffers from other disadvantages. It is an empirical method, as attenuation of the viruses is random and will differ every time the virus is passaged, so passage of the same virus through a different series of eggs for attenuation purposes will lead to a different set of mutations leading to attenuation. There are also efficacy problems associated with the process: some mutations will affect the replication of the virus and some of the mutations may make the virus too attenuated. Mutations can also occur in the S gene which may also affect immunogenicity so that the desired immune response is affected and the potential vaccine may not protect against the required serotype. In addition there are problems associated with reversion to virulence and stability of vaccines.

It is important that new and safer vaccines are developed for the control of IBV. Thus there is a need for IBV vaccines which are not associated with these issues, in particular vaccines which may be used for in ovo vaccination.

SUMMARY OF ASPECTS OF THE INVENTION

The present inventors have used a reverse genetics approach in order to rationally attenuate IBV. This approach is much more controllable than random attenuation following multiple passages in embryonated eggs because the position of each mutation is known and its effect on the virus, i.e. the reason for attenuation, can be derived.

Using their reverse genetics approach, the present inventors have identified various mutations which cause the virus to have reduced levels of pathogenicity. The levels of pathogenicity may be reduced such that when the virus is administered to an embryonated egg, it is capable of replicating without being pathogenic to the embryo. Such viruses may be suitable for in ovo vaccination, which is a significant advantage and has improvement over attenuated IBV vaccines produced following multiple passage in embryonated eggs.

Thus in a first aspect, the present invention provides a live, attenuated coronavirus comprising a variant replicase gene encoding polyproteins comprising a mutation in one or more of non-structural protein(s) (nsp)-10, nsp-14, nsp-15 or nsp-16.

The variant replicase gene may encode a protein comprising one or more amino acid mutations selected from the list of:
  Pro to Leu at position 85 of SEQ ID NO: 6,
  Val to Leu at position 393 of SEQ ID NO: 7;
  Leu to Ile at position 183 of SEQ ID NO: 8;
  Val to Ile at position 209 of SEQ ID NO: 9.

The replicase gene may encode a protein comprising the amino acid mutation Pro to Leu at position 85 of SEQ ID NO: 6.

The replicase gene may encode a protein comprising the amino acid mutations Val to Leu at position 393 of SEQ ID NO: 7; Leu to Ile at position 183 of SEQ ID NO: 8; and Val to Ile at position 209 of SEQ ID NO: 9.

The replicase gene may encodes a protein comprising the amino acid mutations Pro to Leu at position 85 of SEQ ID NO: 6; Val to Leu at position 393 of SEQ ID NO:7; Leu to Ile at position 183 of SEQ ID NO:8; and Val to Ile at position 209 of SEQ ID NO: 9.

The replicase gene may comprise one or more nucleotide substitutions selected from the list of:
  C to T at nucleotide position 12137;
  G to C at nucleotide position 18114;
  T to A at nucleotide position 19047; and
  G to A at nucleotide position 20139;
  compared to the sequence shown as SEQ ID NO: 1.

The coronavirus may be an infectious bronchitis virus (IBV).

The coronavirus may be IBV M41.

The coronavirus may comprise an S protein at least part of which is from an IBV serotype other than M41.

For example, the S1 subunit or the entire S protein may be from an IBV serotype other than M41.

The coronavirus according to the first aspect of the invention has reduced pathogenicity compared to a coronavirus expressing a corresponding wild-type replicase, such that when the virus is administered to an embryonated egg, it is capable of replicating without being pathogenic to the embryo.

In a second aspect, the present invention provides a variant replicase gene as defined in connection with the first aspect of the invention.

In a third aspect, the present invention provides a protein encoded by a variant coronavirus replicase gene according to the second aspect of the invention.

In a fourth aspect, the present invention provides a plasmid comprising a replicase gene according to the second aspect of the invention.

In a fifth aspect, the present invention provides a method for making the coronavirus according to the first aspect of the invention which comprises the following steps:
  (i) transfecting a plasmid according to the fourth aspect of the invention into a host cell;
  (ii) infecting the host cell with a recombining virus comprising the genome of a coronavirus strain with a replicase gene;
  (iii) allowing homologous recombination to occur between the replicase gene sequences in the plasmid and the corresponding sequences in the recombining virus genome to produce a modified replicase gene; and
  (iv) selecting for recombining virus comprising the modified replicase gene.

The recombining virus may be a vaccinia virus.

The method may also include the step:
  (v) recovering recombinant coronavirus comprising the modified replicase gene from the DNA from the recombining virus from step (iv).

In a sixth aspect, the present invention provides a cell capable of producing a coronavirus according to the first aspect of the invention.

In a seventh aspect, the present invention provides a vaccine comprising a coronavirus according to the first aspect of the invention and a pharmaceutically acceptable carrier.

In an eighth aspect, the present invention provides a method for treating and/or preventing a disease in a subject which comprises the step of administering a vaccine according to the seventh aspect of the invention to the subject.

Further aspects of the invention provide:
  the vaccine according to the seventh aspect of the invention for use in treating and/or preventing a disease in a subject.
  use of a coronavirus according to the first aspect of the invention in the manufacture of a vaccine for treating and/or preventing a disease in a subject.

The disease may be infectious bronchitis (IB).

The method of administration of the vaccine may be selected from the group consisting of; eye drop administration, intranasal administration, drinking water administration, post-hatch injection and in ovo injection.

Vaccination may be by in ova vaccination.

The present invention also provides a method for producing a vaccine according to the seventh aspect of the invention, which comprises the step of infecting a cell according to the sixth aspect of the invention with a coronavirus according to the first aspect of the invention.

DESCRIPTION OF THE FIGURES

FIG. 9A shows the results for M41-R and M41-K. FIG. 9B shows the results for M41-nsp10 rep; M41R-nsp14, 15, 16 rep; M41R-nsp10, 15 rep; M41R-nsp10, 15, 16 rep; M41R-nsp10, 14, 15 rep; and M41R-nsp10, 14, 16.

DETAILED DESCRIPTION

Figure 1:
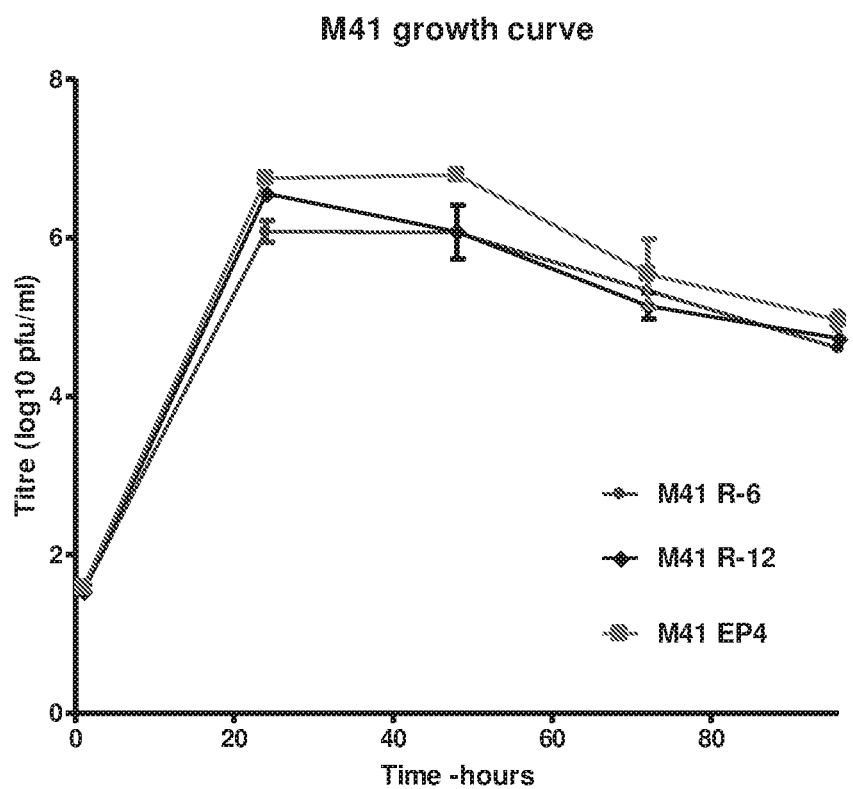
FIG. 1—Growth kinetics of M41-R-6 and M41-R-12 compared to M41-CK (M41 EP4) on CK cells FIG. 2—Clinical signs, snicking and wheezing, associated with M41-R-6 and M41-R-12 compared to M41-CK (M41 EP4) and Beau-R (Bars show mock, Beau-R, M41-R 6, M41-R 12, M41-CK EP4 from left to right of each timepoint).

The present invention provides a coronavirus comprising a variant replicase gene which, when expressed in the coronavirus, causes the virus to have reduced pathogenicity compared to a corresponding coronavirus which comprises the wild-type replicase gene.

Coronavirus

*Gammacoronavirus* is a genus of animal virus belonging to the family Coronaviridae. Coronaviruses are enveloped viruses with a positive-sense single-stranded RNA genome and a helical symmetry.

The genomic size of coronaviruses ranges from approximately 27 to 32 kilobases, which is the longest size for any known RNA virus.

Coronaviruses primarily infect the upper respiratory or gastrointestinal tract of mammals and birds. Five to six different currently known strains of coronaviruses infect humans. The most publicized human coronavirus, SARS-CoV which causes severe acute respiratory syndrome (SARS), has a unique pathogenesis because it causes both upper and lower respiratory tract infections and can also cause gastroenteritis. Middle East respiratory syndrome coronavirus (MERS-CoV) also causes a lower respiratory tract infection in humans. Coronaviruses are believed to cause a significant percentage of all common colds in human adults.

Coronaviruses also cause a range of diseases in livestock animals and domesticated pets, some of which can be serious and are a threat to the farming industry. Economically significant coronaviruses of livestock animals include infectious bronchitis virus (IBV) which mainly causes respiratory disease in chickens and seriously affects the poultry industry worldwide; porcine coronavirus (transmissible gastroenteritis, TGE) and bovine coronavirus, which both result in diarrhoea in young animals. Feline coronavirus has two forms, feline enteric coronavirus is a pathogen of minor clinical significance, but spontaneous mutation of this virus can result in feline infectious peritonitis (FIP), a disease associated with high mortality.

There are also two types of canine coronavirus (CCoV), one that causes mild gastrointestinal disease and one that has been found to cause respiratory disease. Mouse hepatitis virus (MHV) is a coronavirus that causes an epidemic murine illness with high mortality, especially among colonies of laboratory mice.

Coronaviruses are divided into four groups, as shown below:

Alpha
  Canine coronavirus (CCoV)
  Feline coronavirus (FeCoV)
  Human coronavirus 229E (HCoV-229E)
  Porcine epidemic diarrhoea virus (PEDV)
  Transmissible gastroenteritis virus (TGEV)
  Human Coronavirus NL63 (NL or New Haven)
Beta
  Bovine coronavirus (BCoV)
  Canine respiratory coronavirus (CRCoV)—Common in SE Asia and Micronesia
  Human coronavirus OC43 (HCoV-OC43)
  Mouse hepatitis virus (MHV)
  Porcine haemagglutinating encephalomyelitis virus (HEV)
  Rat coronavirus (Roy). Rat Coronavirus is quite prevalent in Eastern Australia where, as of March/April 2008, it has been found among native and feral rodent colonies.
  (No common name as of yet) (HCoV-HKU1)
    Severe acute respiratory syndrome coronavirus (SARS-CoV)
  Middle East respiratory syndrome coronavirus (MERS-CoV)
Gamma
  Infectious bronchitis virus (IBV)
  Turkey coronavirus (Bluecomb disease virus)
  Pheasant coronavirus
  Guinea fowl coronavirus
Delta
  Bulbul coronavirus (BuCoV)
  Thrush coronavirus (ThCoV)
  Munia coronavirus (MuCoV)
  Porcine coronavirus (PorCov) HKU15

The variant replicase gene of the coronavirus of the present invention may be derived from an alphacoronavirus such as TGEV; a betacoronavirus such as MHV; or a *gammacoronavirus* such as IBV.

As used herein the term "derived from" means that the replicase gene comprises substantially the same nucleotide sequence as the wild-type replicase gene of the relevant coronavirus. For example, the variant replicase gene of the present invention may have up to 80%, 85%, 90%, 95%, 98% or 99% identity with the wild type replicase sequence. The variant coronavirus replicase gene encodes a protein comprising a mutation in one or more of non-structural protein (nsp)-10, nsp-14, nsp-15 or nsp-16 when compared to the wild-type sequence of the non-structural protein.

IBV

Avian infectious bronchitis (IB) is an acute and highly contagious respiratory disease of chickens which causes significant economic losses. The disease is characterized by respiratory signs including gasping, coughing, sneezing, tracheal rales, and nasal discharge. In young chickens, severe respiratory distress may occur. In layers, respiratory distress, nephritis, decrease in egg production, and loss of internal egg quality and egg shell quality are common.

In broilers, coughing and rattling are common clinical signs, rapidly spreading in all the birds of the premises. Morbidity is 100% in non-vaccinated flocks. Mortality varies depending on age, virus strain, and secondary infections but may be up to 60% in non-vaccinated flocks.

The first IBV serotype to be identified was Massachusetts, but in the United States several serotypes, including Arkansas and Delaware, are currently circulating, in addition to the originally identified Massachusetts type.

The IBV strain Beaudette was derived following at least 150 passages in chick embryos. IBV Beaudette is no longer pathogenic for hatched chickens but rapidly kills embryos.

H120 is a commercial live attenuated IBV Massachusetts serotype vaccine strain, attenuated by approximately 120 passages in embryonated chicken eggs. H52 is another Massachusetts vaccine, and represents an earlier and slightly more pathogenic passage virus (passage 52) during the development of H120. Vaccines based on H120 are commonly used.

IB QX is a virulent field isolate of IBV. It is sometimes known as "Chinese QX" as it was originally isolated following outbreaks of disease in the Qingdao region in China in the mid 1990s. Since that time the virus has crept towards Europe. From 2004, severe egg production issues have been identified with a very similar virus in parts of Western Europe, predominantly in the Netherlands, but also reported from Germany, France, Belgium, Denmark and in the UK.

The virus isolated from the Dutch cases was identified by the Dutch Research Institute at Deventer as a new strain that they called D388. The Chinese connection came from further tests which showed that the virus was 99% similar to the Chinese QX viruses. A live attenuated QX-like IBV vaccine strain has now been developed.

IBV is an enveloped virus that replicates in the cell cytoplasm and contains an non-segmented, single-stranded, positive sense RNA genome. IBV has a 27.6 kb RNA genome and like all coronaviruses contains the four structural proteins; spike glycoprotein (S), small membrane protein (E), integral membrane protein (M) and nucleocapsid protein (N) which interacts with the genomic RNA.

The genome is organised in the following manner: 5'UTR—polymerase (replicase) gene—structural protein genes (S-E-M-N)—UTR 3'; where the UTR are untranslated regions (each ~500 nucleotides in IBV).

The lipid envelope contains three membrane proteins: S, M and E. The IBV S protein is a type I glycoprotein which oligomerizes in the endoplasmic reticulum and is assembled into homotrimer inserted in the virion membrane via the transmembrane domain and is associated through non-covalent interactions with the M protein. Following incorporation into coronavirus particles, the S protein is responsible for binding to the target cell receptor and fusion of the viral and cellular membranes. The S glycoprotein consists of four domains: a signal sequence that is cleaved during synthesis; the ectodomain, which is present on the outside of the virion particle; the transmembrane region responsible for anchoring the S protein into the lipid bilayer of the virion particle; and the cytoplasmic tail.

All coronaviruses also encode a set of accessory protein genes of unknown function that are not required for replication in vitro, but may play a role in pathogenesis. IBV encodes two accessory genes, genes 3 and 5, which both express two accessory proteins 3a, 3b and 5a, 5b, respectively.

The variant replicase gene of the coronavirus of the present invention may be derived from an IBV. For example the IBV may be IBV Beaudette, H120, H52, IB QX, D388 or M41.

The IBV may be IBV M41. M41 is a prototypic Massachusetts serotype that was isolated in the USA in 1941. It is an isolate used in many labs throughout the world as a pathogenic lab stain and can be obtained from ATCC (VR-21™). Attenuated variants are also used by several vaccine producers as IBV vaccines against Massachusetts serotypes causing problems in the field. The present inventors chose to use this strain as they had worked for many years on this virus, and because the sequence of the complete virus genome is available. The M41 isolate, M41-CK, used by the present inventors was adapted to grow in primary chick kidney (CK) cells and was therefore deemed amenable for recovery as an infectious virus from a cDNA of the complete genome. It is representative of a pathogenic IBV and therefore can be analysed for mutations that cause either loss or reduction in pathogenicity.

The genome sequence of IBV M41-CK is provided as SEQ ID NO: 1.

```
IBV M41-CK Sequence
                                                         SEQ ID NO: 1
ACTTAAGATAGATATTAATATATATCTATCACACTAGCCTTGCGCTAGATTTCCAACTTA

ACAAAACGGACTTAAATACCTACAGCTGGTCCTCATAGGTGTTCCATTGCAGTGCACTTT

AGTGCCCTGGATGGCACCTGGCCACCTGTCAGGTTTTTGTTATTAAAATCTTATTGTTGC

TGGTATCACTGCTTGTTTTGCCGTGTCTCACTTTATACATCCGTTGCTTGGGCTACCTAG

TATCCAGCGTCCTACGGGCGCCGTGGCTGGTTCGAGTGCGAAGAACCTCTGGTTCATCTA

GCGGTAGGCGGGTGTGTGGAAGTAGCACTTCAGACGTACCGGTTCTGTTGTGTGAAATAC

GGGGTCACCTCCCCCCACATACCTCTAAGGGCTTTTGAGCCTAGCGTTGGGCTACGTTCT

CGCATAAGGTCGGCTATACGACGTTTGTAGGGGGTAGTGCCAAACAACCCCTGAGGTGAC

AGGTTCTGGTGGTGTTTAGTGAGCAGACATACAATAGACAGTGACAACATGGCTTCAAGC

CTAAAACAGGGAGTATCTGCGAAACTAAGGGATGTCATTGTTGTATCCAAAGAGATTGCT

GAACAACTTTGTGACGCTTTGTTTTTCTATACGTCACACAACCCTAAGGATTACGCTGAT

GCTTTTGCAGTTAGGCAGAAGTTTGATCGTAATCTGCAGACTGGGAAACAGTTCAAATTT

GAAACTGTGTGTGGTCTCTTCCTCTTGAAGGGAGTTGACAAAATAACACCTGGCGTCCCA

GCAAAAGTCTTAAAAGCCACTTCTAAGTTGGCAGATTTAGAAGACATCTTTGGTGTCTCT

CCCTTTGCAAGAAAATATCGTGAACTTTTGAAGACAGCATGCCAGTGGTCTCTTACTGTA

GAAACACTGGATGCTCGTGCACAAACTCTTGATGAAATTTTTGACCCTACTGAAATACTT

TGGCTTCAGGTGGCAGCAAAAATCCAAGTTTCGGCTATGGCGATGCGCAGGCTTGTTGGA

GAAGTAACTGCAAAAGTCATGGATGCTTTGGGCTCAAATATGAGTGCTCTTTTCCAGATT

TTTAAACAACAAATAGTCAGAATTTTTCAAAAAGCGCTGGCTATTTTTGAGAATGTGAGT

GAATTACCACAGCGTATTGCAGCACTTAAGATGGCTTTTGCTAAGTGTGCCAAGTCCATT

ACTGTTGTGGTTATGGAGAGGACTCTAGTTGTTAGAGAGTTCGCAGGAACTTGTCTTGCA

AGCATTAATGGTGCTGTTGCAAAATTCTTTGAAGAACTCCCAAATGGTTTCATGGGTGCT

AAAATTTTCACTACACTTGCCTTCTTTAGGGAGGCTGCAGTGAAAATTGTGGATAACATA

CCAAATGCACCGAGAGGCACTAAAGGGTTTGAAGTCGTTGGTAATGCCAAAGGTACACAA
```

-continued

```
GTTGTTGTGCGTGGCATGGGAAATGACTTAACACTGGTTGAGCAAAAAGCTGAAATTGCT
GTGGAGTCAGAAGGTTGGTCTGCAATTTTGGGTGGACATCTTTGCTATGTCTTTAAGAGT
GGTGATCGCTTTTACGCGGCACCTCTTTCAGGAAATTTTGCATTGCATGATGTGCATTGT
TGTGAGCGTGTTGTCTGTCTTTCTGATGGTGTAACACCGGAGATAAATGATGGACTTATT
CTTGCAGCAATCTACTCTTCTTTTAGTGTCGCAGAACTTGTGGCAGCCATTAAAAGGGGT
GAACCATTTAAGTTTCTGGGTCATAAATTTGTGTATGCAAAGGATGCAGCAGTTTCTTTT
ACATTAGCGAAGGCTGCTACTATTGCAGATGTTTTGAAGCTGTTTCAATCAGCGCGTGTG
AAAGTAGAAGATGTTTGGTCTTCACTTACTGAAAAGTCTTTTGAATTCTGGAGGCTTGCA
TATGGAAAAGTGCGTAATCTCGAAGAATTTGTTAAGACTTGTTTTTGTAAGGCTCAAATG
GCGATTGTGATTTTAGCGACAGTGCTTGGAGAGGGCATTTGGCATCTTGTTTCGCAAGTC
ATCTATAAAGTAGGTGGTCTTTTTACTAAAGTTGTTGACTTTTGTGAAAAATATTGGAAA
GGTTTTTGTGCACAGTTGAAAAGAGCTAAGCTCATTGTCACTGAAACCCTCTGTGTTTTG
AAAGGAGTTGCACAGCATTGTTTTCAACTATTGCTGGATGCAATACAGTTTATGTATAAA
AGTTTTAAGAAGTGTGCACTTGGTAGAATCCATGGAGACTTGCTCTTCTGGAAAGGAGGT
GTGCACAAAATTATTCAAGAGGGCGATGAAATTTGGTTTGAGGGCATTGATAGTATTGAT
GTTGAAGATCTGGGTGTTGTTCAAGAAAAATTGATTGATTTTGATGTTTGTGATAATGTG
ACACTTCCAGAGAACCAACCCGGTCATATGGTTCAAATCGAGGATGACGGAAAGAACTAC
ATGTTCTTCCGCTTCAAAAAGGATGAGAACATTTATTATACACCAATGTCACAGCTTGGT
GCTATTAATGTGGTTTGCAAAGCAGGCGGTAAAACTGTCACCTTTGGAGAAACTACTGTG
CAAGAAATACCACCACCTGATGTTGTGTTTATTAAGGTTAGCATTGAGTGTTGTGGTGAA
CCATGGAATACAATCTTCAAAAAGGCTTATAAGGAGCCCATTGAAGTAGAGACAGACCTC
ACAGTTGAACAATTGCTCTCTGTGGTCTATGAGAAAATGTGTGATGATCTCAAGCTGTTT
CCGGAGGCTCCAGAACCACCACCATTTGAGAATGTCACACTTGTTGATAAGAATGGTAAA
GATTTGGATTGCATAAAATCATGCCATCTGATCTATCGTGATTATGAGAGCGATGATGAC
ATCGAGGAAGAAGATGCAGAAGAATGTGACACGGATTCAGGTGATGCTGAGGAGTGTGAC
ACTAATTCAGAATGTGAAGAAGAAGATGAGGATACTAAAGTGTTGGCTCTTATACAAGAC
CCGGCAAGTAACAAATATCCTCTGCCTCTTGATGATGATTATAGCGTCTACAATGGATGT
ATTGTTCATAAGGACGCTCTCGATGTTGTGAATTTACCATCTGGTGAAGAAACCTTTGTT
GTCAATAACTGCTTTGAAGGGGCTGTTAAAGCTCTTCCGCAGAAAGTTATTGATGTTCTA
GGTGACTGGGGTGAGGCTGTTGATGCGCAAGAACAATTGTGTCAACAAGAATCAACTCGG
GTCATATCTGAGAAATCAGTTGAGGGTTTTACTGGTAGTTGTGATGCAATGGCTGAACAA
GCTATTGTTGAAGAGCAGGAAATAGTACCTGTTGTTGAACAAAGTCAGGATGTAGTTGTT
TTTACACCTGCAGACCTAGAAGTTGTTAAAGAAACAGCAGAAGAGGTTGATGAGTTTATT
CTCATTTCTGCTGTCCCTAAAGAAGAAGTTGTGTCTCAGGAGAAAGAGGAGCCACAGGTT
GAGCAAGAGCCTACCCTAGTTGTTAAAGCACAACGTGAGAAGAAGGCTAAAAAGTTCAAA
GTTAAACCAGCTACATGTGAAAAACCCAAATTTTTGGAGTACAAAACATGTGTGGGTGAT
TTGGCTGTTGTAATTGCCAAAGCATTGGATGAGTTTAAAGAGTTCTGCATTGTAAACGCT
GCAAATGAGCACATGTCGCATGGTGGTGGCGTTGCAAAGGCAATTGCAGACTTTTGTGGA
CCGGACTTTGTTGAATATTGCGCGGACTATGTTAAGAAACATGGTCCACAGCAAAAACTT
GTCACACCTTCATTTGTTAAAGGCATTCAATGTGTGAATAATGTTGTAGGACCTCGCCAT
GGAGACAGCAACTTGCGTGAGAAGCTTGTTGCTGCTTACAAGAGTGTTCTTGTAGGTGGA
```

-continued

```
GTGGTTAACTATGTTGTGCCAGTTCTCTCATCAGGGATTTTTGGTGTAGATTTTAAAATA

TCAATAGATGCTATGCGCGAAGCTTTTAAAGGTTGTGCCATACGCGTTCTTTTATTTTCT

CTGAGTCAAGAACACATCGATTATTTCGATGCAACTTGTAAGCAGAAGACAATTTATCTT

ACGGAGGATGGTGTTAAATACCGCTCTGTTGTTTTAAAACCTGGTGATTCTTTGGGTCAA

TTTGGACAGGTTTTTGCAAGAAATAAGGTAGTCTTTTCGGCTGATGATGTTGAGGATAAA

GAAATCCTCTTTATACCCACAACTGACAAGACTATTCTTGAATATTATGGTTTAGATGCG

CAAAAGTATGTAACATATTTGCAAACGCTTGCGCAGARATGGGATGTTCAATATAGAGAC

AATTTTGTTATATTAGAGTGGCGTGACGGAAATTGCTGGATTAGTTCAGCAATAGTTCTC

CTTCAAGCTGCTAAAATTAGATTTAAAGGTTTTCTTGCAGAAGCATGGGCTAAACTGTTG

GGTGGAGATCCTACAGACTTTGTTGCCTGGTGTTATGCAAGTTGCAATGCTAAAGTAGGT

GATTTTTCAGATGCTAATTGGCTTTTGGCCAATTTAGCAGAACATTTTGACGCAGATTAC

ACAAATGCACTTCTTAAGAAGTGTGTGTCGTGCAATTGTGGTGTTAAGAGTTATGAACTT

AGGGGTCTTGAAGCCTGTATTCAGCCAGTTCGAGCACCTAATCTTCTACATTTTAAAACG

CAATATTCAAATTGCCCAACCTGTGGTGCAAGTAGTACGGATGAAGTAATAGAAGCTTCA

TTACCGTACTTATTGCTTTTTGCTACTGATGGTCCTGCTACAGTTGATTGTGATGAAAAT

GCTGTAGGGACTGTTGTTTTCATTGGCTCTACTAATAGTGGCCATTGTTATACACAAGCC

GATGGTAAGGCTTTTGACAATCTTGCTAAGGATAGAAAATTTGGAAGGAAGTCGCCTTAC

ATTACAGCAATGTATACACGTTTTTCTCTTAGGAGTGAAAATCCCCTACTTGTTGTTGAA

CATAGTAAGGGTAAAGCTAAAGTAGTAAAAGAAGATGTTTCTAACCTTGCTACTAGTTCT

AAAGCCAGTTTTGACGATCTTACTGACTTTGAACACTGGTATGATAGCAACATCTATGAG

AGTCTTAAAGTGCAGGAGACACCTGATAATCTTGATGAATATGTGTCATTTACGACAAAG

GAAGATTCTAAGTTGCCACTGACACTTAAAGTTAGAGGGTATCAAATCAGTTGTTGACTTT

AGGTCTAAGGATGGTTTTACTTATAAGTTAACACCTGATACTGATGAAAATTCAAAAACA

CCAGTCTACTACCCAGTCTTGGATTCTATTAGTCTTAGGGCAATATGGGTTGAAGGCAGT

GCTAATTTTGTTGTTGGGCATCCAAATTATTATAGTAAGTCTCTCCGAATTCCCACGTTT

TGGGAAAATGCCGAGAGCTTTGTTAAAATGGGTTATAAAATTGATGGTGTAACTATGGGC

CTTTGGCGTGCAGAACACCTTAATAAACCTAATTTGGAGAGAATTTTTAACATTGCTAAG

AAAGCTATTGTTGGATCTAGTGTTGTTACTACGCAGTGTGGTAAAATACTAGTTAAAGCA

GCTACATACGTTGCCGATAAAGTAGGTGATGGTGTAGTTCGCAATATTACAGATAGAATT

AAGGGTCTTTGTGGATTCACACGTGGCCATTTTGAAAAGAAAATGTCCCTACAATTTCTA

AAGACACTTGTGTTCTTTTCTTTTATTTCTTAAAGGCTAGTGCTAAGAGTTTAGTTTCT

AGCTATAAGATTGTGTTATGTAAGGTGGTGTTTGCTACCTTACTTATAGTGTGGTTTATA

TACACAAGTAATCCAGTAGTGTTTACTGGAATACGTGTGCTAGACTTCCTATTTGAAGGT

TCTTTATGTGGTCCTTATAATGACTACGGTAAAGATTCTTTTGATGTGTTACGGTATTGT

GCAGGTGATTTTACTTGTCGTGTGTGTTTACATGATAGAGATTCACTTCATCTGTACAAA

CATGCTTATAGCGTAGAACAAATTTATAAGGATGCAGCTTCTGGCATTAACTTTAATTGG

AATTGGCTTTATTTGGTCTTTCTAATATTATTTGTTAAGCCAGTGGCAGGTTTTGTTATT

ATTTGTTATTGTGTTAAGTATTTGGTATTGAGTTCAACTGTGTTGCAAACTGGTGTAGGT

TTTCTAGATTGGTTTGTAAAAACAGTTTTTACCCATTTTAATTTTATGGGAGCGGGATTT

TATTTCTGGCTCTTTTACAAGATATACGTACAAGTGCATCATATATTGTACTGTAAGGAT
```

-continued

```
GTAACATGTGAAGTGTGCAAGAGAGTTGCACGCAGCAACAGGCAAGAGGTTAGCGTTGTA
GTTGGTGGACGCAAGCAAATAGTGCATGTTTACACTAATTCTGGCTATAACTTTTGTAAG
AGACATAATTGGTATTGTAGAAATTGTGATGATTATGGTCACCAAAATACATTTATGTCC
CCTGAAGTTGCTGGCGAGCTTTCTGAAAAGCTTAAGCGCCATGTTAAACCTACAGCATAT
GCTTACCACGTTGTGTATGAGGCATGCGTGGTTGATGATTTTGTTAATTTAAAATATAAG
GCTGCAATTGCTGGTAAGGATAATGCATCTTCTGCTGTTAAGTGTTTCAGTGTTACAGAT
TTTTTAAAGAAAGCTGTTTTTCTTAAGGAGGCATTGAAATGTGAACAAATATCTAATGAT
GGTTTTATAGTGTGTAATACACAGAGTGCGCATGCACTAGAGGAAGCAAAGAATGCAGCC
GTCTATTATGCGCAATATCTGTGTAAGCCAATACTTATACTTGACCAGGCACTTTATGAG
CAATTAATAGTAGAGCCTGTGTCTAAGAGTGTTATAGATAAAGTGTGTAGCATTTTGTCT
AATATAATATCTGTAGATACTGCAGCTTTAAATTATAAGGCAGGCACACTTCGTGATGCT
CTGCTTTCTATTACTAAAGACGAAGAAGCCGTAGATATGGCTATCTTCTGCCACAATCAT
GAAGTGGAATACACTGGTGACGGTTTTACTAATGTGATACCGTCATATGGTATGGACACT
GATAAGTTGACACCTCGTGATAGAGGGTTTTTGATAAATGCAGATGCTTCTATTGCTAAT
TTAAGAGTCAAAAATGCTCCTCCGGTAGTATGGAAGTTTTCTGATCTTATTAAATTGTCT
GACAGTTGCCTTAAATATTTAATTTCAGCTACTGTCAAGTCAGGAGGTCGTTTCTTTATA
ACAAAGTCTGGTGCTAAACAAGTTATTTCTTGTCATACCCAGAAACTGTTGGTAGAGAAA
AAGGCAGGTGGTGTTATTAATAACACTTTTAAATGGTTTATGAGTTGTTTTAAATGGCTT
TTTGTCTTTTATATACTTTTTACAGCATGTTGTTTGGGTTACTACTATATGGAGATGAAT
AAAAGTTTTGTTCACCCCATGTATGATGTAAACTCCACACTGCATGTTGAAGGGTTCAAA
GTTATAGACAAAGGTGTTATTAGAGAGATTGTGTCAGAAGATAATTGTTTCTCTAATAAG
TTTGTTAATTTTGACGCCTTTTGGGGTAAATCATATGAAAATAATAAAAACTGTCCAATT
GTTACAGTTGTTATAGATGGTGACGGGACAGTAGCTGTTGGTGTTCCTGGTTTTGTATCA
TGGGTTATGGATGGTGTTATGTTTGTGCATATGACACAGACTGATCGTAGACCTTGGTAC
ATTCCTACCTGGTTTAATAGAGAAATTGTTGGTTACACTCAGGATTCAATTATCACTGAG
GGTAGTTTTTATACATCTATAGCATTATTTTCTGCTAGATGTTTATATTTAACAGCCAGC
AATACACCTCAATTGTATTGTTTTAATGGCGACAATGATGCACCTGGAGCCTTACCATTT
GGTAGTATTATTCCTCATAGAGTATACTTCCAACCTAATGGTGTTAGGCTTATAGTTCCA
CAACAAATACTGCATACACCCTACATAGTGAAGTTTGTTTCAGACAGCTATTGTAGAGGT
AGTGTATGTGAGTATACTAAACCAGGTTACTGTGTGTCACTAGACTCCCAATGGGTTTTG
TTTAATGATGAATACATTAGTAAACCTGGCGTTTTCTGTGGTTCTACTGTTAGAGAACTT
ATGTTTAATATGGTTAGTACATTCTTTACTGGTGTCAACCCTAATATTTATATTCAGCTA
GCAACTATGTTTTAATACTAGTTGTTATTGTGTTAATTTTTGCAATGGTTATAAAGTTT
CAAGGTGTTTTTAAAGCTTATGCGACCATTGTGTTTACAATAATGTTAGTTTGGGTTATT
AATGCATTTGTTTTGTGTACATAGTTATAATAGTGTTTTAGCTGTTATATTATTAGTA
CTCTATTGCTATGCATCATTGGTTACAAGTCGCAATACTGCTATAATAATGCATTGTTGG
CTTGTTTTTACCTTTGGTTTAATAGTACCCACATGGTTGGCTTGTTGCTATCTGGGATTT
ATTCTTTATATGTACACACCGTTGGTTTTCTGGTGTTACGGTACTACTAAAAATACTCGT
AAGTTGTATGATGGCAACGAGTTTGTTGGTAATTATGACCTTGCTGCGAAGAGCACTTTT
GTTATTCGTGGTACTGAATTTGTTAAGCTTACGAATGAGATAGGTGATAAATTTGAAGCC
TATCTTTCTGCGTATGCTAGACTTAAATACTATTCAGGCACTGGTAGTGAGCAAGATTAC
```

-continued

```
TTGCAAGCTTGTCGTGCATGGTTAGCTTATGCTTTGGACCAATATAGAAATAGTGGTGTT

GAGGTTGTTTATACCCCACCGCGTTACTCTATTGGTGTTAGTAGACTACACGCTGGTTTT

AAAAAACTAGTTTCTCCTAGTAGTGCTGTTGAGAAGTGCATTGTTAGTGTCTCTTATAGA

GGCAATAATCTTAATGGACTGTGGCTGGGTGATTCTATTTACTGCCCACGCCATGTGTTA

GGTAAGTTTAGTGGTGACCAGTGGGGTGACGTACTAAACCTTGCTAATAATCATGAGTTT

GAAGTTGTAACTCAAAATGGTGTTACTTTGAATGTTGTCAGCAGGCGGCTTAAAGGAGCA

GTTTTAATTTTACAAACTGCAGTTGCCAATGCTGAAACTCCTAAGTATAAGTTTGTTAAA

GCTAATTGTGGTGATAGTTTCACTATAGCTTGTTCTTATGGTGGTACAGTTATAGGACTT

TACCCTGTCACTATGCGTTCTAATGGTACTATTAGAGCATCTTTCCTAGCAGGAGCCTGT

GGCTCAGTTGGTTTTAATATAGAAAAGGGTGTAGTTAATTTCTTTTATATGCACCATCTT

GAGTTACCTAATGCATTACACACTGGAACTGACCTAATGGGTGAGTTTTATGGTGGTTAT

GTAGATGAAGAGGTTGCGCAAAGAGTGCCACCAGATAATCTAGTTACTAACAATATTGTA

GCATGGCTCTATGGGCAATTATTAGTGTTAAAGAAAGTAGTTTTTCACAACCTAAATGG

TTGGAGAGTACTACTGTTTCTATTGAAGATTACAATAGGTGGGCTAGTGATAATGGTTTT

ACTCCATTTTCCACTAGTACTGCTATTACTAAATTAAGTGCTATAACTGGGGTTGATGTT

TGTAAACTCCTTCGCACTATTATGGTAAAAAGTGCTCAATGGGGTAGTGATCCCATTTTA

GGACAATATAATTTTGAAGACGAATTGACACCAGAATCTGTATTTAATCAAGTTGGTGGT

GTTAGGTTACAGTCTTCTTTTGTAAGAAAAGCTACATCTTGGTTTTGGAGTAGATGTGTA

TTAGCTTGCTTCTTGTTTGTGTTGTGCTATTGTCTTATTTACGGCAGTGCCACTTAAG

TTTTATGTACATGCAGCTGTTATTTTGTTGATGGCTGTGCTCTTTATTTCTTTTACTGTT

AAACATGTTATGGCATACATGGACACTTTCCTATTGCCTACATTGATTACAGTTATTATT

GGAGTTTGTGCTGAAGTCCCTTTCATATACAATACTCTAATTAGTCAAGTTGTTATTTTC

TTAAGCCAATGGTATGATCCTGTAGTCTTTGATACTATGGTACCATGGATGTTATTGCCA

TTAGTGTTGTACACTGCTTTTAAGTGTGTACAAGGCTGCTATATGAATTCTTTCAATACT

TCTTTGTTAATGCTGTATCAGTTTATGAAGTTAGGTTTTGTTATTTACACCTCTTGAAAC

ACTCTTACTGCATATACAGAAGGTAATTGGGAGTTATTCTTTGAGTTGGTTCACACTATT

GTGTTGGCTAATGTTAGTAGTAATTCCTTAATTGGTTTAATTGTTTTTAAGTGTGCTAAG

TGGATTTTATATTATTGCAATGCAACATACTTTAATAATTATGTGTTAATGGCAGTCATG

GTTAATGGCATAGGCTGGCTTTGCACCTGTTACTTTGGATTGTATTGGTGGGTTAATAAA

GTTTTTGGTTTAACCTTAGGTAAATACAATTTTAAAGTTTCAGTAGATCAATATAGGTAT

ATGTGTTTGCATAAGGTAAATCCACCTAAAACTGTGTGGGAGGTCTTTACTACAAATATA

CTTATACAAGGAATTGGAGGCGATCGTGTGTTGCCTATAGCTACAGTGCAATCTAAATTG

AGTGATGTAAAGTGTACAACTGTTGTTTTAATGCAGCTTTTGACTAAGCTTAATGTTGAA

GCAAATTCAAAAATGCATGCTTATCTTGTTGAGTTACACAATAAAATCCTCGCATCTGAT

GATGTTGGAGAGTGCATGGATAATTTATTGGGTATGCTTATAACACTATTTTGTATAGAT

TCTACTATTGATTTGGGTGAGTATTGTGATGATATACTTAAGAGGTCAACTGTATTACAA

TCGGTTACTCAAGAGTTTTCGCACATACCCTCGTATGCTGAATATGAAAGAGCTAAGAGT

ATTTATGAAAAGGTTTTAGCCGATTCTAAAAATGGTGGTGTAACACAGCAAGAGCTTGCT

GCATATCGTAAAGCTGCCAATATTGCAAAGTCAGTTTTTGATAGAGACTTGGCTGTTCAA

AAGAAGTTAGATAGCATGGCAGAACGTGCTATGACAACAATGTATAAAGAGGCGCGTGTA
```

-continued

```
ACTGATAGAAGAGCAAAATTAGTTTCATCATTACATGCACTACTTTTTTCAATGCTTAAG
AAAATAGATTCTGAGAAGCTTAATGTCTTATTTGACCAGGCGAATAGTGGTGTTGTACCC
CTAGCAACTGTTCCAATTGTTTGTAGTAATAAGCTTACCCTTGTTATACCAGACCCAGAG
ACGTGGGTCAAGTGTGTGGAGGGTGTGCATGTTACATATTCAACAGTTGTTTGGAATATA
GACTGTGTTACTGATGCCGATGGCACAGAGTTACACCCCACTTCTACAGGTAGTGGATTG
ACTTACTGTATAAGTGGTGATAATATAGCATGGCCTTTAAAGGTTAACTTGACTAGGAAT
GGGCATAATAAGGTTGATGTTGCCTTGCAAAATAATGAGCTTATGCCTCACGGTGTAAAG
ACAAAGGCTTGCGTAGCAGGTGTAGATCAAGCACATTGTAGCGTTGAGTCTAAATGTTAT
TATACAAGTATTAGTGGCAGTTCAGTTGTAGCTGCTATTACCTCTTCAAATCCTAATCTG
AAAGTAGCCTCTTTTTTGAATGAGGCAGGTAATCAGATTTATGTAGACTTAGACCGAGCA
TGTAAATTTGGTATGAAAGTGGGTGATAAGGTTGAAGTTGTTTACCTGTATTTTATAAAA
AATACGAGGTCTATTGTAAGAGGTATGGTACTTGGTGCTATATCTAATGTTGTTGTGTTA
CAATCTAAAGGTCATGAGACAGAGGAAGTGGATGCTGTAGGCATTCTCTCACTTTGTTCT
TTTGCAGTAGATCCTGCGGATACATATTGTAAATATGTGGCAGCAGGTAATCAACCTTTA
GGTAACTGTGTTAAAATGTTGACAGTACATAATGGTAGTGGTTTTGCAATAACATCAAAG
CCAAGTCCAACTCCGGATCAGGATTCTTATGGAGGAGCTTCTGTGTGTCTTTATTGTAGA
GCACATATAGCACACCCTGGCGGAGCAGGAAATTTAGATGGACGCTGTCAATTTAAAGGT
TCTTTTGTGCAAATACCTACTACGGAGAAAGATCCTGTTGGATTCTGTCTACGTAACAAG
GTTTGCACTGTTTGTCAGTGTTGGATTGGTTATGGATGTCAGTGTGATTCACTTAGACAA
CCTAAACCTTCTGTTCAGTCAGTTGCTGTTGCATCTGGTTTTGATAAGAATTATTTAAAC
GGGTACGGGGTAGCAGTGAGGCTCGGCTGATACCCCTAGCTAATGGATGTGACCCCGATG
TTGTAAAGCGAGCCTTTGATGTTTGTAATAAGGAATCAGCCGGTATGTTTCAAAATTTGA
AGCGTAACTGTGCACGATTCCAAGAAGTACGTGATACTGAAGATGGAAATCTTGAGTATT
GTGATTCTTATTTTGTGGTTAAACAAACCACTCCTAGTAATTATGAACATGAGAAAGCTT
GTTATGAAGACTTAAAGTCAGAAGTAACAGCTGATCATGATTTCTTTGTGTTCAATAAGA
ACATTTATAATATTAGTAGGCAGAGGCTTACTAAGTATACTATGATGGATTTTTGCTATG
CTTTGCGGCACTTTGACCCAAAGGATTGCGAAGTTCTTAAAGAAATACTTGTCACTTATG
GTTGTATAGAAGATTATCACCCTAAGTGGTTTGAAGAGAATAAGGATTGGTACGACCCAA
TAGAAACCCTAAATATTATGCCATGTTGGCTAAAATGGGACCTATTGTACGAGGTGCTT
TATTGAATGCTATTGAGTTCGGAAACCTCATGGTTGAAAAAGGTTATGTTGGTGTTATTA
CACTTGATAACCAAGATCTTAATGGCAAATTTTATGATTTTGGTGATTTTCAGAAGACAG
CGCCTGGTGCTGGTGTTCCTGTTTTTGATACGTATTATTCTTACATGATGCCCATCATAG
CCATGACTGATGCGTTGGCACCTGAGAGGTATTTTGAATATGATGTGCATAAGGGTTATA
AATCTTATGATCTCCTCAAGTATGATTATACTGAGGAGAAACAAGATTTGTTTCAGAAGT
ACTTTAAGTATTGGGATCAAGAGTATCACCCTAACTGTCGCGACTGTAGTGATGACAGGT
GTTTGATACATTGTGCAAACTTCAACATCTTGTTTTCTACACTTGTACCGCAGACTTCTT
TCGGTAATTTGTGTAGAAAGGTTTTTGTTGATGGTGTACCATTTATAGCTACTTGTGGCT
ATCATTCTAAGGAACTTGGTGTTATTATGAATCAAGATAACACCATGTCATTTTCAAAAA
TGGGTTTGAGTGAACTCATGGAGTTTGTTGGAGATCGTGGCTTGTTAGTGGGACATGCA
ATAAATTAGTGGATCTTAGAACGTCTTGTTTTAGTGTTTGTGCTTTAGCGTCTGGTATTA
CTCATCAAACGGTAAAACCAGGTCACTTTAACAAGGATTTCTACGATTTTGCAGAGAAGG
```

-continued

```
CTGGTATGTTTAAGGAAGGTTCTTCTATACCACTTAAACATTTCTTCTACCCACAGACTG

GTAATGCTGCTATAAACGATTATGATTATTATCGTTATAACAGGCCTACCATGTTTGATA

TACGTCAACTTTTATTTTGTTTAGAAGTGACTTCTAAATATTTTGAATGTTATGAAGGCG

GCTGTATACCAGCAAGCCAAGTTGTAGTTAACAATTTAGATAAGAGTGCAGGTTATCCGT

TCAATAAGTTTGGAAAGGCCCGTCTCTATTATGAAATGAGTCTAGAGGAGCAGGACCAAC

TCTTTGAGAGTACAAAGAAGAACGTCCTGCCTACTATAACTCAGATGAATTTAAAATATG

CCATATCCGCGAAAAATAGAGCGCGTACAGTGGCAGGTGTGTCTATCCTTTCTACTATGA

CTAATAGGCAGTTTCATCAGAAGATTCTTAAGTCTATAGTCAACACTAGAAACGCTCCTG

TAGTTATTGGAACAACCAAGTTTTATGGCGGTTGGGATAACATGTTGAGAAACCTTATTC

AGGGTGTTGAAGACCCGATTCTTATGGGTTGGGATTATCCAAAGTGTGATAGAGCAATGC

CTAATTTGTTGCGTATAGCAGCATCTTTAGTACTCGCTCGTAAACACACTAATTGTTGTA

CTTGGTCTGAACGCGTTTATAGGTTGTATAATGAATGCGCTCAGGTTTTATCTGAAACTG

TCTTAGCTACAGGTGGTATATATGTGAAACCTGGTGGTACTAGCAGTGGAGATGCTACTA

CTGCTTATGCAAACAGTGTTTTCAACATAATACAAGCCACATCTGCTAATGTTGCGCGTC

TTTTGAGTGTTATAACGCGTGATATTGTATATGATGACATTAAGAGCTTGCAGTATGAAT

TGTACCAGCAGGTTTATAGGCGAGTCAATTTTGACCCAGCATTTGTTGAAAAGTTTTATT

CTTATTTGTGTAAGAATTTCTCATTGATGATCTTGTCTGACGACGGTGTTGTTTGTTATA

ACAACACATTAGCCAAACAAGGTCTTGTAGCAGATATTTCTGGTTTTAGAGAAGTTCTCT

ACTATCAGAACAATGTTTTTATGGCTGATTCTAAATGTTGGGTTGAACCAGATTTAGAAA

AAGGCCCACATGAATTTTGTTCACAGCACACAATGTTAGTGGAGGTTGATGGTGAGCCTA

GATACTTGCCATATCCAGACCCATCACGTATTTGTGTGCATGTGTTTTTGTAGATGATT

TGGATAAGACAGAATCTGTGGCTGTTATGGAGCGTTATATCGCTCTTGCCATAGATGCGT

ACCCACTAGTACATCATGAAAATGAGGAGTACAAGAAGGTATTCTTTGTGCTTCTTTCAT

ACATCAGAAAACTCTATCAAGAGCTTTCTCAGAATATGCTTATGGACTACTCTTTTGTAA

TGGATATAGATAAGGGTAGTAAATTTTGGGAACAGGAGTTCTATGAAAATATGTATAGAG

CCCCTACAACATTACAGTGTTGTGGCGTTTGTGTAGTGTGTAATAGTCAAACTATATTGC

GCTGTGGTAATTGTATTCGCAAACCATTTTTGTGTTGTAAGTGTTGCTATGACCATGTCA

TGCACACAGACCACAAAAATGTTTTGTCTATAAATCCTTACATTTGCTCACAGCCAGGTT

GTGGTGAAGCAGATGTTACTAAATTGTACCTCGGAGGTATGTCATACTTCTGCGGTAATC

ATAAACCAAAGTTATCAATACCGTTAGTATCTAATGGTACAGTGTTTGGAATTTACAGGG

CTAATTGTGCAGGTAGCGAAAATGTTGATGATTTTAATCAACTAGCTACTACTAATTGGT

CTACTGTGGAACCTTATATTTTGGCAAATCGTTGTGTAGATTCGTTGAGACGCTTTGCTG

CAGAGACAGTAAAAGCTACAGAAGAATTACATAAGCAACAATTTGCTAGTGCAGAAGTGA

GAGAAGTACTCTCAGATCGTGAATTGATTCTGTCTTGGGAGCCAGGTAAAACCAGGCCTC

CATTGAATAGAAATTATGTTTTCACTGGCTTTCACTTTACTAGAACTAGTAAAGTTCAGC

TCGGTGATTTTACATTTGAAAAGGTGAAGGTAAGGACGTTGTCTATTATCGAGCGACGT

CTACTGCTAAATTGTCTGTTGGAGACATTTTTGTTTAACCTCACACAATGTTGTTTCTC

TTATAGCGCCAACGTTGTGTCCTCAGCAAACCTTTTCTAGGTTTGTGAATTTAAGACCTA

ATGTGATGGTACCTGCGTGTTTTGTAAATAACATTCCATTGTACCATTTAGTAGGCAAGC

AGAAGCGTACTACAGTACAAGGCCCTCCTGGCAGTGGTAAATCCCATTTTGCTATAGGAT
```

-continued

```
TGGCGGCTTACTTTAGTAACGCCCGTGTCGTTTTACTGCATGCTCTCATGCAGCTGTTG

ATGCTTTATGTGAAAAAGCTTTTAAGTTTCTTAAAGTAGATGATTGCACTCGTATAGTAC

CTCAAAGGACTACTATCGATTGCTTCTCTAAGTTTAAAGGTAATGACACAGGCAAAAGT

ACATTTTTAGTACTATTAATGCCTTGCCAGAAGTTAGTTGTGACATTCTTTTGGTTGACG

AGGTTAGTATGTTGACCAATTACGAATTGTCTTTTATTAATGGTAAGATAAACTATCAAT

ATGTTGTGTATGTAGGTGATCCTGCTCAATTACCGGCGCCTCGTACGTTGCTTAACGGTT

CACTCTCTCCAAAGGATTATAATGTTGTCACAAACCTTATGGTTTGTGTTAAACCTGACA

TTTTCCTTGCAAAGTGTTACCGTTGTCCTAAAGAAATTGTAGATACTGTTTCTACTCTTG

TATATGATGGAAAGTTTATTGCAAATAACCCGGAATCACGTCAGTGTTTCAAGGTTATAG

TTAATAATGGTAATTCTGATGTAGGACATGAAAGTGGCTCAGCCTACAACATAACTCAAT

TAGAATTTGTGAAAGATTTTGTCTGTCGCAATAAGGAATGGCGGGAAGCAACATTCATTT

CACCTTATAATGCTATGAACCAGAGAGCCTACCGTATGCTTGGACTTAATGTTCAGACAG

TAGACTCGTCTCAAGGTTCGGAGTATGATTATGTTATCTTTTGTGTTACTGCAGATTCGC

AGCATGCACTGAATATTAACAGATTCAATGTAGCGCTTACAAGAGCCAAGCGTGGTATAC

TAGTTGTCATGCGTCAGCGTGATGAACTATATTCAGCTCTTAAGTTTATAGAGCTTGATA

GTGTAGCAAGTCTGCAAGGTACAGGCTTGTTTAAAATTTGCAACAAAGAGTTTAGTGGTG

TTCACCCAGCTTATGCAGTCACAACTAAGGCTCTTGCTGCAACTTATAAAGTTAATGATG

AACTTGCTGCACTTGTTAACGTGGAAGCTGGTTCAGAAATAACATATAAACATCTTATTT

CTTTGTTAGGGTTTAAGATGAGTGTTAATGTTGAAGGCTGCCACAACATGTTTATAACAC

GTGATGAGGCTATCCGCAACGTAAGAGGTTGGGTAGGTTTTGATGTAGAAGCAACACATG

CTTGCGGTACTAACATTGGTACTAACCTGCCTTTCCAAGTAGGTTTCTCTACTGGTGCAG

ACTTTGTAGTTACGCCTGAGGGACTTGTAGATACTTCAATAGGCAATAATTTTGAGCCTG

TGAATTCTAAAGCACCTCCAGGTGAACAATTTAATCACTTGAGAGCGTTATTCAAAAGTG

CTAAACCTTGGCATGTTGTAAGGCCAAGGATTGTGCAAATGTTAGCGGATAACCTGTGCA

ACGTTTCAGATTGTGTAGTGTTTGTCACGTGGTGTCATGGCCTAGAACTAACCACTTTGC

GCTATTTTGTTAAAATAGGCAAGGACCAAGTTTGTTCTTGCGGTTCTAGAGCAACAACTT

TTAATTCTCATACTCAGGCTTATGCTTGTTGGAAGCATTGCTTGGGTTTTGATTTTGTTT

ATAATCCACTCTTAGTGGATATTCAACAGTGGGGTTATTCTGGTAACCTACAATTTAACC

ATGATTTGCATTGTAATGTGCATGGACACGCACATGTAGCTTCTGCGGATGCTATTATGA

CGCGTTGTCTTGCAATTAATAATGCATTTTGTCAAGATGTCAACTGGGATTTAACTTACC

CTCATATAGCAAATGAGGATGAAGTCAATTCTAGCTGTAGATATTTACAACGCATGTATC

TTAATGCATGTGTTGATGCTCTTAAAGTTAACGTTGTCTATGATATAGGCAACCCTAAAG

GTATAAAATGTGTTAGACGTGGAGACTTAAATTTTAGATTCTATGATAAGAATCCAATAG

TACCCAATGTCAAGCAGTTTGAGTATGACTATAATCAGCACAAAGATAAGTTTGCTGATG

GTCTTTGTATGTTTTGGAATTGTAATGTGGATTGTTATCCCGACAATTCCTTAGTTTGTA

GGTACGACACACGAAATTTGAGTGTGTTTAACCTACCTGGTTGTAATGGTGGTAGCTTGT

ATGTTAACAAGCATGCATTCCACACACCTAAATTTGATCGCACTAGCTTTCGTAATTTGA

AAGCTATGCCATTCTTTTTCTATGACTCATCGCCTTGCGAGACCATTCAATTGGATGGAG

TTGCGCAAGACCTTGTGTCATTAGCTACGAAAGATTGTATCACAAAATGCAACATAGGCG

GTGCTGTTTGTAAAAAGCACGCACAAATGTATGCAGATTTTGTGACTTCTTATAATGCAG

CTGTTACTGCTGGTTTTACTTTTTGGGTTACTAATAATTTTAACCCATATAATTTGTGGA
```

-continued

```
AAAGTTTTTCAGCTCTCCAGTCTATCGACAATATTGCTTATAATATGTATAAGGGTGGTC

ATTATGATGCTATTGCAGGAGAAATGCCCACTATCGTAACTGGAGATAAAGTTTTTGTTA

TAGATCAAGGCGTAGAAAAAGCAGTTTTTTTTAATCAAACAATTCTGCCTAGATCTGTAG

CGTTTGAGCTGTATGCGAAGAGAAATATTCGCACACTGCCAAACAACCGTATTTTGAAAG

GTTTGGGTGTAGATGTGACTAATGGATTTGTAATTTGGGATTACACGAACCAAACACCAC

TATACCGTAATACTGTTAAGGTATGTGCATATACAGACATAGAACCAAATGGCCTAATAG

TGCTGTATGATGATAGATATGGTGATTACCAGTCTTTTCTAGCTGCTGATAATGCTGTTT

TAGTTTCTACACAGTGTTACAAGCGGTATTCGTATGTAGAAATACCGTCAAACCTGCTTG

TTCAGAACGGTATTCCGTTAAAAGATGGAGCGAACCTGTATGTTTATAAGCGTGTTAATG

GTGCGTTTGTTACGCTACCTAACACATTAAACACACAGGGTCGCAGTTATGAAACTTTTG

AACCTCGTAGTGATGTTGAGCGTGATTTTCTCGACATGTCTGAGGAGAGTTTTGTAGAAA

AGTATGGTAAAGAATTAGGTCTACAGCACATACTGTATGGTGAAGTTGATAAGCCCCAAT

TAGGTGGTTTACACACTGTTATAGGTATGTGCAGACTTTTACGTGCGAATAAGTTGAACG

CAAAGTCTGTTACTAATTCTGATTCTGATGTCATGCAAAATTATTTTGTATTGGCAGACA

ATGGTTCCTACAAGCAAGTGTGTACTGTTGTGGATTTGCTGCTTGATGATTTCTTAGAAC

TTCTTAGGAACATACTGAAAGAGTATGGTACTAATAAGTCTAAAGTTGTAACAGTGTCAA

TTGATTACCATAGCATAAATTTTATGACTTGGTTTGAAGATGGCATTATTAAAACATGTT

ATCCACAGCTTCAATCAGCATGGACGTGTGGTTATAATATGCCTGAACTTTATAAAGTTC

AGAATTGTGTTATGGAACCTTGCAACATTCCTAATTATGGTGTTGGAATAGCGTTGCCAA

GTGGTATTATGATGAATGTGGCAAAGTATACACAACTCTGTCAATACCTTTCGAAAACAA

CAATGTGTGTACCGCATAATATGCGAGTAATGCATTTTGGAGCTGGAAGTGACAAAGGAG

TGGCTCCAGGTAGTACTGTTCTTAAACAATGGCTCCCAGAAGGGACACTCCTTGTCGATA

ATGATATTGTAGACTATGTGTCTGATGCACATGTTTCTGTGCTTTCAGATTGCAATAAAT

ATAAGACAGAGCACAAGTTTGATCTTGTGATATCTGATATGTATACAGACAATGATTCAA

AAAGAAAGCATGAAGGCGTGATAGCCAATAATGGCAATGATGACGTTTTCATATATCTCT

CAAGTTTTCTTCGTAATAATTTGGCTCTAGGTGGTAGTTTTGCTGTAAAAGTGACAGAGA

CAAGTTGGCACGAAGTTTTATATGACATTGCACAGGATTGTGCATGGTGGACAATGTTTT

GTACAGCAGTGAATGCCTCTTCTTCAGAAGCATTCTTGGTTGGTGTTAATTATTTGGGTG

CAAGTGAAAAGGTTAAGGTTAGTGGAAAAACGCTGCACGCAAATTATATATTTTGGAGGA

ATTGTAATTATTTACAAACCTCTGCTTATAGTATATTTGACGTTGCTAAGTTTGATTTGA

GATTGAAAGCAACACCAGTTGTTAATTTGAAAACTGAACAAAAGAGAGACTTAGTGTTTA

ATTTAATTAAGTGTGGTAAGTTACTGGTAAGAGATGTTGGTAACACCTCTTTTACTAGTG

TACCAAAGTGCCTTTAGACCACCTAATGGTTGGCATTTACACGGGGGTGCTTATGCGGTA

GTTAATATTTCTAGCGAATCTAATAATGCAGGCTCTTCACCTGGGTGTATTGTTGGTACT

ATTCATGGTGGTCGTGTTGTTAATGCTTCTTCTATAGCTATGACGGCACCGTCATCAGGT

ATGGCTTGGTCTAGCAGTCAGTTTTGTACTGCACACTGTAACTTTTCAGATACTACAGTG

TTTGTTACACATTGTTATAAATATGATGGGTGTCCTATAACTGGCATGCTTCAAAAGAAT

TTTTTACGTGTTTCTGCTATGAAAAATGGCCAGCTTTTCTATAATTTAACAGTTAGTGTA

GCTAAGTACCCTACTTTTAAATCATTTCAGTGTGTTAATAATTTAACATCCGTATATTTA

AATGGTGATCTTGTTTACACCTCTAATGAGACCACAGATGTTACATCTGCAGGTGTTTAT
```

-continued

```
TTTAAAGCTGGTGGACCTATAACTTATAAAGTTATGAGAGAAGTTAAAGCCCTGGCTTAT

TTTGTTAATGGTACTGCACAAGATGTTATTTTGTGTGATGGATCACCTAGAGGCTTGTTA

GCATGCCAGTATAATACTGGCAATTTTTCAGATGGCTTTTATCCTTTTATTAATAGTAGT

TTAGTTAAGCAGAAGTTTATTGTCTATCGTGAAAATAGTGTTAATACTACTTTTACGTTA

CACAATTTCACTTTTCATAATGAGACTGGCGCCAACCCTAATCCTAGTGGTGTTCAGAAT

ATTCAAACTTACCAAACACAAACAGCTCAGAGTGGTTATTATAATTTTAATTTTTCCTTT

CTGAGTAGTTTTGTTTATAAGGAGTCTAATTTTATGTATGGATCTTATCACCCAAGTTGT

AATTTTAGACTAGAAACTATTAATAATGGCTTGTGGTTTAATTCACTTTCAGTTTCAATT

GCTTACGGTCCTCTTCAAGGTGGTTGCAAGCAATCTGTCTTTAGTGGTAGAGCAACTTGT

TGTTATGCTTATTCATATGGAGGTCCTTCGCTGTGTAAAGGTGTTTATTCAGGTGAGTTA

GATCTTAATTTTGAATGTGGACTGTTAGTTTATGTTACTAAGAGCGGTGGCTCTCGTATA

CAAACAGCCACTGAACCGCCAGTTATAACTCGACACAATTATAATAATATTACTTTAAAT

ACTTGTGTTGATTATAATATATATGGCAGAACTGGCCAAGGTTTTATTACTAATGTAACC

GACTCAGCTGTTAGTTATAATTATCTAGCAGACGCAGGTTTGGCTATTTTAGATACATCT

GGTTCCATAGACATCTTTGTTGTACAAGGTGAATATGGTCTTACTTATTATTAGGTTAAC

CCTTGCGAAGATGTCAACCAGCAGTTTGTAGTTTCTGGTGGTAAATTAGTAGGTATTCTT

ACTTCACGTAATGAGACTGGTTCTCAGCTTCTTGAGAACCAGTTTTACATTAAAATCACT

AATGGAACACGTCGTTTTAGACGTTCTATTACTGAAAATGTTGGAAATTGCCCTTATGTT

AGTTATGGTAAGTTTTGTATAAAACCTGATGGTTCAATTGCCACAATAGTACCAAAACAA

TTGGAACAGTTTGTGGCACCTTTACTTAATGTTACTGAAAATGTGCTCATACCTAACAGT

TTTAATTTAACTGTTACAGATGAGTACATACAAACGCGTATGGATAAGGTCCAAATTAAT

TGTCTGCAGTATGTTTGTGGCAATTCTCTGGATTGTAGAGATTTGTTTCAACAATATGGG

CCTGTTTGTGACAACATATTGTCTGTAGTAAATAGTATTGGTCAAAAAGAAGATATGGAA

CTTTTGAATTTCTATTCTTCTACTAAACCGGCTGGTTTTAATACACCATTTCTTAGTAAT

GTTAGCACTGGTGAGTTTAATATTTCTCTTCTGTTAACAACTCCTAGTAGTCCTAGAAGG

CGTTCTTTTATTGAAGACCTTCTATTTACAAGCGTTGAATCTGTTGGATTACCAACAGAT

GACGCATACAAAAATTGCACTGCAGGACCTTTAGGTTTTCTTAAGGACCTTGCGTGTGCT

CGTGAATATAATGGTTTGCTTGTGTTGCCTCCCATTATAACAGCAGAAATGCAAATTTTG

TATACTAGTTCTCTAGTAGCTTCTATGGCTTTTGGTGGTATTACTGCAGCTGGTGCTATA

CCTTTTGCCACACAACTGCAGGCTAGAATTAATCACTTGGGTATTACCCAGTCACTTTTG

TTGAAGAATCAAGAAAAAATTGCTGCTTCCTTTAATAAGGCCATTGGTCGTATGCAGGAA

GGTTTTAGAAGTACATCTCTAGCATTACAACAAATTCAAGATGTTGTTAATAAGCAGAGT

GCTATTCTTACTGAGACTATGGCATCACTTAATAAAAATTTTGGTGCTATTTCTTCTATG

ATTCAAGAAATCTACCAGCAACTTGACGCCATACAAGCAAATGCTCAAGTGGATCGTCTT

ATAACTGGTAGATTGTCATCACTTTCTGTTTTAGCATCTGCTAAGCAGGCGGAGCATATT

AGAGTGTCACAACAGCGTGAGTTAGCTACTCAGAAAATTAATGAGTGTGTTAAGTCACAG

TCTATTAGGTACTCCTTTTGTGGTAATGGACGACATGTTCTAACCATACCGCAAAATGCA

CCTAATGGTATAGTGTTTATACACTTTTCTTATACTCCAGATAGTTTTGTTAATGTTACT

GCAATAGTGGGTTTTTGTGTAAAGCCAGCTAATGCTAGTCAGTATGCAATAGTACCCGCT

AATGGTAGGGGTATTTTTATACAAGTTAATGGTAGTTACTACATCACAGCACGAGATATG

TATATGCCAAGAGCTATTACTGCAGGAGATATAGTTACGCTTACTTCTTGTCAAGCAAAT
```

-continued

```
TATGTAAGTGTAAATAAGACCGTCATTACTACATTCGTAGACAATGATGATTTTGATTTT

AATGACGAATTGTCAAAATGGTGGAATGACACTAAGCATGAGCTACCAGACTTTGACAAA

TTCAATTACACAGTACCTATACTTGACATTGATAGTGAAATTGATCGTATTCAAGGCGTT

ATACAGGGTCTTAATGACTCTTTAATAGACCTTGAAAAACTTTCAATACTCAAAACTTAT

ATTAAGTGGCCTTGGTATGTGTGGTTAGCCATAGCTTTTGCCACTATTATCTTCATCTTA

ATACTAGGATGGGTTTTCTTCATGACTGGATGTTGTGGTTGTTGTTGTGGATGCTTTGGC

ATTATGCCTCTAATGAGTAAGTGTGGTAAGAAATCTTCTTATTACACGACTTTTGATAAC

GATGTGGTAACTTAACAATACAGACCTAAAAAGTCTGTTTAATGATTCAAAGTCCCACGT

CCTTCCTAATAGTATTAATTTTTCTTTGGTGTAAACTTGTACTAAGTTGTTTTAGAGAGT

TTATTATAGCGCTCCAACAACTAATACAAGTTTTACTCCAAATTATCAATAGTAACTTAC

AGCCTAGACTGACCCTTTGTCACAGTCTAGACTAATGTTAAACTTAGAAGCAATTATTGA

AACTGGTGAGCAAGTGATTCAAAAAATCAGTTTCAATTTACAGCATATTTCAAGTGTATT

AAACACAGAAGTATTTGACCCCTTTGACTATTGTTATTACAGAGGAGGTAATTTTTGGGA

AATAGAGTCAGCTGAAGATTGTTCAGGTGATGATGAATTTATTGAATAAGTCGCTAGAGG

AAAATGGAAGTTTTCTAACAGCGCTTTATATATTTGTAGGATTTTTAGCACTTTATCTTC

TAGGTAGAGCACTTCAAGCATTTGTACAGGCTGCTGATGCTTGTTGTTTATTTTGGTATA

CATGGGTAGTAATTCCAGGAGCTAAGGGTACAGCCTTTGTATATAAGTATACATATGGTA

GAAAACTTAACAATCGGGAATTAGAAGCAGTTATTGTCAACGAGTTTCCTAAGAACGGTT

GGAATAATAAAAATCCAGCAAATTTTCAAGATGTCCAACGAGACAAATTGTACTCTTGAC

TTTGAACAGTCAGTTGAGCTTTTTAAAGAGTATAATTTATTTATAACTGCATTCTTGTTG

TTCTTAACCATAATACTTCAGTATGGCTATGCAACAAGAAGTAAGTTTATTTATATACTG

AAAATGATAGTGTTATGGTGCTTTTGGCCCCTTAACATTGCAGTAGGTGTAATTTCATGT

ATATACCCACCAAACACAGGAGGTCTTGTCGCAGCGATAATACTTACAGTGTTTGCGTGT

CTGTCTTTTGTAGGTTATTGGATCCAGAGTATTAGACTCTTTAAGCGGTGTAGGTCATGG

TGGTCATTTAACCCAGAATCTAATGCCGTAGGTTCAATACTCCTAACTAATGGTCAACAA

TGTAATTTTGCTATAGAGAGTGTGCCAATGGTGCTTTCTCCAATTATAAAGAATGGTGTT

CTTTATTGTGAGGGTCAGTGGCTTGCTAAGTGTGAACCAGACCACTTGCCTAAAGATATA

TTTGTTTGTACACCGGATAGACGTAATATCTACCGTATGGTGCAGAAATATACTGGTGAC

CAAAGCGGAAATAAGAAACGGTTTGCTACGTTTGTCTATGCAAAGCAGTCAGTAGATACT

GGCGAGCTAGAAAGTGTAGCAACAGGAGGGAGTAGTCTTTACACCTAAATGTGTGTGTGT

AGAGAGTATTTAAAATTATTCTTTAATAGTGCCTCTATTTTAAGAGCGCATAATAGTATT

ATTTTTGAGGATATTAATATAAATCCTCTCTGTTTTATACTCTCTTTTCAAGAGCTATTA

TTTAAAAAACAGTTTTTCCACTCTTTTGTGCCAAAAACTATTGTTGTTAATGGTGTAACC

TTTCAAGTAGATAATGGAAAAGTCTACTACGAAGGAAAACCAATTTTTCAGAAAGGTTGT

TGTAGGTTGTGGTTGAGTTATAAAAAAGATTAAACTACCTACTACACTTATTTTTATAAG

AGGCGTTTTATCTTACAAGCGCTTAATAAATACGGACGATGAAATGGCTGACTAGTTTTG

TAAGGGCAGTTATTTCATGTTATAAACCCCTATTATTAACTCAATTAAGAGTATTAGATA

GGTTAATCTTAGATCATGGACCAAAACACATCTTAACGTGTGTTAGGTGCGTGATTTTGT

TTCAATTAGATTTAGTTTATAGGTTGGCGTATACGCCTACTCAATCGCTGGTATGAATAA

TAGTAAAGATAATCCTTTTTGCGGAGCAATAGCAAGAAAAGCGCGAATTTATCTGAGAGA
```

```
-continued
AGGATTAGATTGTGTTTACTTTCTTAACAAAGCAGGACAAGCAGAGTCTTGTCCCGCGTG

TACCTCTCTAGTATTCCAGGGGAAAACTTGTGAGGAACACAAATATAATAATAATCTTTT

GTCATGGCAAGCGGTAAGGCAACTGGAAAGACAGATGCCCCAGCTCCAGTCATCAAACTA

GGAGGACCAAAGCCACCTAAAGTTGGTTCTTCTGGAAATGTATCTTGGTTTCAAGCAATA

AAAGCCAAGAAGTTAAATTCACCTCCGCCTAAGTTTGAAGGTAGCGGTGTTCCTGATAAT

GAAAATCTAAAACCAAGTCAGCAGCATGGATATTGGAGACGCCAAGCTAGGTTTAAGCCA

GGTAAAGGTGGAAGAAAACCAGTCCCAGATGCTTGGTATTTTTAGTATACTGGAACAGGA

CCAGCCGCTAACCTGAATTGGGGTGATAGCCAAGATGGTATAGTGTGGGTTGCTGGTAAG

GGTGCTGATACTAAATTTAGATCTAATCAGGGTACTCGTGACTCTGACAAGTTTGACCAA

TATCCGCTACGGTTTTCAGACGGAGGACCTGATGGTAATTTCCGTTGGGATTTCATTCCT

CTGAATCGTGGCAGGAGTGGGAGATCAACAGCAGCTTCATCAGCAGCATCTAGTAGAGCA

CCATCACGTGAAGTTTCGCGTGGTCGCAGGAGTGGTTCTGAAGATGATCTTATTGCTCGT

GCAGCAAGGATAATTCAGGATCAGCAGAAGAAGGGTTCTCGCATTACAAAGGCTAAGGCT

GATGAAATGGCTCACCGCCGGTATTGCAAGCGCAGTATTCCACCTAATTATAAGGTTGAT

CAAGTGTTTGGTCCCCGTACTAAAGGTAAGGAGGGAAATTTTGGTGATGACAAGATGAAT

GAGGAAGGTATTAAGGATGGGCGCGTTACAGCAATGCTCAACCTAGTTCCTAGCAGCCAT

GCTTGTCTTTTCGGAAGTAGAGTGACGCCCAGACTTCAACCAGATGGGCTGCACTTGAAA

TTTGAATTTACTACTGTGGTCCCACGTGATGATCCGCAGTTTGATAATTATGTAAAAATT

TGTGATCAGTGTGTTGATGGTGTAGGAACACGTCCAAAAGATGATGAACCAAGACCAAAG

TCACGCTCAAGTTCAAGACCTGCAACAAGAGGAAATTCTCCAGCGCCAAGACAGCAGCGC

CCTAAGAAGGAGAAAAAGCCAAAGAAGCAGGATGATGAAGTGGATAAAGCATTGACCTCA

GATGAGGAGAGGAACAATGCACAGCTGGAATTTGATGATGAACCCAAGGTAATTAACTGG

GGGGATTCAGCGCTAGGAGAGAATGAACTTTGAGTAAAATTGAATAGTAAGAGTTAAGGA

AGATAGGCATGTAGCTTGATTACCTACATGTCTATCGCCAGGGAAATGTCTAATTTGTCT

ACTTAGTAGCCTGGAAACGAACGGTAGACCCTTAGATTTTAATTTAGTTTAATTTTTAGT

TTAGTTTAAGTTAGTTTAGAGTAGGTATAAAGATGCCAGTGGCGGGGCCACGCGGAGTAC

GACCGAGGGTACAGCACTAGGACGCCCATTAGGGGAAGAGCTAAATTTTAGTTTAAGTTA

AGTTTAATTGGCTATGTATAGTTAAAATTTATAGGCTAGTATAGAGTTAGAGCAAAAAAA

AAAAAAAAAAAAAAAAAAAA
```

Replicase

In addition to the structural and accessory genes, two-thirds of a coronavirus genome comprises the replicase gene (at the 5' end of the genome), which is expressed as two polyproteins, pp1a and pp1ab, in which pp1ab is an extension product of pp1a as a result of a −1 ribosomal shift mechanism. The two polyproteins are cleaved by two types of virus-encoded proteinases usually resulting in 16 non-structural proteins (Nsp1-16); IBV lacks Nsp1 thereby encoding Nsp2-16.

Thus Gene 1 in IBV encodes 15 (16 in other coronaviruses) non-structural proteins (nsp2-16), which are associated with RNA replication and transcription.

The term 'replicase protein' is used herein to refer to the pp1a and pp1ab polyproteins or individual nsp subunits.

The term 'replicase gene' is used herein to refer to a nucleic acid sequence which encodes for replicase proteins.

A summary of the functions of coronavirus nsp proteins is provided in Table 1.

TABLE 1

| Nsp Protein | Key features |
|---|---|
| 1 | Conserved within but not between coronavirus genetic groups; potential regulatory functions in the host cell. |
| 2 | Dispensable for MHV and SARS-CoV replication in tissue culture |
| 3 | Acidic domain; macro domain with ADRP and poly (ADP-ribose)-binding activities; one or two ZBD-containing papain-like proteases; Y domain |
| 4 | Transmembrane domain |
| 5 | 3C-like main protease, homodimer |
| 6 | Transmembrane domain |
| 7 | Interacts with nsp8 to form a hexadecamer complex |
| 8 | Noncannonical RNA polymerase; interacts with nsp7 to form a hexadecameric complex |
| 9 | ssRNA-binding protein, dimer |
| 10 | RNA-binding protein, homododecamer, zinc-binding domain, known to interact with nsp14 and nsp16 |

TABLE 1-continued

| Nsp Protein | Key features |
|---|---|
| 11 | Unknown |
| 12 | RNA-dependent RNA polymerase |
| 13 | Zinc-binding domain, NTPase, dNTPase, 5'-to-3' RNA and DNA helicase, RNA 5'-triphosphate |
| 14 | 3'-to 5' exoribonuclease, zinc-binding domain and N7-methyltransferase |
| 15 | Uridylate-specific endoribonuclease, homohexamer |
| 16 | Putative ribose-2'-O-methyltransferase |

The variant replicase gene encoded by the coronavirus of the present invention comprises a mutation in one or more of the sections of sequence encoding nsp-10, nsp-14, nsp-15 or nsp-16.

Nsp10 has RNA-binding activity and appears to be involved in homo and/or heterotypic interactions within other nsps from the pp1a/pp1ab region. It adopts an α/β fold comprised of five α-helices, one $3_{10}$-helix and three β-strands. Two zinc-binding sites have been identified that are formed by conserved cysteine residues and one histidine residue (Cys-74/Cys-77/His-83/Cys-90; Cys-117/Cys-120/Cys-128/Cys-130). The protein has been confirmed to bind single-stranded and double-stranded RNA and DNA without obvious specificity. Nsp-10 can be cross-linked with nsp-9, suggesting the existing of a complex network of protein-protein interactions involving nsp-7, -8, -9 and -10. In addition, nsp-10 is known to interact with nsp-14 and nsp-16.

Nsp-14 comprises a 3'-to-5' exoribonuclease (ExoN) active domain in the amino-terminal region. SARS-CoV ExoN has been demonstrated to have metal ion-dependent 3'-to-5' exoribonuclease activity that acts on both single-stranded and double-stranded RNA, but not on DNA. Nsp-14 has been shown to have proof-reading activity. This nsp has also been shown to have N7-methyltransferase (MT) activity in the carboxyl-terminal region.

Nsp-15 associated NendoU (nidoviral endoribonuclease, specific for U) RNase activity has been reported for a number of coronaviruses, including SARS-CoV, MHV and IBV. The activities were consistently reported to be significantly enhanced by $Mn^{2+}$ ions and there was little activity in the presence of $Mg^{2+}$ and $Ca^{2+}$. NendoU cleaves at the 3' side of uridylate residues in both single-stranded and double-stranded RNA. The biologically relevant substrate(s) of coronavirus NendoUs remains to be identified.

Nsp-16 has been predicted to mediate ribose-2'-O-methyltransferase (2'-O-MTase) activity and reverse-genetics experiments have shown that the 2'-O-MTase domain is essential for viral RNA synthesis in HCoV-229E and SARS-CoV. The enzyme may be involved in the production of the cap 1 structures of coronavirus RNAs and it may also cooperate with NendoU and ExoN in other RNA processing pathways. 2'-O-MTase might also methylate specific RNAs to protect them from NendoU-mediated cleavage.

The genomic and protein sequences for nsp-10, -14, -15 and -16 are provided as SEQ ID NO: 2-5 and 6-9, respectively.

```
(nsp-10 nucleotide sequence- nucleotides 11884-12318 of SEQ ID NO: 1)
                                                          SEQ ID NO: 2
TCTAAAGGTCATGAGACAGAGGAAGTGGATGCTGTAGGCATTCTCTCACTTTGTTCTTTTGCAGTA

GATCCTGCGGATACATATTGTAAATATGTGGCAGCAGGTAATCAACCTTTAGGTAACTGTGTTAAA

ATGTTGACAGTACATAATGGTAGTGGTTTTGCAATAACATCAAAGCCAAGTCCAACTCCGGATCAG

GATTCTTATGGAGGAGCTTCTGTGTGTCTTTATTGTAGAGCACATATAGCACACCTTGGCGGAGCA

GGAAATTTAGATGGACGCTGTCAATTTAAAGGTTCTTTTGTGCAAATACCTACTACGGAGAAAGAT

CCTGTTGGATTCTGTCTACGTAACAAGGTTTGCACTGTTTGTCAGTGTTGGATTGGTTATGGATGT

CAGTGTGATTCACTTAGACAACCTAAACCTTCTGTTCAG (nsp-14 nucleotide sequence- nucleotides 16938-18500 of SEQ ID NO: 1)
                                                          SEQ ID NO: 3
GGTACAGGCTTGTTTAAAATTTGCAACAAAGAGTTTAGTGGTGTTCACCCAGCTTATGCAGTCACA

ACTAAGGCTCTTGCTGCAACTTATAAAGTTAATGATGAACTTGCTGCACTTGTTAACGTGGAAGCT

GGTTCAGAAATAACATATAAACATCTTATTTCTTTGTTAGGGTTTAAGATGAGTGTTAATGTTGAA

GGCTGCCACAACATGTTTATAACACGTGATGAGGCTATCCGCAACGTAAGAGGTTGGGTAGGTTTT

GATGTAGAAGCAACACATGCTTGCGGTACTAACATTGGTACTAACCTGCCTTTCCAAGTAGGTTTC

TCTACTGGTGCAGACTTTGTAGTTACGCCTGAGGGACTTGTAGATACTTCAATAGGCAATAATTTT

GAGCCTGTGAATTCTAAAGCACCTCCAGGTGAACAATTTAATCACTTGAGAGCGTTATTCAAAAGT

GCTAAACCTTGGCATGTTGTAAGGCCAAGGATTGTGCAAATGTTAGCGGATAACCTGTGCAACGTT

TCAGATTGTGTAGTGTTTGTCACGTGGTGTCATGGCCTAGAACTAACCACTTTGCGCTATTTTGTT

AAAATAGGCAAGGACCAAGTTTGTTCTTGCGGTTCTAGAGCAACAACTTTTAATTCTCATACTCAG

GCTTATGCTTGTTGGAAGCATTGCTTGGGTTTTGATTTTGTTTATAATCCACTCTTAGTGGATATT

CAACAGTGGGGTTATTCTGGTAACCTACAATTTAACCATGATTTGCATTGTAATGTGCATGGACAC

GCACATGTAGCTTCTGCGGATGCTATTATGACGCGTTGTCTTGCAATTAATAATGCATTTTGTCAA
```

-continued

```
GATGTCAACTGGGATTTAACTTACCCTCATATAGCAAATGAGGATGAAGTCAATTCTAGCTGTAGA

TATTTACAACGCATGTATCTTAATGCATGTTGATGCTCTTAAAGTTAACGTTGTCTATGATATA

GGCAACCCTAAAGGTATTAAATGTGTTAGACGTGGAGACTTAAATTTTAGATTCTATGATAAGAAT

CCAATAGTACCCAATGTCAAGCAGTTTGAGTATGACTATAATCAGCACAAAGATAAGTTTGCTGAT

GGTCTTTGTATGTTTTGGAATTGTAATGTGGATTGTTATCCCGACAATTCCTTACTTTGTAGGTAC

GACACACGAAATTTGAGTGTGTTTAACCTACCTGGTTGTAATGGTGGTAGCTTGTATGTTAACAAG

CATGCATTCCACACACCTAAATTTGATCGCACTAGCTTTCGTAATTTGAAAGCTATGCCATTCTTT

TTCTATGACTCATCGCCTTGCGAGACCATTCAATTGGATGGAGTTGCGCAAGACCTTGTGTCATTA

GCTACGAAAGATTGTATCACAAAATGCAACATAGGCGGTGCTGTTTGTAAAAAGCACGCACAAATG

TATGCAGATTTTGTGACTTCTTATAATGCAGCTGTTACTGCTGGTTTTACTTTTTGGGTTACTAAT

AATTTTAACCCATATAATTTGTGGAAAAGTTTTTCAGCTCTCCAG (nsp-15 nucleotide sequence- nucleotides 18501-19514 of SEQ ID NO: 1)
                                                        SEQ ID NO: 4
TCTATCGACAATATTGCTTATAATATGTATAAGGGTGGTCATTATGATGCTATTGCAGGAGAAATG

CCCACTATCGTAACTGGAGATAAAGTTTTTGTTATAGATCAAGGCGTAGAAAAAGCAGTTTTTTTT

AATCAAACAATTCTGCCTACATCTGTAGCGTTTGAGCTGTATGCGAAGAGAAATATTCGCACACTG

CCAAACAACCGTATTTTGAAAGGTTTGGGTGTAGATGTGACTAATGGATTTGTAATTTGGGATTAC

ACGAACCAAACACCACTATACCGTAATACTGTTAAGGTATGTGCATATACAGACATAGAACCAAAT

GGCCTAATAGTGCTGTATGATGATAGATATGGTGATTACCAGTCTTTTCTAGCTGCTGATAATGCT

GTTTTAGTTTCTACACAGTGTTACAAGCGGTATTCGTATGTAGAAATACCGTCAAACCTGCTTGTT

CAGAACGGTATTCCGTTAAAAGATGGAGCGAACCTGTATGTTTATAAGCGTGTTAATGGTGCGTTT

GTTACGCTACCTAACACAATAAACACACAGGGTCGAAGTTATGAAACTTTTGAACCTCGTAGTGAT

GTTGAGCGTGATTTTCTCGACATGTCTGAGGAGAGTTTTGTAGAAAAGTATGGTAAAGAATTAGGT

CTACAGCACATACTGTATGGTGAAGTTGATAAGCCCCAATTAGGTGGTTTCCACACTGTTATAGGT

ATGTGCAGACTTTTACGTGCGAATAAGTTGAACGCAAAGTCTGTTACTAATTCTGATTCTGATGTC

ATGCAAAATTATTTTGTATTGGCAGACAATGGTTCCTACAAGCAAGTGTGTACTGTTGTGGATTTG

CTGCTTGATGATTTCTTAGAACTTCTTAGGAACATACTGAAAGAGTATGGTACTAATAAGTCTAAA

GTTGTAACAGTGTCAATTGATTACCATAGCATAAATTTTATGACTTGGTTTGAAGATGGCATTATT

AAAACATGTTATCCACAGCTTCAA (nsp-16 nucleotide sequence- nucleotides 19515-20423 of SEQ ID NO: 1)
                                                        SEQ ID NO: 5
TCAGCATGGACGTGTGGTTATAATATGCCTGAACTTTATAAAGTTCAGAATTGTGTTATGGAACCT

TGCAACATTCCTAATTATGGTGTTGGAATAGCGTTGCCAAGTGGTATTATGATGAATGTGGCAAAG

TATACACAACTCTGTCAATACCTTTCGAAAACAACAATGTGTGTACCGCATAATATGCGAGTAATG

CATTTTGGAGCTGGAAGTGACAAAGGAGTGGTGCCAGGTAGTACTGTTCTTAAACAATGGCTCCCA

GAAGGGACACTCCTTGTCGATAATGATATTGTAGACTATGTGTCTGATGCACATGTTTCTGTGCTT

TCAGATTGCAATAAATATAAGACAGAGCACAAGTTTGATCTTGTGATATCTGATATGTATACAGAC

AATGATTCAAAAAGAAAGCATGAAGGCGTGATAGCCAATAATGGCAATGATGACGTTTTCATATAT

CTCTCAAGTTTTCTTCGTAATAATTTGGCTCTAGGTGGTAGTTTTGCTGTAAAAGTGACAGAGACA

AGTTGGCACGAAGTTTTATATGACATTGCACAGGATTGTGCATGGTGGACAATGTTTTGTACAGCA

GTGAATGCCTCTTCTTCAGAAGCATTCTTGATTGGTGTTAATTATTTGGGTGCAAGTGAAAAGGTT

AAGGTTAGTGGAAAAACGCTGCACGCAAATTATATATTTTGGAGGAATTGTAATTATTTACAAACC
```

```
-continued
TCTGCTTATAGTATATTTGACGTTGCTAAGTTTGATTTGAGATTGAAAGCAACGCCAGTTGTTAAT

TTGAAAACTGAACAAAAGACAGACTTAGTCTTTAATTTAATTAAGTGTGGTAAGTTACTGGTAAGA

GATGTTGGTAACACCTCTTTTACTAGTGACTCTTTTGTGTGTACTATGTAG (nsp-10 amino acid sequence)
                                                            SEQ ID NO: 6
SKGHETEEVDAVGILSLCSFAVDPADTYCKYVAAGNQPLGNCVKMLTVKNGSGFAITSKPSPTPDQ

DSYGGASVCLYCRAHIAHPGGAGNLDGRCQFKGSFVQIPTTEKDPVGFCLRNKVCTVCQCWIGYGC

QCDSLRQPKPSVQ (nsp-14 amino acid sequence)
                                                            SEQ ID NO: 7
GTGLFKICNKEFSGVHPAYAVTTKALAATYKVNDELAALVNVEAGSEITYKHLISLLGFKMSVNVE

GCHNMFITRDEAIRNVRGWVGFDVEATHACGTNIGTNLPFQVGFSTGADFVVTPEGLVDTSIGNNF

EPVNSKAPPGEQFNHLRALFKSAKPWHVVRPRIVQMLADNLCNVSDCVVFVTWCHGLELTTLRYFV

KIGKDQVCSCGSRATTFNSHTQAYACWKHCLGFDFVYNPLLVDIQQWGYSGNLQFNHDLHCNVHGH

AHVASADAIMTRCLAINNAFCQDVNWDLTYPHIANEDEVNSSCRYLQRMYLNACVDALKVNVVYDI

GNPKGIKCVRRGDLNFRFYDKNPIVPNVKQFEYDYNQHKDKFADGLCMFWNCNVDCYPDNSLVCRY

DTRNLSVFNLPGCNGGSLYVNKHAFHTPKFDRTSFRNLKAMPFFFYDSSPCETIQLDGVAQDLVSL

ATKDCITKCNICGAVCKKKAQMYADFVTSYNAAVTAGFTPWVTNNFNPYNLWKSFSALQ (nsp-15 amino acid sequence)
                                                            SEQ ID NO: 8
SIDNIAYNMYKGGHYDAIAGEMPTIVTGDKVFVIDQGVEKAVFFNQTILPTSVAFELYAKRNIRTL

PNNRILKGLGVDVTNGFVIWDYTNQTPLYRNTVKVCAYTDIEPNGLIVLYDDRYGDYQSFLAADNA

VLVSTQCYKRYSYVEIPSNLLVQNGIPLKDGANLYVYKRVNGAFVTLPNTLNTQGRSYETFEPRSD

VERDFLDMSEESFVEKYGKELGLQHILYGEVDKPQLGGLHTVIGMCRLLRANKLNAKSVTNSDSDV

MQNYFVLADNGSYKQVCTVVDLLLDDFLELLRNILKEYGTNKSKVVTVSIDYHSINFMTWFEDGII

KTCYPQLQ (nsp-16 amino acid sequence)
                                                            SEQ ID NO: 9
SAWTCGYNMPELYKVQNCVMEPCNIPNYGVGIALPSGIMMNVAKYTQLCQYLSKTTMCVPHNMRVM

HFGAGSDKGVAPGSTVLKQWLPEGTLLVDNDIVDYVSDAHVSVLSDCNKYKTEHKFDLVISDMYTD

NDSKRKHEGVIANNGNDDVFIYLSSFLRNNLALGGSFAVKVTETSWHEVLYDIAQDCAWWTMFCTA

VNASSSEAFLVGVNYLGASEKVIWSGKTLHANYIFWRNCNYLQTSAYSIFDVAKFDLRLKATPVVN

LKTEQKTDLVFNLIKCGKLLVRDVGNTSFTSDSFVCTM
```

Reduced Pathogenicity

The live, attenuated coronavirus of the present invention comprises a variant replicase gene which causes the virus to have reduced pathogenicity compared to a coronavirus expressing the corresponding wild-type gene.

The term "attenuated" as used herein, refers to a virus that exhibits said reduced pathogenicity and may be classified as non-virulent. A live, attenuated virus is a weakened replicating virus still capable of stimulating an immune response and producing immunity but not causing the actual illness.

The term "pathogenicity" is used herein according to its normal meaning to refer to the potential of the virus to cause disease in a subject. Typically the pathogenicity of a coronavirus is determined by assaying disease associated symptoms, for example sneezing, snicking and reduction in tracheal ciliary activity.

The term "reduced pathogenicity" is used to describe that the level of pathogenicity of a coronavirus is decreased, lessened or diminished compared to a corresponding, wild-type coronavirus.

In one embodiment, the coronavirus of the present invention has a reduced pathogenicity compared to the parental M41-CK virus from which it was derived or a control coronavirus. The control coronavirus may be a coronavirus with a known pathogenicity, for example a coronavirus expressing the wild-type replicase protein.

The pathogenicity of a coronavirus may be assessed utilising methods well-known in the art. Typically, pathogenicity is assessed by assaying clinical symptoms in a subject challenged with the virus, for example a chicken.

As an illustration, the chicken may be challenged at 8-24 days old by nasal or ocular inoculation. Clinical symptoms, associated with IBV infection, may be assessed 3-10 days post-infection. Clinical symptoms commonly assessed to determine the pathogenicity of a coronavirus, for example an IBV, include gasping, coughing, sneezing, snicking, depression, ruffled feathers and loss of tracheal ciliary activity.

The variant replicase of the present invention, when expressed in a coronavirus, may cause a reduced level of clinical symptoms compared to a coronavirus expressing a wild-type replicase.

For example a coronavirus expressing the variant replicase may cause a number of snicks per bird per minute which is less than 90%, less than 80%, less than 70%, less than 60%, less than 50%, less than 40%, less than 30%, less than 20% or less than 10% of the number of snicks caused by a virus expressing the wild type replicase.

A coronavirus expressing a variant replicase according to the present invention may cause wheezing in less than 70%, less than 60%, less than 50%, less than 40%, less than 30%, less than 20% or less than 10% of the number of birds in a flock infected with the a virus expressing the wild type replicase.

A coronavirus expressing a variant replicase according to the present invention may result in tracheal ciliary activity which is at least 60%, at least 70%, at least 80%, at least 90% or at least 95% of the level of tracheal ciliary activity in uninfected birds.

A coronavirus expressing a variant replicase according to the present invention may cause clinical symptoms, as defined in Table 2, at a lower level than a coronavirus expressing the wild type replicase.

levels when administered to broiler chickens with maternal antibodies as these strains are neutralized by the maternal antibody pool.

Thus a viral particle must be sufficiently efficient at replicating and propagating to ensure that it is not neutralized by the maternally-derived antibodies against the virus. Maternally-derived antibodies are a finite pool of effective antibodies, which decrease as the chicken ages, and neutralization of the virus in this manner does not equate to the establishment of long-term immunity for the embryo/chick. In order to develop long-term immunity against the virus, the embryo and hatched chicken must develop an appropriate protective immune response which is distinct to the effect of the maternally-derived antibodies.

To be useful for in ovo vaccination, the virus must also not replicate and propagate at a level which causes it to be pathogenic to the embryo.

Reduced pathogenicity in terms of the embryo may mean that the coronavirus causes less reduction in hatchability compared to a corresponding, wild-type control coronavirus. Thus the term "without being pathogenic to the embryo" in the context of the present invention may mean "without causing reduced hatchability" when compared to a control coronavirus.

A suitable variant replicase may be identified using methods which are known in the art. For example comparative challenge experiments following in ovo vaccination of

TABLE 2

| IBV severity limits based on clinical signs: |  |
| --- | --- |
| Snicking (sneezing)<br>Nasal exudate<br>Watery eyes<br>Swollen infraorbital sinuses<br>Rales (vibration in trachea or bronchi region) | IBV specific: Mild (N.B. Respiratory signs become apparent from 2-3 dpi if they are going to occur and can continue for up to 7d). |
| Hunched posture/depressed<br>Fluffed up feathers<br>Eating and drinking less | Mild, if exceed 2d increase to moderate |
| Drinking in excess: evident by fluid filled crop or measured water intake | IBV specific: Mild, if exceed 24h increase to moderate for a max of 2d. If still drinking in excess then kill by schedule 1 method. |
| Less active but still evade capture<br>Weight loss<br>Not eating or drinking | Mild, if exceed 1d increase to moderate. |
| Birds sit alone and does not evade capture<br>Severe respiratory distress: e.g. excessive gasping<br>Snicking and/or rales for 7d in total | Moderate: birds at end point. Kill by schedule 1 method. |
| Found dead | Severe: report to project license holder. Full post-mortem to be performed. |

The variant replicase of the present invention, when expressed in a coronavirus, may cause the virus to replicate at non-pathogenic levels in ovo.

While developing vaccines to be administered in ovo to chicken embryos, attention must be paid to two points: the effect of maternal antibodies on the vaccines and the effect of the vaccines on the embryo. Maternal antibodies are known to interfere with active immunization. For example, vaccines with mild strains do not induce protective antibody embryos with or without maternally-derived antibodies may be performed (i.e. wherein the layer has or has not been vaccinated against IBV).

If the variant replicase enables the virus to propagate at a level which is too high, the embryo will not hatch or will not be viable following hatching (i.e. the virus is pathogenic to the embryo). A virus which is pathogenic to the embryo may kill the embryo.

If the variant replicase causes a reduction in viral replication and propagation which is too great, the virus will be neutralised by the maternally-derived antibodies. Subsequent challenge of the chick with IBV will therefore result in the development of clinical symptoms (for example wheezing, snicking, loss of ciliary activity) and the onset of disease in the challenged chick; as it will have failed to develop effective immunity against the virus.

Variant

As used herein, the term 'variant' is synonymous with 'mutant' and refers to a nucleic acid or amino acid sequence which differs in comparison to the corresponding wild-type sequence.

A variant/mutant sequence may arise naturally, or may be created artificially (for example by site-directed mutagenesis). The mutant may have at least 70, 80, 90, 95, 98 or 99% sequence identity with the corresponding portion of the wild type sequence. The mutant may have less than 20, 10, 5, 4, 3, 2 or 1 mutation(s) over the corresponding portion of the wild-type sequence.

The term "wild type" is used to mean a gene or protein having a nucleotide or amino acid sequence which is identical with the native gene or protein respectively (i.e. the viral gene or protein).

Identity comparisons can be conducted by eye, or more usually, with the aid of readily available sequence comparison programs. These commercially available computer programs can calculate % identity between two or more sequences. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools, ClustalX (see Larkin et al. (2007) Clustal W and Clustal X version 2.0. Bioinformatics, 23:2947-2948). Both BLAST and FASTA are available for offline and online searching (see Ausubel et al., 1999 ibid, pages 7-58 to 7-60). However, for some applications, it is preferred to use the GCG Bestf it program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

The sequence may have one or more deletions, insertions or substitutions of amino acid residues which produce a silent change and result in a functionally equivalent molecule. Deliberate amino acid substitutions may be made on the basis of similarity in polarity, charge, solubility, hydrophobicity, hydrophilicity, and/or the amphipathic nature of the residues as long as the activity is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar- uncharged | C S T M |
| | | N Q |
| | Polar- charged | D E |
| | | K R |
| AROMATIC | | H F W Y |

The coronavirus of the present invention may comprise a variant replicase gene which encodes a protein which comprises a mutation compared to any one of SEQ ID NO: 6, 7, 8 or 9 which, when expressed in a coronavirus, causes the virus to have reduced pathogenicity compared to a coronavirus expressing the corresponding wild-type replicase.

The variant replicase gene may encode a protein which comprises at least one or more amino acid mutations in any combination of nsp-10, nsp-14, nsp-15 and nsp-16.

Figure 10:
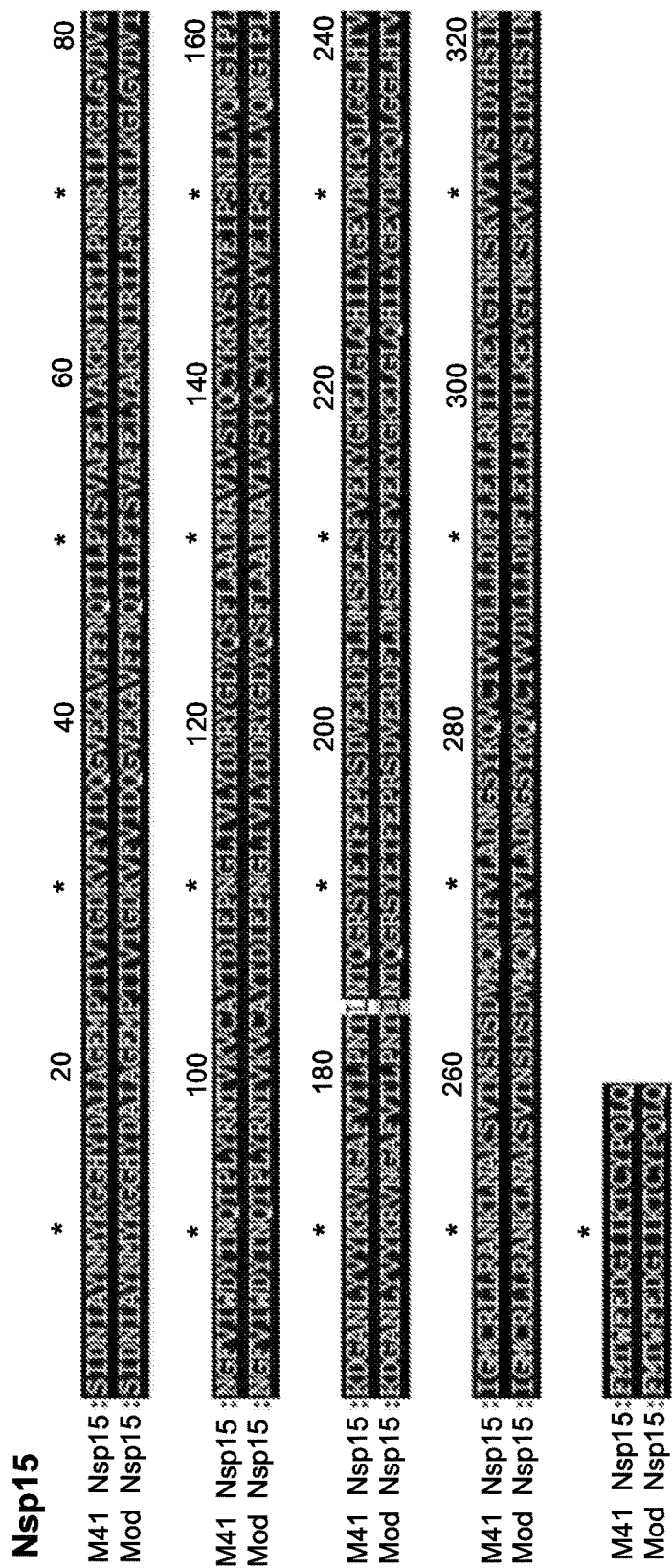
FIG. 10—Position of amino acid mutations in mutated nsp10, nsp14, nsp15 and nsp16 sequences.
Figure 10:
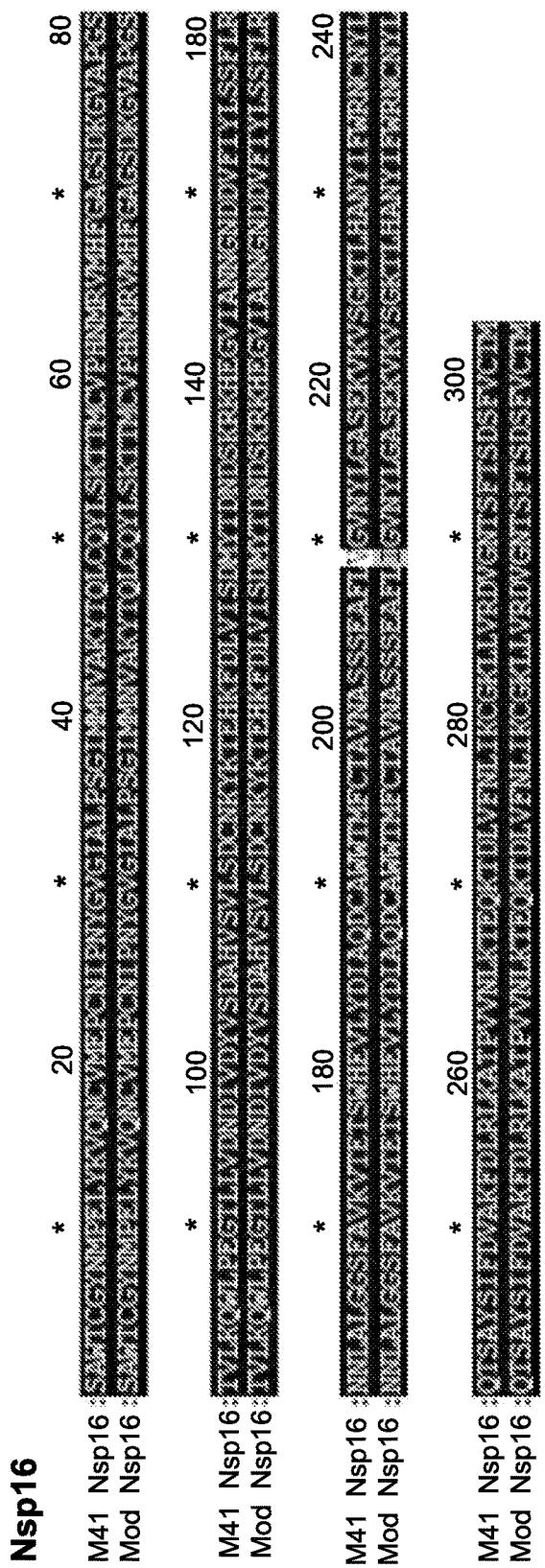

The variant replicase gene of the coronavirus of the present invention may encode a protein comprising a mutation as defined in the M41 mod sequences presented in FIG. 10.

The variant replicase gene of the coronavirus of the present invention may encode a protein which comprises one or more amino acid mutations selected from the list of:
Pro to Leu at position 85 of SEQ ID NO: 6,
Val to Leu at position 393 of SEQ ID NO: 7;
Leu to Ile at position 183 of SEQ ID NO: 8;
Val to Ile at position 209 of SEQ ID NO: 9.

The variant replicase gene of the coronavirus of the present invention may encode a protein which does not comprise a mutation in nsp-2, nsp-3, nsp-6 or nsp-13.

The variant replicase gene of the coronavirus of the present invention may encode a protein which does not comprise a mutation in nsp10 which corresponds to the threonine to isoleucine mutation caused by a mutation at nucleotide position 12,008 in the gene reported by Ammayappan et al. (Arch Virol (2009) 154:495-499).

Ammayappan et al (as above) reports the identification of sequence changes responsible for the attenuation of IBV strain Arkansas DPI. The study identified 17 amino acid changes in a variety of IBV proteins following multiple passages, approx. 100, of the virus in embryonated eggs. It was not investigated whether the attenuated virus (Ark DPI 101) is capable of replicating in the presence of maternally-derived antibodies against the virus in ovo, without being pathogenic to the embryo. Given that this virus was produced by multiple passage in SPF embryonated eggs, similar methodology for classical IBV vaccines, it is likely that this virus is pathogenic for embryos. The virus may also be sensitive to maternally-derived antibodies if the hens were vaccinated with a similar serotype.

The variant replicase gene of the coronavirus of the present invention may encode a protein which comprises any combination of one or more amino acid mutations provided in the list above.

The variant replicase gene may encode a protein which comprises the amino acid mutation Pro to Leu at position 85 of SEQ ID NO: 6.

The variant replicase gene may encode a protein which comprises the amino acid mutation Val to Leu at position 393 of SEQ ID NO: 7.

The variant replicase gene may encode a protein which comprises the amino acid mutation Leu to Ile at position 183 of SEQ ID NO: 8.

The variant replicase gene may encode a protein which comprises the amino acid mutation Val to Ile at position 209 of SEQ ID NO: 9.

The variant replicase gene may encode a protein which comprises the amino acid mutations Pro to Leu at position 85 of SEQ ID NO: 6, and Val to Leu at position 393 of SEQ ID NO: 7.

The variant replicase gene may encode a protein which comprises the amino acid mutations Pro to Leu at position 85 of SEQ ID NO: 6 Leu to Ile at position 183 of SEQ ID NO: 8.

The variant replicase gene may encode a protein which comprises the amino acid mutations Pro to Leu at position 85 of SEQ ID NO: 6 and Val to Ile at position 209 of SEQ ID NO: 9.

The variant replicase gene may encode a protein which comprises the amino acid mutations Val to Leu at position 393 of SEQ ID NO: 7 and Leu to Ile at position 183 of SEQ ID NO: 8.

The variant replicase gene may encode a protein which comprises the amino acid mutations Val to Leu at position 393 of SEQ ID NO: 7 and Val to Ile at position 209 of SEQ ID NO: 9.

The variant replicase gene may encode a protein which comprises the amino acid mutations Leu to Ile at position 183 of SEQ ID NO: 8 and Val to Ile at position 209 of SEQ ID NO: 9.

The variant replicase gene may encode a protein which comprises the amino acid mutations Pro to Leu at position 85 of SEQ ID NO: 6, Val to Leu at position 393 of SEQ ID NO: 7 and Leu to Ile at position 183 of SEQ ID NO: 8.

The variant replicase gene may encode a protein which comprises the amino acid mutations Pro to Leu at position 85 of SEQ ID NO: 6 Leu to Ile at position 183 of SEQ ID NO: 8 and Val to Ile at position 209 of SEQ ID NO: 9.

The variant replicase gene may encode a protein which comprises the amino acid mutations Pro to Leu at position 85 of SEQ ID NO: 6, Val to Leu at position 393 of SEQ ID NO: 7 and Val to Ile at position 209 of SEQ ID NO: 9.

The variant replicase gene may encode a protein which comprises the amino acid mutations Val to Leu at position 393 of SEQ ID NO: 7, Leu to Ile at position 183 of SEQ ID NO: 8 and Val to Ile at position 209 of SEQ ID NO: 9.

The variant replicase gene may encode a protein which comprises the amino acid mutations Pro to Leu at position 85 of SEQ ID NO: 6, Val to Leu at position 393 of SEQ ID NO: 7, Leu to Ile at position 183 of SEQ ID NO: 8 and Val to Ile at position 209 of SEQ ID NO: 9.

The variant replicase gene may also be defined at the nucleotide level.

For example the nucleotide sequence of the variant replicase gene of the coronavirus of the present invention may comprise one or more nucleotide substitutions within the regions selected from the list of: 11884-12318, 16938-18500, 18501-19514 and 19515-20423 of SEQ ID NO:1.

For example the nucleotide sequence of the variant replicase gene of the coronavirus of the present invention may comprise one or more nucleotide substitutions selected from the list of:

C to Tat nucleotide position 12137;
G to C at nucleotide position 18114;
T to A at nucleotide position 19047; and
G to A at nucleotide position 20139;

compared to the sequence shown as SEQ ID NO: 1.

As used herein, the term "substitution" is synonymous with the term mutation and means that the nucleotide at the identified position differs to that of the wild-type nucleotide sequence.

The nucleotide sequence may comprise any combination of the nucleotide substitutions selected from the list of:

C to Tat nucleotide position 12137;
G to Cat nucleotide position 18114;
T to A at nucleotide position 19047; and
G to A at nucleotide position 20139;

compared to the sequence shown as SEQ ID NO: 1.

The nucleotide sequence may comprise the substitution C12137T.

The nucleotide sequence may comprise substitution G18114C.

The nucleotide sequence may comprise the substitution T19047A.

The nucleotide sequence may comprise the substitution G20139A.

The nucleotide sequence may comprise the substitutions C12137T and G18114C.

The nucleotide sequence may comprise the substitutions C12137T and T19047A.

The nucleotide sequence may comprise the substitutions C12137T and G20139A.

The nucleotide sequence may comprise the substitutions G18114C and T19047A.

The nucleotide sequence may comprise the substitutions G18114C and G20139A.

The nucleotide sequence may comprise the substitutions T19047A and G20139A.

The nucleotide sequence may comprise the substitutions C12137T, G18114C and T19047A.

The nucleotide sequence may comprise the substitutions C12137T, T19047A and G20139A.

The nucleotide sequence may comprise the substitutions C12137T, G18114C and G20139A.

The nucleotide sequence may comprise the substitutions G18114C, T19047A and G20139A.

The nucleotide sequence may comprise the substitutions C12137T, G18114C, T19047A and G20139A.

The nucleotide sequence may not comprise a substitution which corresponds to the C12008T substitution reported by Ammayappan et al. (as above).

The nucleotide sequence may be natural, synthetic or recombinant. It may be double or single stranded, it may be DNA or RNA or combinations thereof. It may, for example, be cDNA, PCR product, genomic sequence or mRNA.

The nucleotide sequence may be codon optimised for production in the host/host cell of choice.

It may be isolated, or as part of a plasmid, virus or host cell.

Plasmid

A plasmid is an extra-chromosomal DNA molecule separate from the chromosomal DNA which is capable of replicating independently of the chromosomal DNA. They are usually circular and double-stranded.

Plasmids, or vectors (as they are sometimes known), may be used to express a protein in a host cell. For example a bacterial host cell may be transfected with a plasmid capable of encoding a particular protein, in order to express that protein. The term also includes yeast artificial chromosomes and bacterial artificial chromosomes which are capable of accommodating longer portions of DNA.

The plasmid of the present invention comprises a nucleotide sequence capable of encoding a defined region of the replicase protein. It may also comprise one or more additional coronavirus nucleotide sequence(s), or nucleotide sequence(s) capable of encoding one or more other coronavirus proteins such as the S gene and/or gene 3.

The plasmid may also comprise a resistance marker, such as the guanine xanthine phosphoribosyltransferase gene (gpt) from *Escherichia coli*, which confers resistance to mycophenolic acid (MPA) in the presence of xanthine and hypoxanthine and is controlled by the vaccinia virus P7.5 early/late promoter.

Recombinant Vaccinia Virus

The present invention also relates to a recombinant vaccinia virus (rVV) comprising a variant replicase gene as defined herein.

The recombinant vaccinia virus (rVV) may be made using a vaccinia-virus based reverse genetics system.

In this respect, the present invention also provides a method for making a viral particle by:
(i) transfecting a plasmid as described in the previous section into a host cell;
(ii) infecting the host cell with a recombining virus comprising the genome of a coronavirus strain with a replicase gene;
(iii) allowing homologous recombination to occur between the replicase gene sequences in the plasmid and the corresponding sequences in the recombining virus genome to produce a modified replicase gene;
(iv) selecting for recombining virus comprising the modified replicase gene.

The term 'modified replicase gene' refers to a replicase gene which comprises a variant replicase gene as described in connection with the first aspect of the present invention. Specifically, the term refers to a gene which is derived from a wild-type replicase gene but comprises a nucleotide sequence which causes it to encode a variant replicase protein as defined herein.

The recombination may involve all or part of the replicase gene. For example the recombination may involve a nucleotide sequence encoding for any combination of nsp-10, nsp-14, nsp-15 and/or nsp-16. The recombination may involve a nucleotide sequence which encodes for an amino acid mutation or comprises a nucleotide substitution as defined above.

The genome of the coronavirus strain may lack the part of the replicase protein corresponding to the part provided by the plasmid, so that a modified protein is formed through insertion of the nucleotide sequence provided by the plasmid.

The recombining virus is one suitable to allow homologous recombination between its genome and the plasmid. The vaccinia virus is particularly suitable as homologous recombination is routinely used to insert and delete sequences for the vaccinia virus genome.

The above method optionally includes the step:
(v) recovery of recombinant coronavirus comprising the modified replicase gene from the DNA from the recombining virus from step (iv).

Methods for recovering recombinant coronavirus, such as recombinant IBV, are known in the art (See Britton et al (2005) see page 24; and PCT/GB2010/001293).

For example, the DNA from the recombining virus from step (iv) may be inserted into a plasmid and used to transfect cells which express cytoplasmic T7 RNA polymerase. The cells may, for example be pre-infected with a fowlpox virus expressing T7 RNA polymerase. Recombinant coronavirus may then be isolated, for example, from the growth medium.

When the plasmid is inserted into the vaccinia virus genome, an unstable intermediate is formed. Recombinants comprising the plasmid may be selected for e.g. using a resistance marker on the plasmid.

Positive recombinants may then be verified to contain the modified replicase gene by, for example, PCR and sequencing.

Large stocks of the recombining virus including the modified replicase gene (e.g. recombinant vaccinia virus, (rVV) may be grown up and the DNA extracted in order to carry out step (v)).

Suitable reverse genetics systems are known in the art (Casais et al (2001) J. Virol 75:12359-12369; Casais et al (2003) J. Virol. 77:9084-9089; Britton et al (2005) J. Virological Methods 123:203-211; Armesto et al (2008) Methods in Molecular Biology 454:255-273).

Cell

The coronavirus may be used to infect a cell.

Coronavirus particles may be harvested, for example from the supernatant, by methods known in the art, and optionally purified.

The cell may be used to produce the coronavirus particle.

Thus the present invention also provides a method for producing a coronavirus which comprises the following steps:
(i) infection of a cell with a coronavirus according to the invention;
(ii) allowing the virus to replicate in the cell; and
(iii) harvesting the progeny virus.

The present invention also provides a cell capable of producing a coronavirus according to the invention using a reverse genetics system. For example, the cell may comprise a recombining virus genome comprising a nucleotide sequence capable of encoding the replicase gene of the present invention.

The cell may be able to produce recombinant recombining virus (e.g. vaccinia virus) containing the replicase gene.

Alternatively the cell may be capable of producing recombinant coronavirus by a reverse genetics system. The cell may express or be induced to express T7 polymerase in order to rescue the recombinant viral particle.

Vaccine

The coronavirus may be used to produce a vaccine. The vaccine may by a live attenuated form of the coronavirus of the present invention and may further comprise a pharmaceutically acceptable carrier. As defined herein, "pharmaceutically acceptable carriers" suitable for use in the invention are well known to those of skill in the art. Such carriers include, without limitation, water, saline, buffered saline, phosphate buffer, alcohol/aqueous solutions, emulsions or suspensions. Other conventionally employed diluents and excipients may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, histidine-Hel, carbonic acid, tartaric acid, succinic acid, acetic acid, or phthalic acid, Iris, trimethanmine hydrochloride, or phosphate buffers. Parenteral carriers can include sodium chloride solution, Ringer's dextrose, dextrose, trehalose, sucrose, and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents (e.g., EDTA), inert gases and the like may also be provided in the pharmaceutical carriers. The present invention is not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, pub!., 2000; and The Handbook of Pharmaceutical Excipients, 4.sup.th edit., eds. R. C. Rowe et al, APhA Publications, 2003.

The vaccine of the invention will be administered in a "therapeutically effective amount", which refers to an amount of an active ingredient, e.g., an agent according to the invention, sufficient to effect beneficial or desired results when administered to a subject or patient. An effective amount can be administered in one or more administrations, applications or dosages. A therapeutically effective amount of a composition according to the invention may be readily determined by one of ordinary skill in the art. In the context of this invention, a "therapeutically effective amount" is one that produces an objectively measured change in one or more parameters associated Infectious Bronchitis condition sufficient to effect beneficial or desired results. An effective amount can be administered in one or more administrations. For purposes of this invention, an effective amount of drug, compound, or pharmaceutical composition is an amount sufficient to reduce the incidence of Infectious Bronchitis. As used herein, the term "therapeutic" encompasses the full spectrum of treatments for a disease, condition or disorder. A "therapeutic" agent of the invention may act in a manner that is prophylactic or preventive, including those that incorporate procedures designed to target animals that can be identified as being at risk (pharmacogenetics); or in a manner that is ameliorative or curative in nature; or may act to slow the rate or extent of the progression of at least one symptom of a disease or disorder being treated.

The present invention also relates to a method for producing such a vaccine which comprises the step of infecting cells, for example Vero cells, with a viral particle comprising a replicase protein as defined in connection with the first aspect of the invention.

Vaccination Method

The coronavirus of the present invention may be used to treat and/or prevent a disease.

To "treat" means to administer the vaccine to a subject having an existing disease in order to lessen, reduce or improve at least one symptom associated with the disease and/or to slow down, reduce or block the progression of the disease.

To "prevent" means to administer the vaccine to a subject who has not yet contracted the disease and/or who is not showing any symptoms of the disease to prevent or impair the cause of the disease (e.g. infection) or to reduce or prevent development of at least one symptom associated with the disease.

The disease may be any disease caused by a coronavirus, such as a respiratory disease and and/or gastroenteritis in humans and hepatitis, gastroenteritis, encephalitis, or a respiratory disease in other animals.

The disease may be infectious bronchitis (IB); Porcine epidemic diarrhoea; Transmissible gastroenteritis; Mouse hepatitis virus; Porcine haemagglutinating encephalomyelitis; Severe acute respiratory syndrome (SARS); or Bluecomb disease.

The disease may be infectious bronchitis.

The vaccine may be administered to hatched chicks or chickens, for example by eye drop or intranasal administration. Although accurate, these methods can be expensive e.g. for large broiler flocks. Alternatives include spray inoculation of administration to drinking water but it can be difficult to ensure uniform vaccine application using such methods.

The vaccine may be provided in a form suitable for its administration, such as an eye-dropper for intra-ocular use.

The vaccine may be administered by in ovo inoculation, for example by injection of embryonated eggs. In ovo vaccination has the advantage that it provides an early stage resistance to the disease. It also facilitates the administration of a uniform dose per subject, unlike spray inoculation and administration via drinking water.

The vaccine may be administered to any suitable compartment of the egg, including allantoic fluid, yolk sac, amnion, air cell or embryo. It may be administered below the shell (aircell) membrane and chorioallantoic membrane.

Usually the vaccine is injected into embryonated eggs during late stages of embryonic development, generally during the final quarter of the incubation period, such as 3-4 days prior to hatch. In chickens, the vaccine may be administered between day 15-19 of the 21-day incubation period, for example at day 17 or 18.

The process can be automated using a robotic injection process, such as those described in WO 2004/078203.

The vaccine may be administered together with one or more other vaccines, for example, vaccines for other diseases, such as Newcastle disease virus (NDV). The present invention also provides a vaccine composition comprising a vaccine according to the invention together with one or more other vaccine(s). The present invention also provides a kit comprising a vaccine according to the invention together with one or more other vaccine(s) for separate, sequential or simultaneous administration.

The vaccine or vaccine composition of the invention may be used to treat a human, animal or avian subject. For example, the subject may be a chick, chicken or mouse (such as a laboratory mouse, e.g. transgenic mouse).

Typically, a physician or veterinarian will determine the actual dosage which will be most suitable for an individual subject or group of subjects and it will vary with the age, weight and response of the particular subject(s).

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the delivery or immunogenicity of the virus.

The invention will now be further described by way of Examples, which are meant to serve to assist one of ordinary skill in the art in carrying out the invention and are not intended in any way to limit the scope of the invention.

EXAMPLES

Example 1—Generation of an IBV Reverse Genetics System Based on M41-CK

A M41-CK full-length cDNA was produced by replacement of the Beaudette cDNA in the Vaccinia virus reverse genetics system previously described in PCT/GB2010/001293 (herein incorporated by reference) with synthetic cDNA derived from the M41 consensus sequence.

The IBV cDNA within recombinant Vaccinia virus (rVV) rVV-BeauR-Rep-M41 structure described in Armesto, Cavanagh and Britton (2009). PLoS ONE 4(10): e7384. doi:10.1371/journal.pone.0007384, which consisted of the replicase derived from IBV Beaudette strain and the structural and accessory genes and 3' UTR from IBV M41-CK, was further modified by replacement of the Beaudette 5' UTR-Nsp2-Nsp3 sequence with the corresponding sequence from IBV M41-CK. The resulting IBV cDNA consisted of 5' UTR-Nsp2-Nsp3 from M41, Nsp4-Nsp16 from Beaudette and the structural and accessory genes and 3' UTR from M41. This cDNA was further modified by the deletion of the Beaudette Nsp4-Nsp16 sequence. The resulting cDNA, lacking Nsp4-16, was modified in four further steps in which the deleted Nsps were sequentially replaced with the corresponding sequences from M41-CK, the replacement cDNAs represented M41-CK Nsp4-8, Nsp9-12, Nsp12-14 and finally Nsp15-16. Each replacement cDNA contained approx. 500 nucleotides at the 5' end corresponding to the 3' most M41 sequence previously inserted and approx. 500 nucleotides at the 3' end corresponding to the M41 S gene sequence. This allowed insertion of the M41 cDNA sequence by homologous recombination and sequential addition of contiguous M41 replicase gene sequence. The synthetic cDNAs containing the M41-derived Nsp sequences were added by homologous recombination utilising the inventor's previous described transient dominant selection (IDS) system (see PCT/GB2010/001293). The M41-derived cDNAs containing sequence corresponding to the M41 Nsps-10, -14, -15 and -16 contained the modified amino acids at positions 85, 393, 183 and 209, respectively, as indicated in FIG. 10.

A full-length cDNA representing the genome of M41-CK was generated in Vaccinia virus representing the synthetic sequences. Two rIBVs, M41-R-6 and M41-R-12, were rescued and shown to grow in a similar manner as M41-CK (FIG. 1).

Example 2—Determining the Pathogenicity of Rescued M41 Viruses

Figure 2:
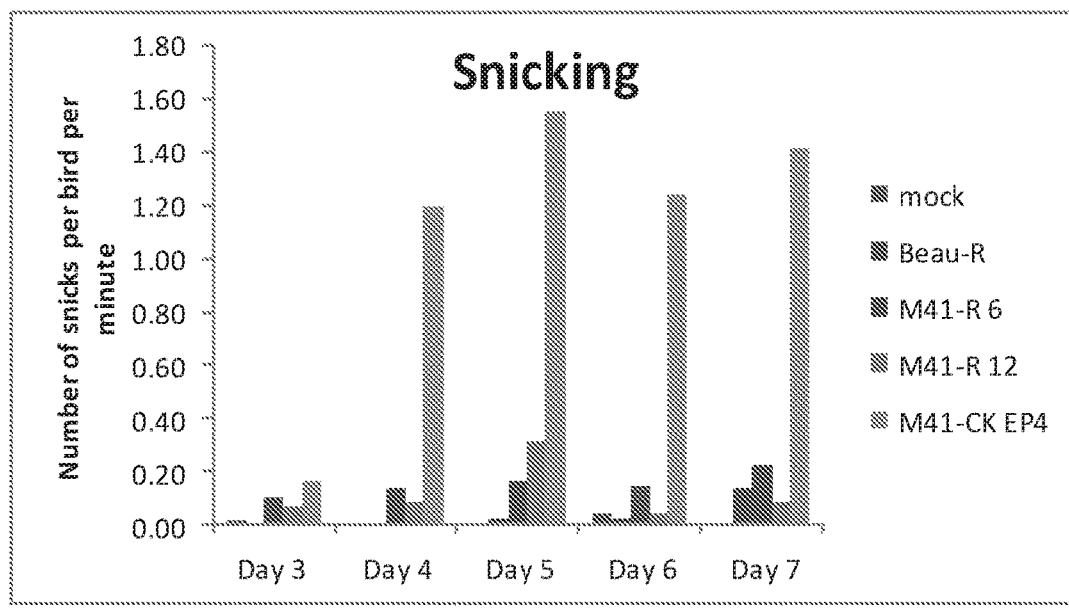
Figure 2:
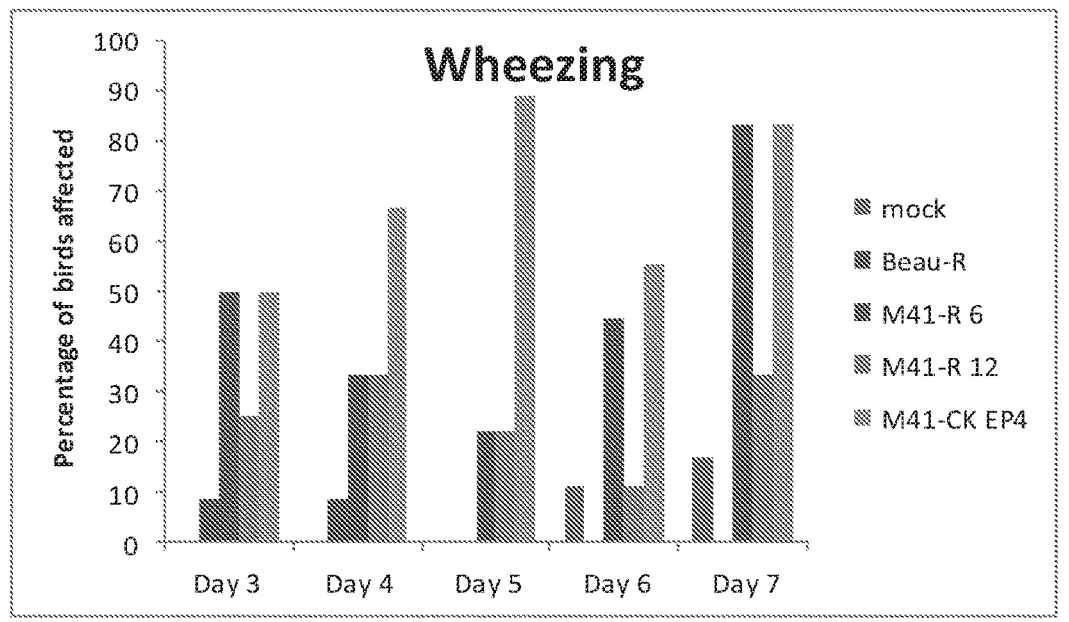
Figure 3:
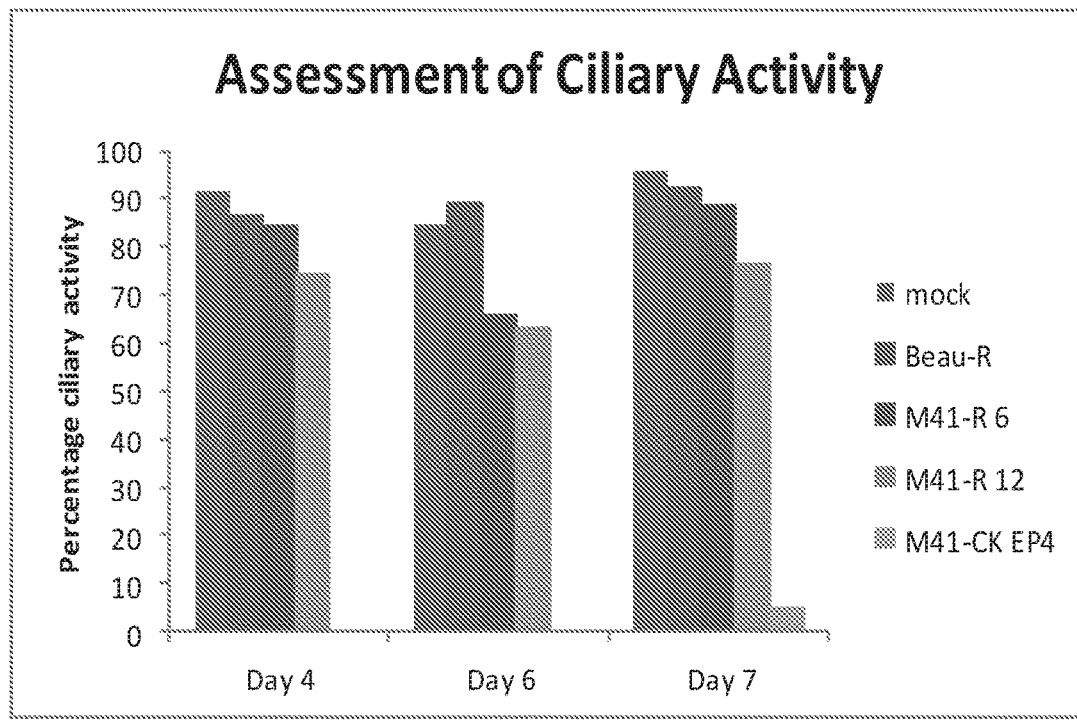
FIG. 3—Ciliary activity of the viruses in tracheal rings isolated from tracheas taken from infected chicks. 100% ciliary activity indicates no effect by the virus; apathogenic, 0% activity indicates complete loss of ciliary activity, complete ciliostasis, indicating the virus is pathogenic (Bars show mock, Beau-R, M41-R 6, M41-R 12, M41-CK EP4 from left to right of each timepoint).

The viruses rescued in Example 1 were used to infect 8-day-old specific pathogen free (SPF) chicks by ocular and nasal inoculation to test them for pathogenicity, as observed by clinical signs on a daily basis 3-7 days post-infection and for ciliary activity days 4 and 6 post-infection. Loss of ciliary activity is a well-established method for determining the pathogenicity of IBV. The two M41-R viruses were found to be apathogenic when compared to M41-CK though they did show some clinical signs in comparison to uninfected control chicks (FIG. 2) and some but inconsistent loss in ciliary activity (FIG. 3).

Thus, the M41-R molecular clones of M41-CK were not pathogenic when compared to the parental virus M41-CK.

The inventors identified several nucleotide differences in the M41-R compared to the M41-CK sequences. The majority of these were synonymous mutations, as the nucleotide change did not affect the amino acid sequence of the protein associated with the sequence. However, four non-synonymous mutations were identified in the IBV replicase gene specific to Nsp-10, Nsp-14, Nsp-15 and Nsp-16 components of the replicase gene, these mutations resulted in amino acid changes (Table 3).

TABLE 3

Non-Synonymous mutations identified in the Nsps of M41-R full-length genome

| Region of Replicase | Nucleotide position | Nucleotide Mutation | Amino Acid Change |
|---|---|---|---|
| Nsp10 | 12137 | C→T | Pro→Leu |
| Nsp14 | 18114 | G→C | Val→Leu |
| Nsp15 | 19047 | T→A | Leu→Ile |
| Nsp16 | 20139 | G→A | Val→Ile |

Example 3—Repair of M41-R rIBVs

Figure 9:
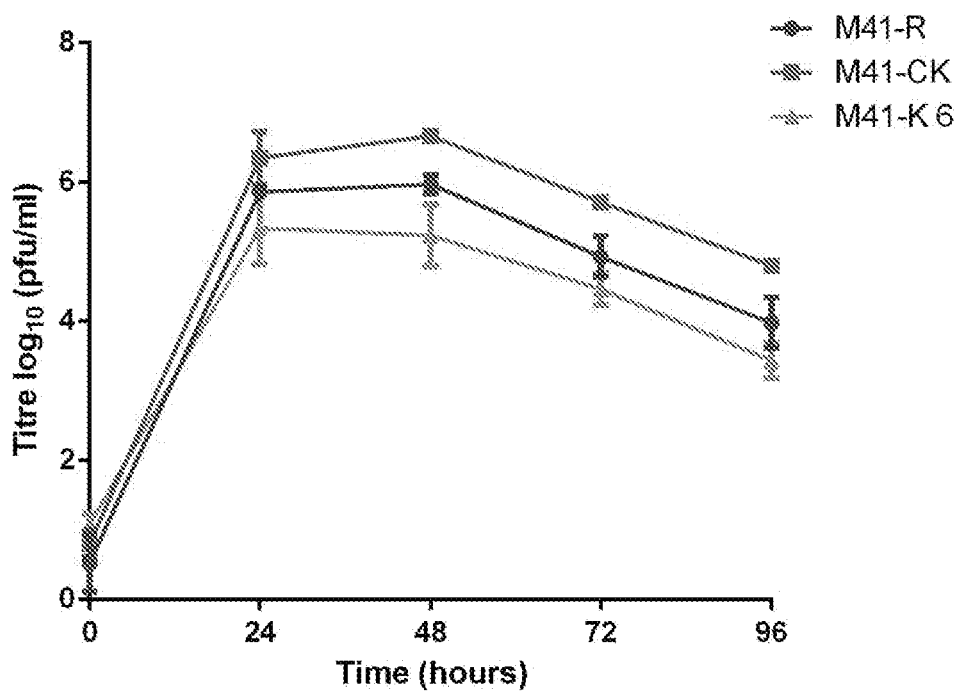
FIG. 9—Growth kinetics of rIBVs compared to M41-CK on CK cells.
Figure 9:
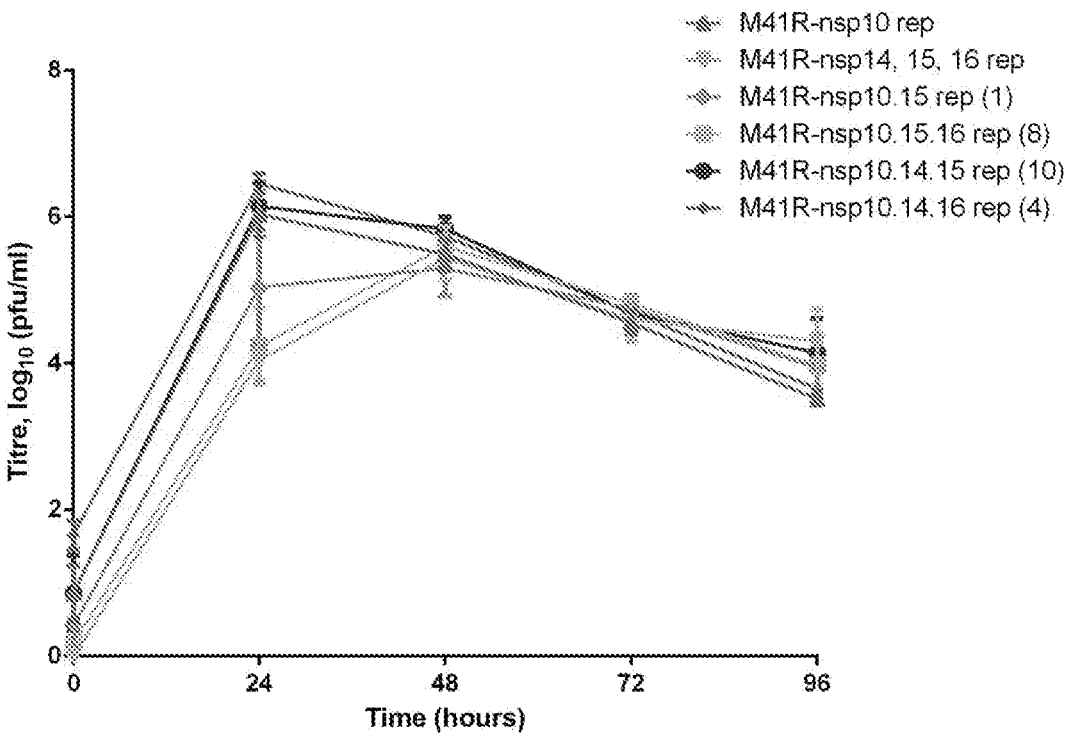

In order to determine whether the identified mutations were responsible for the loss of pathogenicity associated with M41-R, the Nsp10 mutation was repaired and the mutations in Nsp-14, -15 & -16 were repaired and shown to grow in a similar manner as M41-CK (FIG. 9). The inventors thus generated the rIBVs, M41R-nsp10rep and M41R-nsp14, 15, 16rep, using synthetic cDNAs containing the correct nucleotides utilising the inventor's previous described (TDS) system (see PCT/GB2010/001293).

Figure 4:
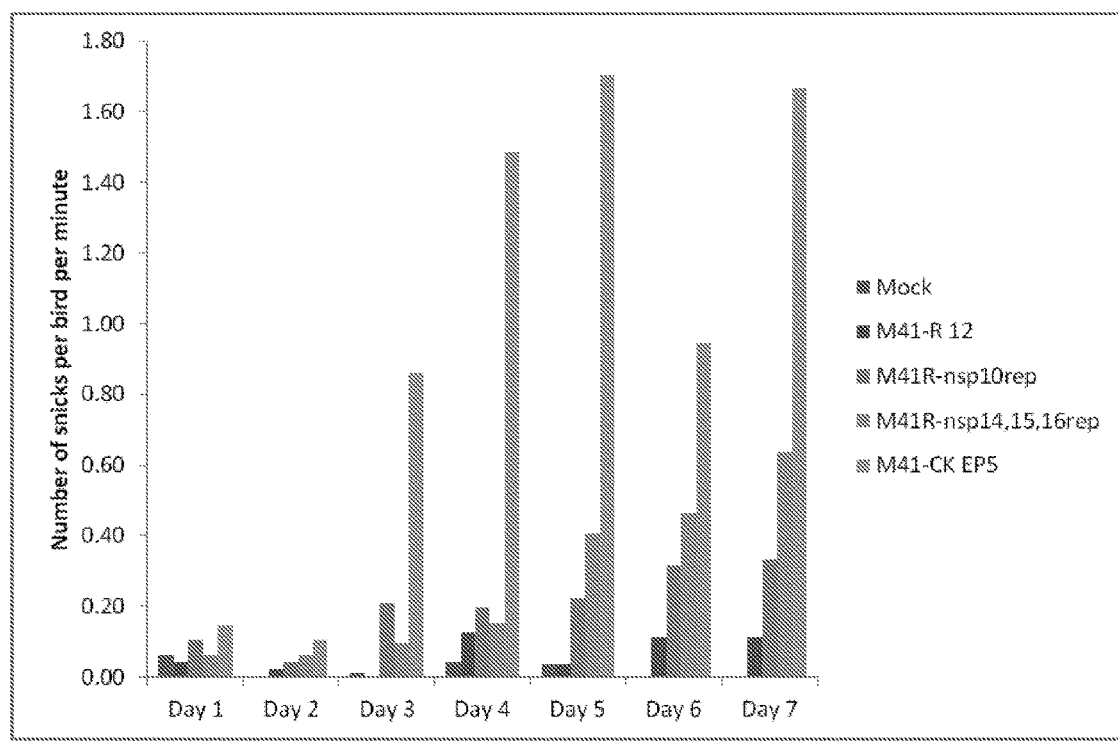
FIG. 4—Clinical signs, snicking, associated with M41R-nsp10rep and M41R-nsp14,15,16rep compared to M41-R-12 and M41-CK (M41 EP5) (Bars show mock, M41-R12; M41R-nsp10rep; M41R-nsp14,15,16rep and M41-CK EP5 from left to right of each timepoint).
Figure 5:
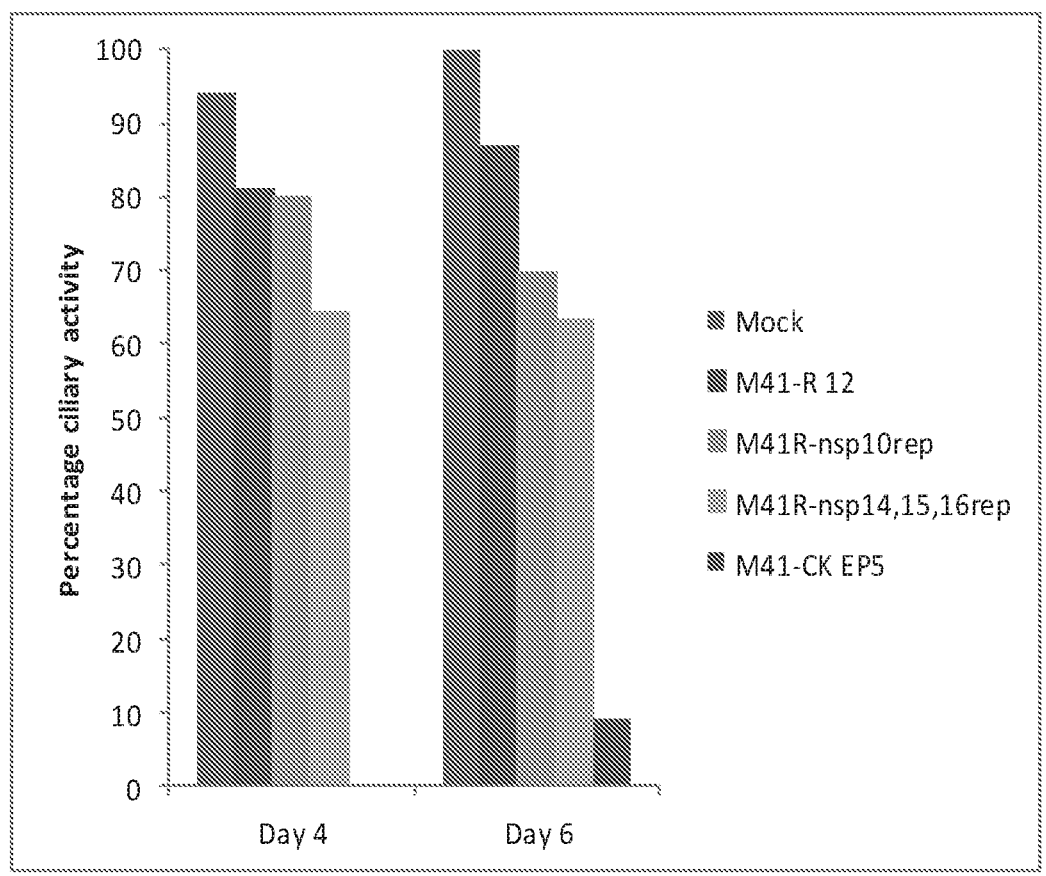
FIG. 5—Ciliary activity of M41R-nsp10rep and M41R-nsp14,15,16rep compared to M41-R-12 and M41-CK in tracheal rings isolated from tracheas taken from infected chicks (Bars show mock; M41-R12; M41R-nsp10rep; M41R-nsp14,15,16rep and M41-CK EP5 from left to right of each timepoint).

The rIBVs were assessed for pathogenicity in chicks as described previously. Both rIBVs showed increased pathogenicity when compared to M41-R but not to the level observed with M41-CK (FIGS. 4 and 5). M41R-nsp14, 15, 16rep gave more clinical signs and more reduction in ciliary activity than M41R-nsp10rep, overall these results indicated that the changes associated with the four Nsps appear to affect pathogenicity.

To determine the roles of the Nsps in pathogenicity the full-length cDNA corresponding to M41R-nsp10rep was used to repair the mutations in Nsps14, 15 & 16 using a synthetic cDNA containing the correct nucleotides utilising the TDS system.

The following rIBVs were produced:

M41R-nsp10, 15rep—M41-R with the mutations in Nsp-10 and Nsp-15 repaired

M41R-nsp10, 14, 15rep—M41-R with mutations in Nsp-10, -14 and -15 repaired

M41R-nsp10, 14, 16rep—M41-R with mutations in Nsp-10, -14 and -16 repaired

M41R-nsp10, 15, 16rep—M41-R with mutations in Nsp-10, -15 and -16 repaired

M41-K—All four mutations, Nsp-10, -14, -15 & -16 repaired in M41-R

Figure 6:
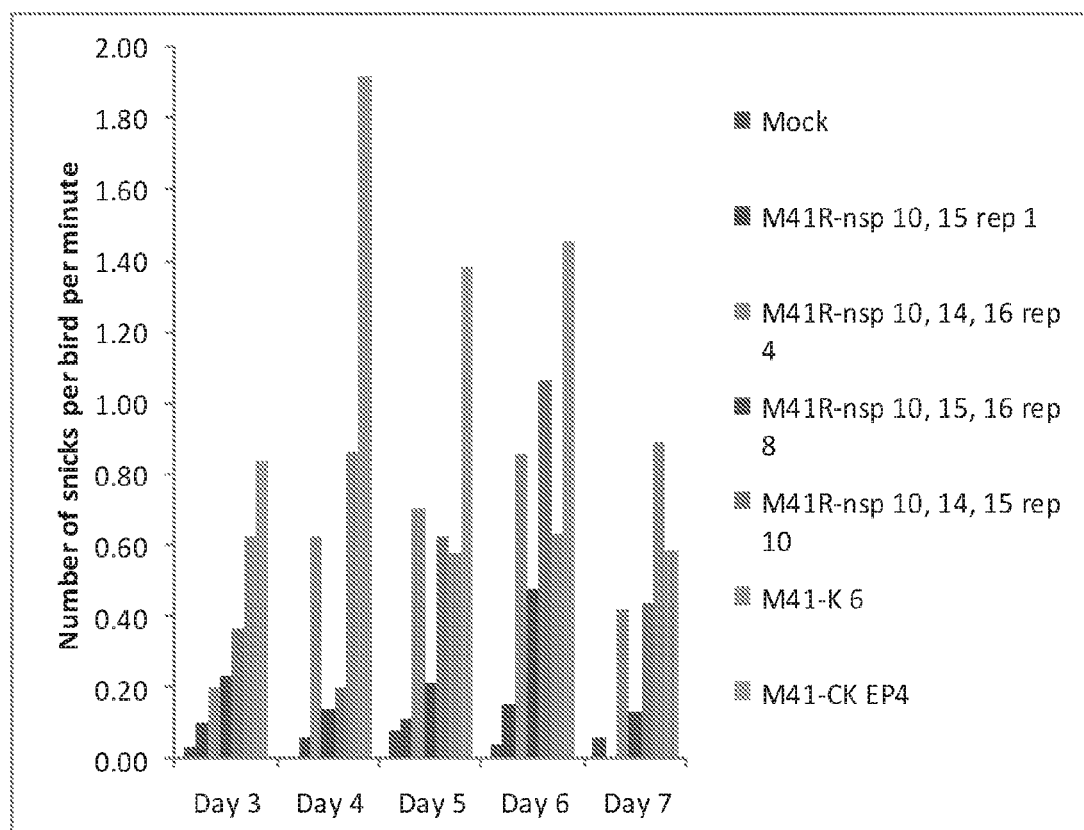
FIG. 6—Clinical signs, snicking, associated with M41R-nsp10, 15rep, M41R-nsp10, 14, 15rep, M41R-nsp10, 14, 16rep, M41R-nsp10, 15, 16rep and M41-K compared to M41-CK (Bars show mock, M41R-nsp10,15rep1; M41R-nsp10,14,16rep4; M41R-nsp10,15,16rep8; M41R-nsp10,14,15rep10; M41-K6 and M41-CK EP4 from left to right of each timepoint).
Figure 7:
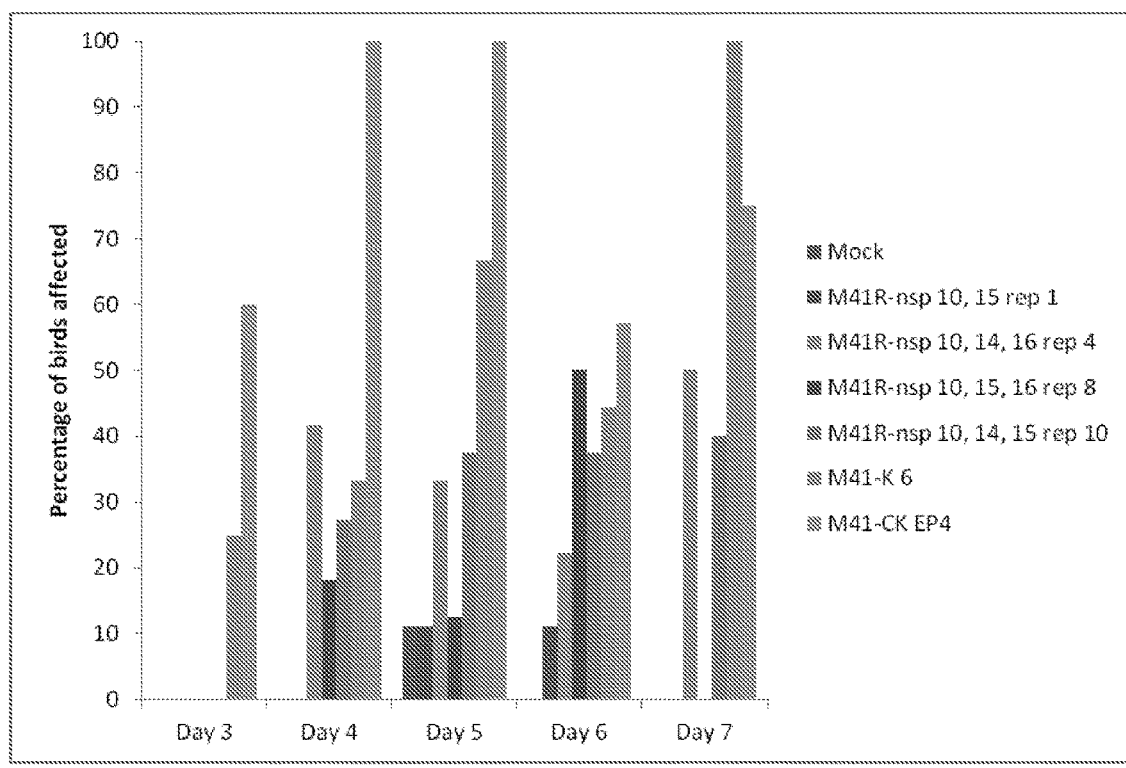
FIG. 7—Clinical signs, wheezing, associated with M41R-nsp10, 15rep, M41R-nsp10, 14, 15rep, M41R-nsp10, 14, 16rep, M41R-nsp10, 15, 16rep and M41-K compared to M41-CK (Bars show mock, M41R-nsp10,15rep1; Ml4R-nsp10,14,16rep4; M41R-nsp10,15,16rep8; M41R-nsp10,14,15rep10; M41-K6 and M41-CK EP4 from left to right of each timepoint).
Figure 8:
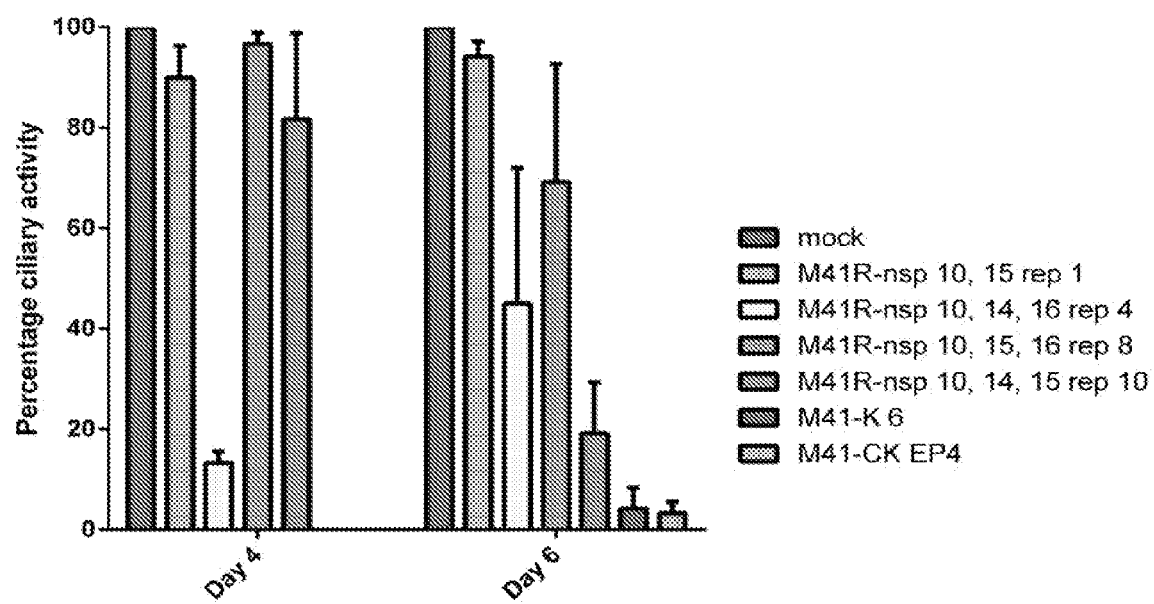
FIG. 8—Ciliary activity of M41R-nsp10, 15rep, M41R-nsp10, 14, 15rep, M41R-nsp10, 14, 16rep, M41R-nsp10, 15, 16rep and M41-K compared to M41-CK in tracheal rings isolated from tracheas taken from infected chicks (Bars show mock, M41R-nsp10,15rep1; M41R-nsp10,14,16rep4; M41R-nsp10,15,16rep8; M41R-nsp10,14,15rep10; M41-K6 and M41-CK EP4 from left to right of each timepoint).

The rIBVs were shown to grow in a similar manner as M41-CK (FIG. 9) and assessed for pathogenicity as described previously. M41-K (in which all four mutations had been repaired) resulted in clinical signs and 100% loss of ciliary activity (complete ciliostasis) by 4 days post-infection (FIGS. 6, 7 & 8). The other rIBVs demonstrated varying levels of pathogenicity, apart from M41R-nsp10, 15, 16rep, which was essentially apathogenic. These results confirmed that repair of all four Nsps restored pathogenicity to M41-R; again supporting the previous evidence that the mutations described in the four Nsps are implicated in attenuating M41-CK.

Figure 11C:
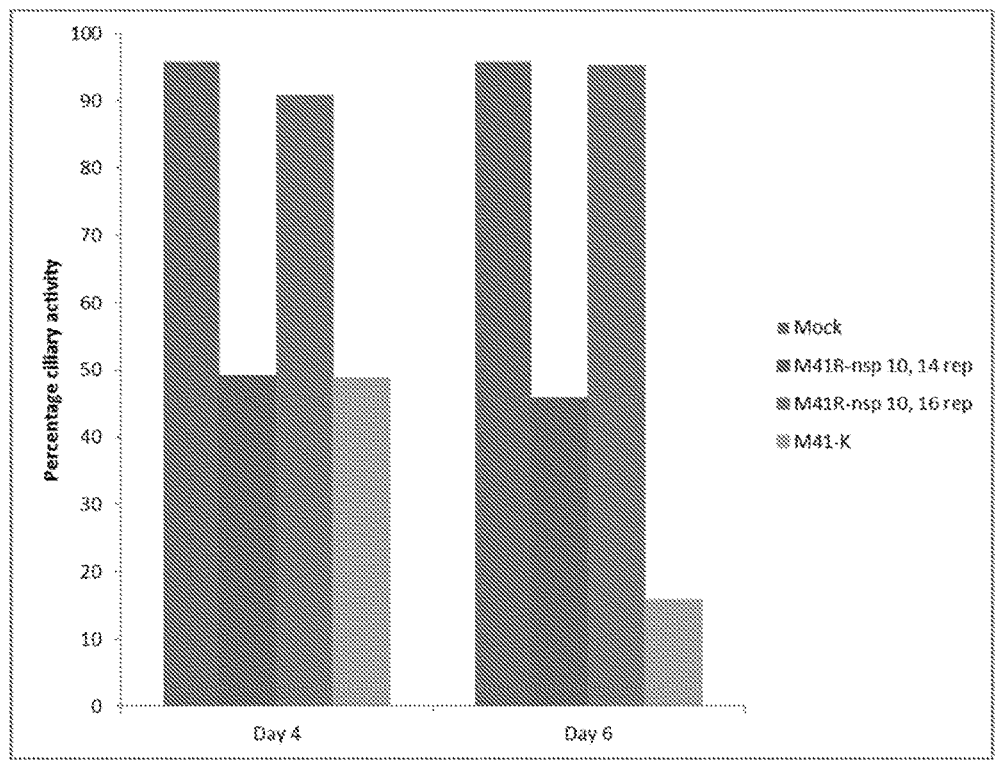
FIG. 11—A) Snicking; B) Respiratory symptoms (wheezing and rales combined) and C) Ciliary activity of rIBV M41R-nsp 10,14 rep and rIBV M41R-nsp 10,16 rep compared to M41-CK (Bars show mock, M41R-nsp10,14rep; M41R-nsp10,16rep and M41-K from left to right of each timepoint).

The inventors also generated rIBV M41R-nsp 10, 14 rep (nsp 10 and 14 are repaired, nsp 15 and 16 contain mutations) and rIBV M41R-nsp 10, 16 rep (nsp 10 and 16 are repaired, nsp 14 and 15 contain mutations) and assessed the pathogenicity of these viruses.

rIBV M41R-nsp 10, 14 rep less pathogenic than M41-K but caused around 50% ciliostasis on days 4-6 post-infection. rIBV M41R-nsp 10, 16 rep was almost apathogenic and caused no ciliostasis (see FIG. 11a-c).

Thus the genome associated with M41-R is a potential backbone genome for a rationally attenuated IBV.

Example 4—Vaccination/Challenge Study with M41-R

Candidate vaccine viruses were tested in studies in which fertilized chicken eggs were vaccinated in ovo at 18 days embryonation and in which the hatchability of the inoculated eggs was determined. The clinical health of the chickens was investigated and the chickens were challenged at 21 days of age with a virulent IB M41 challenge virus at $10^{3.65}$ $EID_{50}$ per dose.

Clinical signs were investigated after challenge protection by the vaccine and a ciliostasis test was performed at 5 days after challenge to investigate the effect of the challenge viruses on movement of the cilia and protection by the vaccine against ciliostasis (inhibition of cilia movement).

In Ovo Vaccination in Commercial Broiler Eggs

The design of the experiment is given in Table 4 and the clinical results are given in Table 5. Hatchability of the eggs inoculated with IB M41-R was good and chickens were healthy. IB M41-R protected against clinical signs after challenge in the broilers (placebo: 19/19 affected, 1B M41-R: 3/18 affected and 1 dead). The results of the ciliostasis test are given in Table 6. IB M41-R generated protection against ciliostasis.

TABLE 6

Results of the ciliostasis test after challenge, for design see Table 1.

| Treatment | Protected/total | Percentage protection |
|---|---|---|
| Saline | 0/19 | 0% |
| IB M41R | 5/18 | 28% |

In Ovo Vaccination in Specific Pathogen-Free (SPF) Eggs

The design of the study in SPF eggs is given in Table 7 and is similar with the design of the studies with commercial broilers, but the vaccination dose for 1B M41-R was higher, ($10^5$ $EID_{50}$ per dose).

The results (Table 8) show that the hatch percentage for IB M41-R hatch was low, and 19 of 40 hatched and the chicks were weak. Eight chicks died. The remaining 11 chickens were challenged and 11 of the chicks hatched from the eggs which had been inoculated with saline were challenged.

In the ciliostasis test after challenge it appeared that all chickens vaccinated in ovo with IB M41-R were protected, whereas none of the controls was protected, see Table 9.

TABLE 4

Design of a hatchability, safety, efficacy study in commercial eggs

| Treatment | Treatment Description | $EID_{50}$[1] per dose | Route of Admin | Day(s) of Admin | Day(s) of Challenge[2] | End of Study | Nr. of eggs per treatment |
|---|---|---|---|---|---|---|---|
| T01 | None | NA | NA | NA | NA | NA | 30 |
| T02 | IB M41-R | $10^4$ | In ovo | 18 days embryonation | At 21 days of age, 20 chickens per group | At 26 days of age | 30 |
| NTX | Saline | NA | In ovo | | | | 30 |

[1]Dose volume 0.1 ml, NA, not applicable.
[2]$10^{3.65}$ $EID_{50}$ per dose.

TABLE 5

Hatch percentages and clinical data before and after challenge in commercial chickens, for design see Table 1.

| Treatment | Hatch/total | Before challenge Vital/total | Before challenge Deaths/total | Before challenge Symptoms/total | After challenge Deaths/total | After challenge Symptoms/total |
|---|---|---|---|---|---|---|
| None | 28/30 | Euthanized directly after hatch for blood collection | | | | |
| IB M41-R | 28/30 | 28/28 | 1/20 | 0/19 | 1/19 | 3/18[1, 7] |
| Saline | 29/30 | 29/29 | 1/20 | 0/19 | 0/19 | 19/19[1, 2, 3, 4, 5, 6, 7] |

[1]Disturbed respiratory system
[2]Whizzing
[3]Change of voice
[4]Breathing difficult
[5]Swollen intra-orbital sinuses
[6]Uneven growth
[7]Weak

TABLE 7

Design of a hatchability, safety, efficacy study in SPF eggs

| Treatment | Treatment Description | $EID_{50}$[1] per dose | Route of Admin | Day of Admin | Day of Challenge[2] | End of Study | Nr. of eggs per treatment |
|---|---|---|---|---|---|---|---|
| T01 | IB M41-R | $10^5$ | In ovo | 18 days embryonation | At 21 days of age | At 26 days of age | 40 |
| T04 | Saline | NA | In ovo | | | | 40 |
| NTX | NA | NA | NA | | NA | | 10 |

[1]Dose volume 0.1 ml, NA, not applicable.
[2]Challenge dose $10^{3.3}$ $EID_{50}$ in 0.2 ml.

TABLE 8

Hatch percentages and clinical data before and after challenge in SPF chickens, for design see Table 7.

| Treatment | Hatch/ total | Vital/ total | Before challenge | | After challenge | |
|---|---|---|---|---|---|---|
| | | | Deaths/ total | Symptoms/ total | Deaths/ total | Symptoms/ total |
| IB M41-R | 19/40 | 11/40 | 8/40 | weak | 0 | 0 |
| Saline | 30/40 | 30/40 | 0 | — | 0 | 0 |
| NA | 9/10 | 9/10 | 0 | — | — | — |

TABLE 9

Results of the ciliostasis test after challenge, for design see Table 7.

| Treatment | Protected/total | Percentage protection |
|---|---|---|
| Saline | 0/11 | 0% |
| IB M41R | 11/11 | 100% |

In conclusion, IB M41-R was safe in commercial eggs, generated protection against clinical signs and to an extent against ciliostasis.

In SPF eggs vaccinated with IB M41 R a relatively low number of chickens hatched. This may be due to the $10^5$ $EID_{50}$ per egg of 1B M41-R used. This was 10-fold higher than the dose used in earlier studies in which there was a higher level of hatchability. The lower hatch percentages may also be caused by a particularly high susceptibility of the batch of SPF eggs for viruses, as in other studies the level of embryo mortality was also higher that had previously been observed.

After challenge all surviving chickens after hatch were completely protected against ciliostasis. It is concluded that IB M41-R has great potential as vaccine to be administered in ovo.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, virology or related fields are intended to be within the scope of the following claims.

The invention claimed is:

1. A live, attenuated coronavirus comprising a variant replicase gene encoding polyproteins comprising a mutation in one or both of non-structural protein(s) nsp-10 and nsp-14, wherein the variant replicase gene encodes a protein comprising an amino acid mutation of Pro to Leu at the position corresponding to position 85 of SEQ ID NO: 6, and/or wherein the variant replicase gene encodes a protein comprising an amino acid mutation of Val to Leu at the position corresponding to position 393 of SEQ ID NO: 7.

2. The coronavirus according to claim 1 wherein the variant replicase gene encodes a protein comprising one or more amino acid mutations selected from:

an amino acid mutation of Leu to Ile at the position corresponding to position 183 of SEQ ID NO: 8; and an amino acid mutation of Val to Ile at the position corresponding to position 209 of SEQ ID NO: 9.

3. The coronavirus according to claim 1 wherein the replicase gene encodes a protein comprising the amino acid mutations Val to Leu at the position corresponding to position 393 of SEQ ID NO: 7; Leu to Ile at the position corresponding to position 183 of SEQ ID NO: 8; and Val to Ile at the position corresponding to position 209 of SEQ ID NO: 9.

4. The coronavirus according to claim 1 wherein the replicase gene encodes a protein comprising the amino acid mutations Pro to Leu at the position corresponding to position 85 of SEQ ID NO: 6; Val to Leu at the position corresponding to position 393 of SEQ ID NO: 7; Leu to Ile at the position corresponding to position 183 of SEQ ID NO: 8; and Val to Ile at the position corresponding to position 209 of SEQ ID NO: 9.

5. The coronavirus according to claim 1 wherein the replicase gene comprises at least one nucleotide substitutions selected from:
   C to T at nucleotide position 12137; and
   G to C at nucleotide position 18114;
   compared to the sequence shown as SEQ ID NO: 1;
   and optionally, comprises one or more nucleotide substitutions selected from T to A at nucleotide position 19047; and
   G to A at nucleotide position 20139;
   compared to the sequence shown as SEQ ID NO: 1.

6. The coronavirus according to claim 1 which is an infectious bronchitis virus (IBV).

7. The coronavirus according to claim 1 which is IBV M41.

8. The coronavirus according to claim 7, which comprises an S protein at least, part of which is from an IBV serotype other than M41.

9. The coronavirus according to claim 8, wherein the S1 subunit is from an IBV serotype other than M41.

10. The coronavirus according to claim 8, wherein the S protein is from an IBV serotype other than M41.

11. The coronavirus according to claim 1 which has reduced pathogenicity compared to a coronavirus expressing a corresponding wild-type replicase, wherein the virus is capable of replicating without being pathogenic to the embryo when administered to an embryonated egg.

12. A variant replicase gene as defined in claim 1.

13. A protein encoded by a variant coronavirus replicase gene according to claim 12.

14. A plasmid comprising a replicase gene according to claim 12.

15. A method for making the coronavirus according to claim 1 which comprises the following steps:
   (i) transfecting a plasmid according to claim 14 into a host cell;
   (ii) infecting the host cell with a recombining virus comprising the genome of a coronavirus strain with a replicase gene;
   (iii) allowing homologous recombination to occur between the replicase gene sequences in the plasmid and the corresponding sequences in the recombining virus genome to produce a modified replicase gene; and
   (iv) selecting for recombining virus comprising the modified replicase gene.

16. The method according to claim 15, wherein the recombining virus is a vaccinia virus.

17. The method according to claim 15 which also includes the step:
   (v) recovering recombinant coronavirus comprising the modified replicase gene from the DNA from the recombining virus from step (iv).

18. A cell capable of producing a coronavirus according to claim 1.

19. A vaccine comprising a coronavirus according to claim 1 and a pharmaceutically acceptable carrier.

20. A method for treating and/or preventing a disease in a subject which comprises the step of administering a vaccine according to claim 19 to the subject.

21. The method of claim 20, wherein the disease is infectious bronchitis (IB).

22. The method according to claim 20 wherein the method of administration is selected from the group consisting of; eye drop administration, intranasal administration, drinking water administration, post-hatch injection and in ovo injection.

23. The method according to claim 21 wherein the administration is in ovo vaccination.

24. A method for producing a vaccine according to claim 19, which comprises the step of infecting a cell according to claim 18 with a coronavirus according to claim 1.

25. The coronavirus according to claim 1, further comprising a mutation in one or both of nsp-15 and nsp-16.

* * * * *

SEQUENCE LISTING

<160> NUMBER OF SEQ ID NOS: 13

<210> SEQ ID NO 1
<211> LENGTH: 27500
<212> TYPE: DNA
<213> ORGANISM: Infectious bronchitis virus

<400> SEQUENCE: 1

```
acttaagata gatattaata tatatctatc acactagcct tgcgctagat ttccaactta      60
acaaaacgga cttaaatacc tacagctggt cctcataggt gttccattgc agtgcacttt     120
agtgccctgg atggcacctg gccacctgtc aggttttgt tattaaaatc ttattgttgc     180
tggtatcact gcttgttttg ccgtgtctca ctttatacat ccgttgcttg ggctacctag     240
tatccagcgt cctacgggcg ccgtggctgg ttcgagtgcg aagaacctct ggttcatcta     300
```

```
gcggtaggcg ggtgtgtgga agtagcactt cagacgtacc ggttctgttg tgtgaaatac    360
ggggtcacct ccccccacat acctctaagg gcttttgagc ctagcgttgg gctacgttct    420
cgcataaggt cggctatacg acgtttgtag ggggtagtgc caaacaaccc ctgaggtgac    480
aggttctggt ggtgtttagt gagcagacat acaatagaca gtgacaacat ggcttcaagc    540
ctaaaacagg gagtatctcc caaactaagg gatgtcattc ttgtatccaa agacattcct    600
gaacaacttt gtgacgcttt gttttttctat acgtcacaca accctaagga ttacgctgat    660
gcttttgcag ttaggcagaa gtttgatcgt aatctgcaga ctgggaaaca gttcaaattt    720
gaaactgtgt gtggtctctt cctcttgaag ggagttgaca aaataacacc tggcgtccca    780
gcaaaagtct taaaagccac ttctaagttg gcagatttag aagacatctt tggtgtctct    840 cccttttgcaa gaaatatacg tgaacttttg aagacagcat gccagtggtc tcttactgta    900
gaaacactgg atgctcgtgc acaaactctt gatgaaattt ttgaccctac tgaaatactt    960
tggcttcagg tggcagcaaa aatccaagtt tcggctatgg cgatgcgcag gcttgttgga   1020
gaagtaactg caaaagtcat ggatgctttg ggctcaaata tgagtgctct tttccagatt   1080
tttaaacaac aaatagtcag aatttttcaa aaagcgctgg ctatttttga aatgtgagt   1140 gaattaccac agcgtattgc agcacttaag atggcttttg ctaagtgtgc caagtccatt   1200
actgttgtgg ttatggagag gactctagtt gttagagagt tcgcaggaac ttgtcttgca   1260
agcattaatg gtgctgttgc aaaattcttt gaagaactcc caaatggttt catgggtgct   1320
aaaattttca ctacacttgc cttctttagg gaggctgcag tgaaaattgt ggataacata   1380
ccaaatgcac cgagaggcac taagggggttt gaagtcgttg gtaatgccaa aggtacacaa   1440
gttgttgtgc gtggcatgcg aaatgactta acactgcttg accaaaaagc tgaaattcct   1500
gtggagtcag aaggttggtc tgcaattttg ggtggacatc tttgctatgt ctttaagagt   1560
ggtgatcgct tttacgcggc acctctttca ggaaattttg cattgcatga tgtgcattgt   1620
tgtgagcgtg ttgtctgtct ttctgatggt gtaacaccgg agataaatga tggacttatt   1680
cttgcagcaa tctactcttc ttttagtgtc gcagaacttg tggcagccat taaaaggggt   1740
gaaccattta agtttctggg tcataaattt gtgtatgcaa aggatgcagc agtttctttt   1800
acattagcga aggctgctac tattgcagat gttttgaagc tgtttcaatc agcgcgtgtg   1860
aaagtagaag atgtttggtc ttcacttact gaaaagtctt ttgaattctg gaggcttgca   1920
tatggaaaag tgcgtaatct cgaagaattt gttaagactt gttttttgtaa ggctcaaatg   1980 gcgattgtga tttagcgac agtgcttgga gagggcattt ggcatcttgt ttcgcaagtc   2040
atctataaag taggtggtct ttttactaaa gttgttgact tttgtgaaaa atattggaaa   2100
ggtttttgtg cacagttgaa aagagctaag ctcattgtca ctgaaaccct ctgtgttttg   2160
aaaggagttg cacagcattg ttttcaacta ttgctggatg caatacagtt tatgtataaa   2220
agttttaaga agtgtgcact tggtagaatc catggagact tgctcttctg gaaaggaggt   2280
gtgcacaaaa ttattcaaga gggcgatgaa atttggtttg acgccattga tagtattgat   2340
gttgaagatc tgggtgttgt tcaagaaaaa ttgattgatt ttgatgtttg tgataatgtg   2400
acacttccag agaaccaacc cggtcatatg gttcaaatcg aggatgacgg aaagaactac   2460
atgttcttcc gcttcaaaaa ggatgagaac atttattata caccaatgtc acagcttggt   2520
gctattaatg tggtttgcaa agcaggcggt aaaactgtca cctttggaga aactactgtg   2580
caagaaatac caccacctga tgttgtgttt attaaggtta gcattgagtg ttgtggtgaa   2640
ccatggaata caatcttcaa aaaggcttat aaggagccca ttgaagtaga gacagacctc   2700
```

```
acagttgaac aattgctctc tgtggtctat gagaaaatgt gtgatgatct caagctgttt    2760
ccggaggctc cagaaccacc accatttgag aatgtcacac ttgttgataa aatggtaaa     2820 gatttggatt gcataaaatc atgccatctg atctatcgtg attatgagag cgatgatgac    2880
atcgaggaag aagatgcaga agaatgtgac acggattcag gtgatgctga ggagtgtgac    2940
actaattcag aatgtgaaga agaagatgag gatactaaag tgttggctct tatacaagac    3000
ccggcaagta acaaatatcc tctgcctctt gatgatgatt atagcgtcta caatggatgt    3060
attgttcata aggacgctct cgatgttgtg aatttaccat ctggtgaaga aacctttgtt    3120
gtcaataact gctttgaagg ggctgttaaa gctcttccgc agaaagttat tgatgttcta    3180
ggtgactggg gtgaggctgt tgatgcgcaa gaacaattgt gtcaacaaga atcaactcgg    3240
gtcatatctg agaaatcagt tgagggtttt actggtagtt gtgatgcaat ggctgaacaa    3300
gctattgttg aagagcagga atagtacct gttgttgaac aaagtcagga tgtagttgtt     3360
tttacacctg cagacctaga agttgttaaa gaaacagcag aagaggttga tgagtttatt    3420
ctcatttctg ctgtccctaa agaagaagtt gtgtctcagg agaaagagga gccacaggtt    3480
gagcaagagc ctaccctagt tgttaaagca aacgtgaga agaaggctaa aaagttcaaa     3540
gttaaaccag ctacatgtga aaaacccaaa ttttgggagt acaaaacatg tgtgggtgat    3600
ttggctgttg taattgccaa agcattggat gagtttaaag agttctgcat tgtaaacgct    3660
gcaaatgagc acatgtcgca tggtggtggc gttgcaaagg caattgcaga cttttgtgga    3720
ccggactttg ttgaatattg cgcggactat gttaagaaac atggtccaca gcaaaaactt    3780
gtcacacctt catttgttaa aggcattcaa tgtgtgaata atgttgtagg acctcgccat    3840
ggagacagca acttgcgtga agagcttgtt gctgcttaca agagtgttct tgtaggtgga    3900
gtggttaact atgttgtgcc agttctctca tcagggattt ttggtgtaga ttttaaaata    3960
tcaatagatg ctatgcgcga agcttttaaa ggttgtgcca tacgcgttct tttattttct    4020
ctgagtcaag aacacatcga ttatttcgat gcaacttgta agcagaagac aatttatctt    4080
acggaggatg tgttaaaata ccgctctgtt gttttaaaac ctggtgattc tttgggtcaa    4140
tttggacagg tttttgcaag aaataaggta gtcttttcgg ctgatgatgt tgaggataaa    4200
gaaatcctct ttatacccac aactgacaag actattcttg aatattatgg tttagatgcg    4260
caaaagtatg taacatattt gcaaacgctt gcgcagaaat gggatgttca atatagagac    4320
aattttgtta tattgagtg gcgtgacgga aattgctgga ttagttcagc aatagttctc     4380
cttcaagctg ctaaaattag atttaaaggt tttcttgcag aagcatgggc taaactgttg    4440
ggtggagatc ctacagactt tgttgcctgg tgttatgcaa gttgcaatgc taaagtaggt    4500 gattttcag atgctaattg gctttttggcc aatttagcag aacattttga cgcagattac     4560
acaaatgcac ttcttaagaa gtgtgtgtcg tgcaattgtg gtgttaagag ttatgaactt    4620 agggggtcttg aagcctgtat tcagccagtt cgagcaccta atcttctaca ttttaaaacg    4680
caatattcaa attgcccaac ctgtggtgca agtagtacgg atgaagtaat agaagcttca    4740
ttaccgtact tattgcttttt tgctactgat ggtcctgcta cagttgattg tgatgaaaat    4800
gctgtaggga ctgttgtttt cattggctct actaatagtg gccattgtta tacacaagcc    4860
gatggtaagg cttttgacaa tcttgctaag atagaaaat ttggaaggaa gtcgccttac     4920
attacagcaa tgtatacacg ttttctcttt aggagtgaaa atcccctact tgttgttgaa    4980
catagtaagg gtaaagctaa agtagtaaaa gaagatgttt ctaaccttgc tactagttct    5040
```

```
aaagccagtt ttgacgatct tactgacttt gaacagtggt atgatagcaa catctatgag    5100
agtcttaaag tgcaggagac acctgataat cttgatgaat atgtgtcatt tacgacaaag    5160
gaagattcta agttgccact gacacttaaa gttagaggta tcaaatcagt tgttgacttt    5220
aggtctaagg atggttttac ttataagtta acacctgata ctgatgaaaa ttcaaaaaca    5280
ccagtctact acccagtctt ggattctatt agtcttaggg caatatgggt tgaaggcagt    5340
gctaattttg ttgttgggca tccaaattat tatagtaagt ctctccgaat tcccacgttt    5400
tgggaaaatg ccgagagctt tgttaaaatg ggttataaaa ttgatggtgt aactatgggc    5460
ctttggcgtg cagaacacct taataaacct aatttggaga gaattttaa cattgctaag     5520
aaagctattg ttggatctag tgttgttact acgcagtgtg gtaaaatact agttaaagca    5580
gctacatacg ttgccgataa agtaggtgat ggtgtagttc gcaatattac agatagaatt    5640
aagggtcttt gtggattcac acgtggccat tttgaaaaga aaatgtccct acaatttcta    5700
aagacacttg tgttctttt ctttatttc ttaaaggcta gtgctaagag tttagtttct       5760
agctataaga ttgtgttatg taaggtggtg tttgctacct tacttatagt gtggtttata    5820
tacacaagta atccagtagt gtttactgga atacgtgtgc tagacttcct atttgaaggt    5880
tctttatgtg gtccttataa tgactacggt aaagattctt ttgatgtgtt acgctattgt    5940
gcaggtgatt ttacttgtcg tgtgtgttta catgatagag attcacttca tctgtacaaa    6000
catgcttata gcgtagaaca aatttataag gatgcagctc tggcattaa ctttaattgg      6060
aattggcttt atttggtctt tctaatatta tttgttaagc cagtggcagg ttttgttatt    6120
atttgttatt gtgttaagta tttggtattg agttcaactg tgttgcaaac tggtgtaggt    6180
tttctagatt ggtttgtaaa aacagttttt acccatttta attttatggg agcgggattt    6240
tatttctggc tcttttacaa gatatacgta caagtgcatc atatattgta ctgtaaggat    6300
gtaacatgtg aagtgtgcaa gagagttgca cgcagcaaca ggcaagaggt tagcgttgta    6360
gttggtggac gcaagcaaat agtgcatgtt tacactaatt ctggctataa cttttgtaag    6420
agacataatt ggtattgtag aaattgtgat gattatggtc accaaaatac atttatgtcc    6480
cctgaagttg ctggcgagct ttctgaaaag cttaagcgcc atgttaaacc tacagcatat    6540
gcttaccacg ttgtgtatga ggcatgcgtg gttgatgatt ttgttaattt aaaatataag    6600
gctgcaattc ctggtaagga taatgcatct tctgctgtta agtgtttcag tgttacagat    6660
ttttttaaaga aagctgtttt tcttaaggag gcattgaaat gtgaacaaat atctaatgat    6720
ggttttatag tgtgtaatac acagagtgcg catgcactag aggaagcaaa gaatgcagcc    6780
gtctattatg cgcaatatct gtgtaagcca atacttatac ttgaccaggc actttatgag    6840
caattaatag tagagcctgt gtctaagagt gttatagata agtgtgtag cattttgtct      6900
aatataatat ctgtagatac tgcagcttta aattataagg caggcacact tcgtgatgct    6960
ctgcttttcta ttactaaaga cgaagaagcc gtagatatgg ctatcttctg ccacaatcat    7020
gaagtggaat acactggtga cggttttact aatgtgatac cgtcatatgg tatggacact    7080
gataagttga cacctcgtga tagggggttt ttgataaatg cagatgcttc tattgctaat    7140
ttaagagtca aaaatgctcc tccggtagta tggaagtttt ctgatcttat taaattgtct    7200
gacagttgcc ttaaatattt aatttcagct actgtcaagt caggaggtcg tttctttata    7260
acaaagtctg gtgctaaaca agttattct tgtcataccc agaaactgtt ggtagagaaa       7320
aaggcaggtg tgttattaa taacactttt aaatggttta tgagttgttt taaatggctt       7380
tttgtctttt atatactttt tacagcatgt tgtttgggtt actactatat ggagatgaat    7440
```

```
aaaagttttg ttcaccccat gtatgatgta aactccacac tgcatgttga agggttcaaa    7500
gttatagaca aaggtgttat tagagagatt gtgtcagaag ataattgttt ctctaataag    7560
tttgttaatt ttgacgcctt ttggggtaaa tcatatgaaa ataataaaaa ctgtccaatt    7620
gttacagttg ttatagatgg tgacgggaca gtagctgttg gtgttcctgg ttttgtatca    7680
tgggttatgg atggtgttat gtttgtgcat atgacacaga ctgatcgtag accttggtac    7740
attcctacct ggtttaatag agaaattgtt ggttacactc aggattcaat tatcactgag    7800
ggtagttttt atacatctat agcattattt tctgctagat gtttatattt aacagccagc    7860
aatacacctc aattgtattg ttttaatggc gacaatgatg cacctggagc cttaccattt    7920
ggtagtatta ttcctcatag agtatacttc caacctaatg gtgttaggct tatagttcca    7980
caacaaatac tgcatacacc ctacatagtg aagtttgttt cagacagcta ttgtagaggt    8040
agtgtatgtg agtatactaa accaggttac tgtgtgtcac tagactccca atgggttttg    8100
tttaatgatg aatacattag taaacctggc gttttctgtg gttctactgt tagagaactt    8160
atgtttaata tggttagtac attctttact ggtgtcaacc ctaatattta tattcagcta    8220
gcaactatgt ttttaatact agttgttatt gtgttaattt ttgcaatggt tataaagttt    8280
caaggtgttt ttaaagctta tgcgaccatt gtgtttacaa taatgttagt ttgggttatt    8340
aatgcatttg ttttgtgtgt acatagttat aatagtgttt tagctgttat attattagta    8400
ctctattgct atgcatcatt ggttacaagt cgcaatactg ctataataat gcattgttgg    8460
cttgttttta cctttggttt aatagtaccc acatggttgg cttgttgcta tctgggattt    8520
attctttata tgtacacacc gttggttttc tggtgttacg gtactactaa aaatactcgt    8580
aagttgtatg atggcaacga gtttgttggt aattatgacc ttgctgcgaa gagcactttt    8640
gttattcgtg gtactgaatt tgttaagctt acgaatgaga taggtgataa atttgaagcc    8700 tatcttctg cgtatgctag acttaaatac tattcaggca ctggtagtga gcaagattac    8760
ttgcaagctt gtcgtgcatg gttagcttat gctttggacc aatatagaaa tagtggtgtt    8820
gaggttgttt atacccccacc gcgttactct attggtgtta gtagactaca cgctggtttt    8880
aaaaaactag tttctcctag tagtgctgtt gagaagtgca ttgttagtgt ctcttataga    8940
ggcaataatc ttaatggact gtggctgggt gattctattt actgcccacg ccatgtgtta    9000
ggtaagttta gtggtgacca gtggggtgac gtactaaacc ttgctaataa tcatgagttt    9060
gaagttgtaa ctcaaaatgg tgttactttg aatgttgtca gcaggcggct taaaggagca    9120
gttttaattt tacaaactgc agttgccaat gctgaaactc ctaagtataa gtttgttaaa    9180
gctaattgtg gtgatagttt cactatagct tgttcttatg gtggtacagt tataggactt    9240
taccctgtca ctatgcgttc taatggtact attagagcat cttttcctag aggagcctgt    9300
ggctcagttg gttttaatat agaaaagggt gtagttaatt tcttttata tgcaccatct    9360 gagttaccta atgcattaca cactggaact gacctaatgg tgagttttta tggtggttat    9420
gtagatgaag aggttgcgca aagagtgcca ccagataatc tagttactaa caatattgta    9480
gcatggctct atgcggcaat tattagtgtt aagaaagta gttttcaca acctaaatgg    9540 ttggagagta ctactgtttc tattgaagat acaataggg gggctagtga taatggtttt    9600
actccatttt ccactagtac tgctattact aaattaagtg ctataactgg ggttgatgtt    9660
tgtaaactcc ttcgcactat tatggtaaaa agtgctcaat ggggtagtga tcccattta    9720 ggacaatata atttgaaga cgaattgaca ccagaatctg tatttaatca agttggtggt    9780
```

```
gttaggttac agtcttcttt tgtaagaaaa gctacatctt ggttttggag tagatgtgta    9840
ttagcttgct tcttgtttgt gttgtgtgct attgtcttat ttacggcagt gccacttaag    9900
ttttatgtac atgcagctgt tattttgttg atggctgtgc tctttatttc ttttactgtt    9960
aaacatgtta tggcatacat ggacactttc ctattgccta cattgattac agttattatt   10020
ggagtttgtg ctgaagtccc tttcatatac aatactctaa ttagtcaagt tgttattttc   10080
ttaagccaat ggtatgatcc tgtagtcttt gatactatgg taccatggat gttattgcca   10140
ttagtgttgt acactgcttt taagtgtgta caaggctgct atatgaattc tttcaatact   10200
tctttgttaa tgctgtatca gtttatgaag ttaggttttg ttatttacac ctcttcaaac   10260
actcttactg catatacaga aggtaattgg gagttattct ttgagttggt tcacactatt   10320
gtgttggcta atgttagtag taattcctta attggtttaa ttgttttaa gtgtgctaag   10380 tggattttat attattgcaa tgcaacatac tttaataatt atgtgttaat ggcagtcatg   10440
gttaatggca taggctggct ttgcacctgt tactttggat tgtattggtg ggttaataaa   10500 gttttttggtt taaccttagg taaatacaat tttaaagttt cagtagatca atataggtat   10560
atgtgtttgc ataaggtaaa tccacctaaa actgtgtggg aggtctttac tacaaatata   10620
cttatacaag gaattggagg cgatcgtgtg ttgcctatag ctacagtgca atctaaattg   10680
agtgatgtaa agtgtacaac tgttgtttta atgcagcttt tgactaagct taatgttgaa   10740
gcaaattcaa aaatgcatgc ttatcttgtt gagttacaca ataaaatcct cgcatctgat   10800
gatgttggag agtgcatgga taatttattg ggtatgctta taacactatt ttgtatagat   10860
tctactattg atttgggtga gtattgtgat gatatactta agaggtcaac tgtattacaa   10920
tcggttactc aagagttttc gcacataccc tcgtatgctg aatatgaaag agctaagagt   10980
atttatgaaa aggttttagc cgattctaaa aatggtggtg taacacagca agagcttgct   11040
gcatatcgta aagctgccaa tattgcaaag tcagtttttg atagagactt ggctgttcaa   11100
aagaagttag atagcatggc agaacgtgct atgacaacaa tgtataaaga ggcgcgtgta   11160
actgatagaa gagcaaaatt agtttcatca ttacatgcac tacttttttc aatgcttaag   11220
aaaatagatt ctgagaagct taatgtctta tttgaccagg cgaatagtgg tgttgtaccc   11280
ctagcaactg ttccaattgt ttgtagtaat aagcttaccc ttgttatacc agacccagag   11340
acgtgggtca agtgtgtgga gggtgtgcat gttacatatt caacagttgt ttggaatata   11400
gactgtgtta ctgatgccga tggcacagag ttacacccca cttctacagg tagtggattg   11460
acttactgta aagtggtga taatatagca tggcctttaa aggttaactt gactaggaat   11520
gggcataata aggttgatgt tgccttgcaa aataatgagc ttatgcctca cggtgtaaag   11580
acaaaggctt gcgtagcagg tgtagatcaa gcacattgta gcgttgagtc taatgttat   11640 tatacaagta ttagtggcag ttcagttgta gctgctatta cctcttcaaa tcctaatctg   11700
aaagtagcct cttttttgaa tgaggcaggt aatcagattt atgtagactt agaccccacca   11760 tgtaaatttg gtatgaaagt gggtgataag gttgaagttg tttacctgta ttttataaaa   11820
aatacgaggt ctattgtaag aggtatggta cttggtgcta tatctaatgt tgttgtgtta   11880
caatctaaag gtcatgagac agaggaagtg gatgctgtag gcattctctc actttgttct   11940
tttgcagtag atcctgcgga tacatattgt aaatatgtgg cagcaggtaa tcaaccttta   12000
ggtaactgtg ttaaaatgtt gacagtacat aatggtagtg gttttgcaat aacatcaaag   12060
ccaagtccaa ctccggatca ggattcttat ggaggagctc tgtgtgtct ttattgtaga   12120 gcacatatag cacaccctgg cggagcagga aatttagatg acgctgtca atttaaggt   12180
```

```
tcttttgtgc aaatacctac tacggagaaa gatcctgttg gattctgtct acgtaacaag   12240
gtttgcactg tttgtcagtg ttggattggt tatggatgtc agtgtgattc acttagacaa   12300
cctaaacctt ctgttcagtc agttgctgtt gcatctggtt ttgataagaa ttatttaaac   12360
gggtacgggg tagcagtgag gctcggctga taccctagc taatggatgt gaccccgatg    12420
ttgtaaagcg agcctttgat gtttgtaata aggaatcagc cggtatgttt caaaatttga   12480
agcgtaactg tgcacgattc caagaagtac gtgatactga agatggaaat cttgagtatt   12540
gtgattctta ttttgtggtt aaacaaacca ctcctagtaa ttatgaacat gagaaagctt   12600
gttatgaaga cttaaagtca gaagtaacag ctgatcatga tttctttgtg ttcaataaga   12660
acatttataa tattagtagg cagaggctta ctaagtatac tatgatggat ttttgctatg   12720
ctttgcggca ctttgaccca aaggattgcg aagttcttaa agaaatactt gtcacttatg   12780
gttgtataga agattatcac cctaagtggt ttgaagagaa taaggattgg tacgacccaa   12840
tagaaaaccc taaatattat gccatgttgg ctaaaatggg acctattgta cgacgtgctt   12900
tattgaatgc tattgagttc ggaaacctca tggttgaaaa aggttatgtt ggtgttatta   12960
cacttgataa ccaagatctt aatggcaaat tttatgattt tggtgatttt cagaagacag   13020
cgcctggtgc tggtgttcct gttttgata cgtattattc ttacatgatg cccatcatag    13080
ccatgactga tgcgttggca cctgagaggt attttgaata tgatgtgcat aagggttata   13140
aatcttatga tctcctcaag tatgattata ctgaggagaa acaagatttg tttcagaagt   13200
actttaagta ttgggatcaa gagtatcacc ctaactgtcg cgactgtagt gatgacaggt   13260
gtttgataca ttgtgcaaac ttcaacatct tgttttctac acttgtaccg cagacttctt   13320
tcggtaattt tgtgtagaaag gtttttgttg atggtgtacc atttatagct acttgtggct   13380
atcattctaa ggaacttggt gttattatga atcaagataa caccatgtca ttttcaaaaa   13440
tgggtttgag tcaactcatg cagttttgtt gagatcctgc cttgttagtg gggacatcca   13500
ataaattagt ggatcttaga acgtcttgtt ttagtgtttg tgctttagcg tctggtatta   13560
ctcatcaaac ggtaaaacca ggtcacttta acaaggattt ctacgatttt gcagagaagg   13620
ctggtatgtt taaggaaggt tcttctatac cacttaaaca tttcttctac ccacagactg   13680
gtaatgctgc tataaacgat tatgattatt atcgttataa caggcctacc atgtttgata   13740
tacgtcaact tttattttgt ttagaagtga cttctaaata ttttgaatgt tatgaaggcg   13800
gctgtatacc agcaagccaa gttgtagtta acaatttaga taagagtgca ggttatccgt   13860
tcaataagtt tggaaaggcc cgtctctatt atgaaatgag tctagaggag caggaccaac   13920
tctttgagag tacaaagaag aacgtcctgc ctactataac tcagatgaat ttaaaatatg   13980
ccatatccgc gaaaaataga gcgcgtacag tggcaggtgt gtctatcctt tctactatga   14040
ctaataggca gtttcatcag aagattctta agtctatagt caacactaga aacgctcctg   14100
tagttattgg aacaaccaag ttttatggcg gttgggataa catgttgaga aaccttattc   14160
agggtgttga agacccgatt cttatgggtt gggattatcc aaagtgtgat agagcaatgc   14220
ctaatttgtt gcgtatagca gcatctttag tactcgctcg taaacacact aattgttgta   14280
cttggtctga acgcgtttat aggttgtata atgaatgcgc tcaggtttta tctgaaactg   14340
tcttagctac aggtggtata tatgtgaaac ctggtggtac tagcagtgga gatgctacta   14400
ctgcttatgc aaacagtgtt ttcaacataa tacaagccac atctgctaat gttgcgcgtc   14460
ttttgagtgt tataacgcgt gatattgtat atgatgacat taagagcttg cagtatgaat   14520
```

```
tgtaccagca ggtttatagg cgagtcaatt ttgacccagc atttgttgaa aagttttatt    14580
cttatttgtg taagaatttc tcattgatga tcttgtctga cgacggtgtt gtttgttata    14640
acaacacatt agccaaacaa ggtcttgtag cagatatttc tggttttaga gaagttctct    14700
actatcagaa caatgttttt atggctgatt ctaaatgttg ggttgaacca gatttagaaa    14760
aaggcccaca tgaattttgt tcacagcaca caatgttagt ggaggttgat ggtgagccta    14820
gatacttgcc atatccagac ccatcacgta ttttgtgtgc atgtgttttt gtagatgatt    14880
tggataagac agaatctgtg ctgttatgg agcgttatat cgctcttgcc atagatgcgt    14940
acccactagt acatcatgaa aatgaggagt acaagaaggt attctttgtg cttctttcat    15000
acatcagaaa actctatcaa gagctttctc agaatatgct tatggactac tcttttgtaa    15060
tggatataga taagggtagt aaattttggg aacaggagtt ctatgaaaat atgtatagag    15120
cccctacaac attacagtct tgtggcgttt gtgtagtgtg taatagtcaa actatattgc    15180
gctgtggtaa ttgtattcgc aaaccatttt tgtgttgtaa gtgttgctat gaccatgtca    15240
tgcacacaga ccacaaaaat gttttgtcta taaatcctta catttgctca cagccaggtt    15300
gtggtgaagc agatgttact aaattgtacc tcggaggtat gtcatacttc tgcggtaatc    15360
ataaaccaaa gttatcaata ccgttagtat ctaatgtac agtgtttgga atttacaggg    15420
ctaattgtgc aggtagcgaa atgttgatg attttaatca actagctact actaattggt    15480
ctactgtgga accttatatt ttggcaaatc gttgtgtaga ttcgttgaga cgctttgctg    15540
cagagacagt aaaagctaca gaagaattac ataagcaaca atttgctagt gcagaagtga    15600
gagaagtact ctcagatcgt gaattgatc tgtcttggga gccaggtaaa accaggcctc    15660
cattgaatag aaattatgtt ttcactggct ttcacttta ctagaactagt aaagttcagc    15720 tcggtgattt tacatttgaa aaaggtgaag gtaaggacgt tgtctattat cgagcgacgt    15780
ctactgctaa attgtctgtt ggagacattt ttgttttaac ctcacacaat gttgtttctc    15840
ttatagcgcc aacgttgtgt cctcagcaaa ccttttctag gtttgtgaat ttaagaccta    15900
atgtgatggt acctgcgtgt tttgtaaata acattccatt gtaccattta gtaggcaagc    15960
agaagcgtac tacagtacaa ggccctcctg gcagtggtaa atcccatttt gctataggat    16020
tggcggctta ctttagtaac gcccgtgtcg ttttactgc atgctctcat gcagctgttg    16080 atgcttatg tgaaaaagct tttaagtttc ttaaagtaga tgattgcact cgtatagtac    16140
ctcaaaggac tactatcgat tgcttctcta agtttaaagc taatgacaca ggcaaaaagt    16200
acatttttag tactattaat gccttgccag aagttagttg tgacattctt ttggttgacg    16260
aggttagtat gttgaccaat tacgaattgt cttttattaa tggtaagata aactatcaat    16320
atgttgtgta tgtaggtgat cctgctcaat taccggcgcc tcgtacgttg cttaacggtt    16380
cactctctcc aaaggattat aatgttgtca caaaccttat ggtttgtgtt aaacctgaca    16440
ttttccttgc aaagtgttac cgttgtccta aagaaattgt agatactgtt tctactcttg    16500
tatatgatgg aaagtttatt gcaaataacc cggaatcacg tcagtgtttc aaggttatag    16560
ttaataatgg taattctgat gtaggacatg aaagtggctc agcctacaac ataactcaat    16620
tagaatttgt gaaagatttt gtctgtcgca ataaggaatg gcgggaagca acattcattt    16680
caccttataa tgctatgaac cagagagcct accgtatgct tggacttaat gttcagacag    16740
tagactcgtc tcaaggttcg gagtatgatt atgttatctt ttgtgttact gcagattcgc    16800
agcatgcact gaatattaac agattcaatg tagcgcttac aagagccaag cgtggtatac    16860
tagttgtcat gcgtcagcgt gatgaactat attcagctct taagtttata gagcttgata    16920
```

-continued

```
gtgtagcaag tctgcaaggt acaggcttgt ttaaaatttg caacaaagag tttagtggtg    16980
ttcacccagc ttatgcagtc acaactaagg ctcttgctgc aacttataaa gttaatgatg    17040
aacttgctgc acttgttaac gtggaagctg gttcagaaat aacatataaa catcttattt    17100
ctttgttagg gtttaagatg agtgttaatg ttgaaggctg ccacaacatg tttataacac    17160
gtgatgaggc tatccgcaac gtaagaggtt gggtaggttt tgatgtagaa gcaacacatg    17220
cttgcggtac taacattggt actaacctgc ctttccaagt aggtttctct actggtgcag    17280
actttgtagt tacgcctgag ggacttgtag atacttcaat aggcaataat tttgagcctg    17340
tgaattctaa agcacctcca ggtgaacaat taatcactt gagagcgtta ttcaaaagtg     17400
ctaaaccttg gcatgttgta aggccaagga ttgtgcaaat gttagcggat aacctgtgca    17460
acgtttcaga ttgtgtagtg tttgtcacgt ggtgtcatgg cctagaacta accactttgc    17520
gctattttgt taaaataggc aaggaccaag tttgttcttg cggttctaga gcaacaactt    17580
ttaattctca tactcaggct tatgcttgtt ggaagcattg cttgggtttt gattttgttt    17640
ataatccact cttagtggat attcaacagt ggggttattc tggtaaccta caatttaacc    17700
atgatttgca ttgtaatgtg catggacacg cacatgtagc ttctgcggat gctattatga    17760
cgcgttgtct tgcaattaat aatgcatttt gtcaagatgt caactgggat ttaacttacc    17820
ctcatatagc aaatgaggat gaagtcaatt ctagctgtag atatttacaa cgcatgtatc    17880
ttaatgcatg tgttgatgct cttaaagtta acgttgtcta tgatataggc aaccctaaag    17940
gtataaaatg tgttagacgt ggagacttaa attttagatt ctatgataag aatccaatag    18000
tacccaatgt caagcagttt gagtatgact ataatcagca caaagataag tttgctgatg    18060
gtctttgtat gttttggaat tgtaatgtgg attgttatcc cgacaattcc ttagtttgta    18120
ggtacgacac acgaaatttg agtgtgttta acctacctgg ttgtaatggt ggtagcttgt    18180
atgttaacaa gcatgcattc cacacaccta aatttgatcg cactagcttt cgtaatttga    18240
aagctatgcc attcttttc tatgactcat cgccttgcga gaccattcaa ttggatggag    18300
ttgcgcaaga ccttgtgtca ttagctacga aagattgtat cacaaaatgc aacataggcg    18360
gtgctgtttg taaaaagcac gcacaaatgt atgcagattt tgtgacttct tataatgcag    18420
ctgttactgc tggtttttact ttttgggtta ctaataattt taaccccatat aatttgtgga    18480 aaagtttttc agctctccag tctatcgaca atattgctta atatgtat aagggtggtc     18540 attatgatgc tattgcagga gaaatgccca ctatcgtaac tggagataaa gttttgttta    18600
tagatcaagg cgtagaaaaa gcagttttt ttaatcaaac aattctgcct acatctgtag     18660
cgtttgagct gtatgcgaag agaaatattc gcacactgcc aaacaaccgt attttgaaag    18720
gtttgggtgt agatgtgact aatggatttg taatttggga ttacacgaac caaacaccac    18780
tataccgtaa tactgttaag gtatgtgcat atacagacat agaaccaaat ggcctaatag    18840
tgctgtatga tgatagatat ggtgattacc agtcttttct agctgctgat aatgctgttt    18900
tagtttctac acagtgttac aagcggtatt cgtatgtaga aataccgtca aacctgcttg    18960
ttcagaacgg tattccgtta aaagatggag cgaacctgta tgtttataag cgtgttaatg    19020 gtgcgttgt tacgctacct aacacattaa acacacaggg tcgcagttat gaaacttttg     19080
aacctcgtag tgatgttgag cgtgattttc tcgacatgtc tgaggagagt tttgtagaaa    19140 agtatgtaa agaattaggt ctacagcaca tactgtatgg tgaagttgat aagcccaat     19200 taggtggttt acacactgtt ataggtatgt gcagactttt acgtgcgaat aagttgaacg    19260
```

```
caaagtctgt tactaattct gattctgatg tcatgcaaaa ttattttgta ttggcagaca    19320
atggttccta caagcaagtg tgtactgttg tggatttgct gcttgatgat ttcttagaac    19380
ttcttaggaa catactgaaa gagtatggta ctaataagtc taaagttgta acagtgtcaa    19440
ttgattacca tagcataaat tttatgactt ggtttgaaga tggcattatt aaaacatgtt    19500
atccacagct tcaatcagca tggacgtgtg gttataatat gcctgaactt tataaagttc    19560
agaattgtgt tatggaacct tgcaacattc ctaattatgg tgttggaata gcgttgccaa    19620
gtggtattat gatgaatgtg gcaaagtata cacaactctg tcaataccct tcgaaaacaa    19680
caatgtgtgt accgcataat atgcgagtaa tgcattttgg agctggaagt gacaaaggag    19740
tggctccagg tagtactgtt cttaaacaat ggctcccaga agggacactc cttgtcgata    19800
atgatattgt agactatgtg tctgatgcac atgtttctgt gctttcagat tgcaataaat    19860
ataagacaga gcacaagttt gatcttgtga tatctgatat gtatacagac aatgattcaa    19920
aaagaaagca tgaaggcgtg atagccaata tggcaatga tgacgttttc atatatctct    19980
caagttttct tcgtaataat ttggctctag gtggtagttt tgctgtaaaa gtgacagaga    20040
caagttggca cgaagtttta tatgacattg cacaggattg tgcatggtgg acaatgtttt    20100
gtacagcagt gaatgcctct tcttcagaag cattcttggt tggtgttaat tatttgggtg    20160
caagtgaaaa ggttaaggtt agtggaaaaa cgctgcacgc aaattatata ttttggagga    20220
attgtaatta tttacaaacc tctgcttata gtatatttga cgttgctaag tttgatttga    20280
gattgaaagc aacaccagtt gttaatttga aaactgaaca aaagacagac ttagtcttta    20340
atttaattaa gtgtggtaag ttactggtaa gagatgttgg taacacctct tttactagtg    20400
actcttttgt gtgtactatg tagtgctgct ttgtatgaca gtagttctta cgtttactac    20460
taccaaagtg cctttagacc acctaatggt tggcatttac acggggtgc ttatgcggta    20520
gttaatattt ctagcgaatc taataatgca ggctcttcac ctgggtgtat tgttggtact    20580
attcatggtg gtcgtgttgt taatgcttct tctatagcta tgacggcacc gtcatcaggt    20640
atggcttggt ctagcagtca gttttgtact gcacactgta acttttcaga tactacagtg    20700
tttgttacac attgttataa atatgatggg tgtcctataa ctggcatgct tcaaaagaat    20760
ttttttacgtg tttctgctat gaaaatggc cagcttttct ataatttaac agttagtgta    20820
gctaagtacc ctactttaa atcatttcag tgtgttaata atttaacatc cgtatattta    20880
aatggtgatc ttgtttacac ctctaatgag accacagatg ttacatctgc aggtgtttat    20940
tttaaagctg gtggacctat aacttataaa gttatgagag aagttaaagc cctggcttat    21000
tttgttaatg gtactgcaca agatgttatt ttgtgtgatg gatcacctag aggcttgtta    21060
gcatgccagt ataatactgg caattttca gatggctttt atccttttat taatagtagt    21120
ttagttaagc agaagtttat tgtctatcgt gaaaatagtt taatactac ttttacgtta    21180
cacaatttca cttttcataa tgagactggc gccaaccccta atcctagtgg tgttcagaat    21240
attcaaactt accaaacaca aacagctcag agtggttatt ataattttaa ttttcctttt    21300
ctgagtagtt ttgttttataa ggagtctaat tttatgtatg atcttatca cccaagttgt    21360
aattttagac tagaaactat taataatggc ttgtggttta attcactttc agtttcaatt    21420
gcttacggtc ctcttcaagg tggttgcaag caatctgtct ttagtggtag agcaacttgt    21480
tgttatgctt attcatatgg aggtcctttcg ctgtgtaaag gtgtttattc aggtgagtta    21540
gatcttaatt ttgaatgtgg actgttagtt tatgttacta gagcggtgg ctctcgtata    21600
caaacagcca ctgaaccgcc agttataact cgacacaatt ataataatat tactttaaat    21660
```

```
acttgtgttg attataatat atatggcaga actggccaag gttttattac taatgtaacc   21720
gactcagctg ttagttataa ttatctagca gacgcaggtt tggctatttt agatacatct   21780
ggttccatag acatctttgt tgtacaaggt gaatatggtc ttacttatta taaggttaac   21840
ccttgcgaag atgtcaacca gcagtttgta gtttctggtg gtaaattagt aggtattctt   21900
acttcacgta atgagactgg ttctcagctt cttgagaacc agttttacat taaaatcact   21960
aatggaacac gtcgttttag acgttctatt actgaaaatg ttgcaaattg cccttatgtt   22020
agttatggta agttttgtat aaaacctgat ggttcaattg ccacaatagt accaaaacaa   22080
ttggaacagt ttgtggcacc tttacttaat gttactgaaa atgtgctcat acctaacagt   22140
tttaatttaa ctgttacaga tgagtacata caaacgcgta tggataaggt ccaaattaat   22200
tgtctgcagt atgtttgtgg caattctctg gattgtagag atttgtttca acaatatggg   22260
cctgtttgtg acaacatatt gtctgtagta aatagtattg gtcaaaaaga agatatggaa   22320
cttttgaatt tctattcttc tactaaaccg gctggtttta ataccattt tcttagtaat   22380
gttagcactg gtgagtttaa tatttctctt ctgttaacaa ctcctagtag tcctagaagg   22440
cgttctttta ttgaagacct tctatttaca agcgttgaat ctgttggatt accaacagat   22500
gacgcataca aaaattgcac tgcaggacct ttaggttttc ttaaggacct tgcgtgtgct   22560
cgtgaatata atggtttgct tgtgttgcct cccattataa cagcagaaat gcaaattttg   22620
tatactagtt ctcagtagc ttctatggct tttggtggta ttactgcagc tggtgctata   22680
ccttttgcca cacaactgca ggctagaatt aatcacttgg gtattaccca gtcacttttg   22740
ttgaagaatc aagaaaaaat tgctgcttcc tttaataagg ccattggtcg tatgcaggaa   22800
ggttttagaa gtacatctct agcattacaa caaattcaag atgttgttaa taagcagagt   22860
gctattctta ctgagactat ggcatcactt aataaaaatt ttggtgctat ttcttctatg   22920
attcaagaaa tctaccagca acttgacgcc atacaagcaa atgctcaagt ggatcgtctt   22980
ataactggta gattgtcatc actttctgtt ttagcatctg ctaagcaggc ggagcatatt   23040
agagtgtcac aacagcgtga gttagctact cagaaaatta atgagtgtgt taagtcacag   23100
tctattaggt actccttttg tggtaatgga cgacatgttc taaccatacc gcaaaatgca   23160
cctaatggta tagtgtttat acacttttct tatactccag atagttttgt taatgttact   23220
gcaatagtgg gttttgtgt aaagccagct aatgctagtc agtatgcaat agtacccgct   23280
aatggtaggg gtattttat acaagttaat ggtagttact acatcacagc acgagatatg   23340
tatatgccaa gagctattac tgcaggagat atagttacgc ttacttcttg tcaagcaaat   23400
tatgtaagtg taaataagac cgtcattact acattcgtag acaatgatga ttttgatttt   23460
aatgacgaat tgtcaaaatg gtggaatgac actaagcatg agctaccaga ctttgacaaa   23520
ttcaattaca cagtacctat acttgacatt gatagtgaaa ttgatcgtat tcaaggcgtt   23580
atacagggtc ttaatgactc tttaatagac cttgaaaaac tttcaatact caaaacttat   23640
attaagtggc cttggtatgt gtggttagcc atagcttttg ccactattat cttcatctta   23700
atactaggat gggttttctt catgactgga tgttgtggtt gttgttgtgg atgctttggc   23760
attatgcctc taatgagtaa gtgtggtaag aaatcttctt attacacgac ttttgataac   23820
gatgtggtaa cttaacaata cagacctaaa aagtctgttt aatgattcaa agtcccacgt   23880
ccttcctaat agtattaatt tttctttggt gtaaacttgt actaagttgt tttagagagt   23940
ttattatagc gctccaacaa ctaatacaag ttttactcca aattatcaat agtaacttac   24000
```

```
agcctagact gaccctttgt cacagtctag actaatgtta aacttagaag caattattga    24060
aactggtgag caagtgattc aaaaaatcag tttcaattta cagcatattt caagtgtatt    24120
aaacacagaa gtatttgacc cctttgacta ttgttattac agaggaggta attttggga     24180 aatagagtca gctgaagatt gttcaggtga tgatgaattt attgaataag tcgctagagg    24240
aaaatggaag ttttctaaca gcgctttata tatttgtagg attttagca ctttatcttc     24300 taggtagagc acttcaagca tttgtacagg ctgctgatgc ttgttgttta ttttggtata    24360
catgggtagt aattccagga gctaagggta cagccttgt atataagtat acatatggta      24420
gaaaacttaa caatccggaa ttagaagcag ttattgtcaa cgagtttcct aagaacggtt    24480
ggaataataa aaatccagca aattttcaag atgtccaacg agacaaattg tactcttgac    24540
tttgaacagt cagttgagct ttttaaagag tataatttat ttataactgc attcttgttg    24600
ttcttaacca taatacttca gtatggctat gcaacaagaa gtaagtttat ttatatactg    24660
aaaatgatag tgttatggtg cttttggccc cttaacattg cagtaggtgt aatttcatgt    24720
atatacccac caaacacagg aggtcttgtc gcagcgataa tacttacagt gtttgcgtgt    24780
ctgtcttttg taggttattg gatccagagt attagactct ttaagcggtg taggtcatgg    24840
tggtcattta acccagaatc taatgccgta ggttcaatac tcctaactaa tggtcaacaa    24900
tgtaattttg ctatagagag tgtgccaatg gtgctttctc caattataaa gaatggtgtt    24960
ctttattgtg agggtcagtg gcttgctaag tgtgaaccag accacttgcc taaagatata    25020
tttgtttgta caccggatag acgtaatatc taccgtatgg tgcagaaata tactggtgac    25080
caaagcggaa ataagaaacg gtttgctacg tttgtctatg caaagcagtc agtagatact    25140
ggcgagctag aaagtgtagc aacaggaggg agtagtcttt acacctaaat gtgtgtgtgt    25200
agagagtatt taaaattatt ctttaatagt gcctctattt taagagcgca taatagtatt    25260
atttttgagg atattaatat aaatcctctc tgttttatac tctcttttca agagctatta    25320
tttaaaaaac agttttttcca ctcttttgtg ccaaaaacta ttgttgttaa tggtgtaacc   25380
tttcaagtag ataatggaaa agtctactac gaaggaaaac caatttttca gaaaggttgt    25440
tgtaggttgt ggttgagtta taaaaaagat taaaactacct actacactta tttttataag   25500
aggcgtttta tcttacaagc gcttaataaa tacggacgat gaaatggctg actagttttg    25560
taagggcagt tatttcatgt tataaacccc tattattaac tcaattaaga gtattagata    25620
ggttaatctt agatcatgga ccaaaacaca tcttaacgtg tgttaggtgc gtgattttgt    25680
ttcaattaga tttagtttat aggttggcgt atacgcctac tcaatcgctg gtatgaataa    25740
tagtaaagat aatccttttt gcggagcaat agcaagaaaa gcgcgaattt atctgagaga    25800
aggattagat tgtgtttact ttcttaacaa agcaggacaa gcagagtctt gtcccgcgtg    25860
tacctctcta gtattccagg ggaaaacttg tgaggaacac aaatataata ataatctttt    25920
gtcatggcaa gcggtaaggc aactggaaag acagatgccc cagctccagt catcaaacta    25980
ggaggaccaa agccacctaa agttggttct tctggaaatg tatcttggtt tcaagcaata    26040
aaagccaaga agttaaattc acctccgcct aagtttgaag gtagcggtgt tcctgataat    26100
gaaaatctaa aaccaagtca gcagcatgga tattgggaga gccaagctag gtttaagcca    26160
ggtaaaggtg gaagaaaacc agtcccagat gcttggtatt tttactatac tggaacagga    26220
ccagccgcta acctgaattg gggtgatagc caagatggta tagtgtgggt tgctggtaag    26280
ggtgctgata ctaaatttag atctaatcag ggtactcgtg actctgacaa gtttgaccaa    26340
tatccgctac ggttttcaga cggaggacct gatggtaatt ccgttggga tttcattcct    26400
```

```
ctgaatcgtg gcaggagtgg gagatcaaca gcagcttcat cagcagcatc tagtagagca    26460
ccatcacgtg aagtttcgcg tggtcgcagg agtggttctg aagatgatct tattgctcgt    26520
gcagcaagga taattcagga tcagcagaag aagggttctc gcattacaaa ggctaaggct    26580
gatgaaatgg ctcaccgccg gtattgcaag cgcactattc cacctaatta taaggttgat    26640
caagtgtttg gtccccgtac taaaggtaag gagggaaatt ttggtgatga caagatgaat    26700
gaggaaggta ttaaggatgg gcgcgttaca gcaatgctca acctagttcc tagcagccat    26760
gcttgtcttt tcggaagtag agtgacgccc agacttcaac cagatgggct gcacttgaaa    26820
tttgaattta ctactgtggt cccacgtgat gatccgcgt ttgataatta tgtaaaaatt    26880
tgtgatcagt gtgttgatgg tgtaggaaca cgtccaaaag atgatgaacc aagaccaaag    26940
tcacgctcaa gttcaagacc tgcaacaaga ggaaattctc cagcgccaag acagcagcgc    27000
cctaagaagg agaaaaagcc aaagaagcag gatgatgaag tggataaagc attgacctca    27060
gatgaggaga ggaacaatgc acagctggaa tttgatgatg aacccaaggt aattaactgg    27120
ggggattcag ccctaggaga gaatgaactt tgagtaaaat tcaatagtaa gagttaagga    27180
agataggcat gtagcttgat tacctacatg tctatcgcca gggaaatgtc taatttgtct    27240
acttagtagc ctggaaacga acggtagacc cttagatttt aatttagttt aattttagt    27300 ttagtttaag ttagtttaga gtaggtataa agatgccagt gccggggcca cgcggagtac    27360
gaccgagggt acagcactag gacgcccatt aggggaagag ctaaatttta gtttaagtta    27420
agtttaattg gctatgtata gttaaaattt ataggctagt atagagttag agcaaaaaaa    27480
aaaaaaaaaa aaaaaaaaa                                                27500

<210> SEQ ID NO 2
<211> LENGTH: 435
<212> TYPE: DNA
<213> ORGANISM: Infectious bronchitis virus

<400> SEQUENCE: 2
tctaaaggtc atgagacaga ggaagtggat gctgtaggca ttctctcact ttgttctttt     60
gcagtagatc ctgcggatac atattgtaaa tatgtggcag caggtaatca accttttaggt   120 aactgtgtta aaatgttgac agtacataat ggtagtggtt ttgcaataac atcaaagcca    180
agtccaactc cggatcagga ttcttatgga ggagcttctg tgtgtcttta ttgtagagca    240
catatagcac accttggcgg agcaggaaat ttagatggac gctgtcaatt taaaggttct    300
tttgtgcaaa tacctactac ggagaaagat cctgttggat tctgtctacg taacaaggtt    360
tgcactgttt gtcagtgttg gattggttat ggatgtcagt gtgattcact tagacaacct    420
aaaccttctg ttcag                                                      435

<210> SEQ ID NO 3
<211> LENGTH: 1563
<212> TYPE: DNA
<213> ORGANISM: Infectious bronchitis virus

<400> SEQUENCE: 3
ggtacaggct tgtttaaaat ttgcaacaaa gagtttagtg gtgttcaccc agcttatgca     60
gtcacaacta aggctcttgc tgcaacttat aaagttaatg atgaacttgc tgcacttgtt    120
aacgtggaag ctggttcaga ataacatat aaacatctta tttctttgtt agggtttaag    180
atgagtgtta atgttgaagg ctgccacaac atgtttataa cacgtgatga ggctatccgc    240
```

-continued

```
aacgtaagag gttgggtagg ttttgatgta gaagcaacac atgcttgcgg tactaacatt    300
ggtactaacc tgcctttcca agtaggtttc tctactggtg cagactttgt agttacgcct    360
gagggacttg tagatacttc aataggcaat aattttgagc ctgtgaattc taaagcacct    420
ccaggtgaac aatttaatca cttgagagcg ttattcaaaa gtgctaaacc ttggcatgtt    480
gtaaggccaa ggattgtgca aatgttagcg gataacctgt gcaacgtttc agattgtgta    540
gtgtttgtca cgtggtgtca tggcctagaa ctaaccactt tgcgctattt tgttaaaata    600
ggcaaggacc aagtttgttc ttgcggttct agagcaacaa cttttaattc tcatactcag    660
gcttatgctt gttggaagca ttgcttgggt tttgattttg tttataatcc actcttagtg    720
gatattcaac agtggggtta ttctggtaac ctacaattta accatgattt gcattgtaat    780
gtgcatggac acgcacatgt agcttctgcg gatgctatta tgacgcgttg tcttgcaatt    840
aataatgcat tttgtcaaga tgtcaactgg gatttaactt accctcatat agcaaatgag    900
gatgaagtca attctagctg tagatattta caacgcatgt atcttaatgc atgtgttgat    960
gctcttaaag ttaacgttgt ctatgatata ggcaacccta aaggtattaa atgtgttaga   1020
cgtggagact taaattttag attctatgat aagaatccaa tagtacccaa tgtcaagcag   1080
tttgagtatg actataatca gcacaaagat aagtttgctg atggtctttg tatgttttgg   1140
aattgtaatg tggattgtta tcccgacaat tccttacttt gtaggtacga cacacgaaat   1200
ttgagtgtgt ttaacctacc tggttgtaat ggtggtagct tgtatgttaa caagcatgca   1260
ttccacacac ctaaatttga tcgcactagc tttcgtaatt tgaaagctat gccattcttt   1320
ttctatgact catcgccttg cgagaccatt caattggatg gagttgcgca agaccttgtg   1380
tcattagcta cgaaagattg tatcacaaaa tgcaacatag gcggtgctgt ttgtaaaaag   1440
cacgcacaaa tgtatgcaga ttttgtgact tcttataatg cagctgttac tgctggtttt   1500
actttttggg ttactaataa ttttaaccca tataatttgt ggaaaagttt ttcagctctc   1560
cag                                                                 1563
```

<210> SEQ ID NO 4
<211> LENGTH: 1014
<212> TYPE: DNA
<213> ORGANISM: Infectious bronchitis virus

<400> SEQUENCE: 4

```
tctatcgaca atattgctta taatatgtat aagggtggtc attatgatgc tattgcagga     60
gaaatgccca ctatcgtaac tggagataaa gtttttgtta tagatcaagg cgtagaaaaa    120
gcagtttttt ttaatcaaac aattctgcct acatctgtag cgtttgagct gtatgcgaag    180
agaaatattc gcacactgcc aaacaaccgt attttgaaag gtttgggtgt agatgtgact    240
aatggatttg taatttggga ttacacgaac caaacaccac tataccgtaa tactgttaag    300
gtatgtgcat atacagacat agaaccaaat ggcctaatag tgctgtatga tgatagatat    360
ggtgattacc agtcttttct agctgctgat aatgctgttt tagtttctac acagtgttac    420
aagcggtatt cgtatgtaga aataccgtca aacctgcttg ttcagaacgg tattccgtta    480
aaagatggag cgaacctgta tgtttataag cgtgttaatg gtgcgtttgt tacgctacct    540
aacacaataa acacacaggg tcgaagttat gaaacttttg aacctcgtag tgatgttgag    600
cgtgattttc tcgacatgtc tgaggagagt tttgtagaaa agtatggtaa agaattaggt    660
ctacagcaca tactgtatgg tgaagttgat aagccccaat taggtggttt ccacactgtt    720
ataggtatgt gcagactttt acgtgcgaat aagttgaacg caaagtctgt tactaattct    780
```

```
gattctgatg tcatgcaaaa ttattttgta ttggcagaca atggttccta caagcaagtg    840
tgtactgttg tggatttgct gcttgatgat ttcttagaac ttcttaggaa catactgaaa    900
gagtatggta ctaataagtc taaagttgta acagtgtcaa ttgattacca tagcataaat    960
tttatgactt ggtttgaaga tggcattatt aaaacatgtt atccacagct tcaa          1014
```

<210> SEQ ID NO 5
<211> LENGTH: 909
<212> TYPE: DNA
<213> ORGANISM: Infectious bronchitis virus

<400> SEQUENCE: 5

```
tcagcatgga cgtgtggtta atatgcct gaactttata aagttcagaa ttgtgttatg       60
gaaccttgca acattcctaa ttatggtgtt ggaatagcgt tgccaagtgg tattatgatg    120
aatgtggcaa agtatacaca actctgtcaa tacctttcga aaacaacaat gtgtgtaccg    180
cataatatgc gagtaatgca ttttggagct ggaagtgaca aggagtggt gccaggtagt     240 actgttctta acaatggct cccagaaggg acactccttg tcgataatga tattgtagac     300
tatgtgtctg atgcacatgt ttctgtgctt tcagattgca ataaatataa gacagagcac    360
aagtttgatc ttgtgatatc tgatatgtat acagacaatg attcaaaaag aaagcatgaa    420
ggcgtgatag ccaataatgg caatgatgac gttttcatat atctctcaag ttttcttcgt    480
aataatttgg ctctaggtgg tagttttgct gtaaaagtga cagagacaag ttggcacgaa    540
gttttatatg acattgcaca ggattgtgca tggtggacaa tgttttgtac agcagtgaat    600
gcctcttctt cagaagcatt cttgattggt gttaattatt gggtgcaag tgaaaaggtt     660 aaggttagtg gaaaaacgct gcacgcaaat tatatatttt ggaggaattg taattattta    720
caaacctctg cttatagtat atttgacgtt gctaagtttg atttgagatt gaaagcaacg    780
ccagttgtta atttgaaaac tgaacaaaag acagacttag tctttaattt aattaagtgt    840
ggtaagttac tggtaagaga tgttggtaac acctctttta ctagtgactc ttttgtgtgt    900
actatgtag                                                            909
```

<210> SEQ ID NO 6
<211> LENGTH: 145
<212> TYPE: PRT
<213> ORGANISM: Infectious bronchitis virus

<400> SEQUENCE: 6

```
Ser Lys Gly His Glu Thr Glu Glu Val Asp Ala Val Gly Ile Leu Ser
 1               5                  10                  15

Leu Cys Ser Phe Ala Val Asp Pro Ala Asp Thr Tyr Cys Lys Tyr Val
                20                  25                  30

Ala Ala Gly Asn Gln Pro Leu Gly Asn Cys Val Lys Met Leu Thr Val
            35                  40                  45

His Asn Gly Ser Gly Phe Ala Ile Thr Ser Lys Pro Ser Pro Thr Pro
        50                  55                  60

Asp Gln Asp Ser Tyr Gly Gly Ala Ser Val Cys Leu Tyr Cys Arg Ala
65                  70                  75                  80

His Ile Ala His Pro Gly Gly Ala Gly Asn Leu Asp Gly Arg Cys Gln
                85                  90                  95

Phe Lys Gly Ser Phe Val Gln Ile Pro Thr Thr Glu Lys Asp Pro Val
            100                 105                 110

Gly Phe Cys Leu Arg Asn Lys Val Cys Thr Val Cys Gln Cys Trp Ile
```

```
            115                 120                 125
Gly Tyr Gly Cys Gln Cys Asp Ser Leu Arg Gln Pro Lys Pro Ser Val
    130                 135                 140

Gln
145

<210> SEQ ID NO 7
<211> LENGTH: 521
<212> TYPE: PRT
<213> ORGANISM: Infectious bronchitis virus

<400> SEQUENCE: 7

Gly Thr Gly Leu Phe Lys Ile Cys Asn Lys Glu Phe Ser Gly Val His
1               5                   10                  15

Pro Ala Tyr Ala Val Thr Thr Lys Ala Leu Ala Thr Tyr Lys Val
            20                  25                  30

Asn Asp Glu Leu Ala Ala Leu Val Asn Val Glu Ala Gly Ser Glu Ile
        35                  40                  45

Thr Tyr Lys His Leu Ile Ser Leu Leu Gly Phe Lys Met Ser Val Asn
    50                  55                  60

Val Glu Gly Cys His Asn Met Phe Ile Thr Arg Asp Glu Ala Ile Arg
65                  70                  75                  80

Asn Val Arg Gly Trp Val Gly Phe Asp Val Glu Ala Thr His Ala Cys
                85                  90                  95

Gly Thr Asn Ile Gly Thr Asn Leu Pro Phe Gln Val Gly Phe Ser Thr
            100                 105                 110

Gly Ala Asp Phe Val Val Thr Pro Glu Gly Leu Val Asp Thr Ser Ile
        115                 120                 125

Gly Asn Asn Phe Glu Pro Val Asn Ser Lys Ala Pro Pro Gly Glu Gln
    130                 135                 140

Phe Asn His Leu Arg Ala Leu Phe Lys Ser Ala Lys Pro Trp His Val
145                 150                 155                 160

Val Arg Pro Arg Ile Val Gln Met Leu Ala Asp Asn Leu Cys Asn Val
                165                 170                 175

Ser Asp Cys Val Val Phe Val Thr Trp Cys His Gly Leu Glu Leu Thr
            180                 185                 190

Thr Leu Arg Tyr Phe Val Lys Ile Gly Lys Asp Gln Val Cys Ser Cys
        195                 200                 205

Gly Ser Arg Ala Thr Thr Phe Asn Ser His Thr Gln Ala Tyr Ala Cys
    210                 215                 220

Trp Lys His Cys Leu Gly Phe Asp Phe Val Tyr Asn Pro Leu Leu Val
225                 230                 235                 240

Asp Ile Gln Gln Trp Gly Tyr Ser Gly Asn Leu Gln Phe Asn His Asp
                245                 250                 255

Leu His Cys Asn Val His Gly His Ala His Val Ala Ser Ala Asp Ala
            260                 265                 270

Ile Met Thr Arg Cys Leu Ala Ile Asn Asn Ala Phe Cys Gln Asp Val
        275                 280                 285

Asn Trp Asp Leu Thr Tyr Pro His Ile Ala Asn Glu Asp Glu Val Asn
    290                 295                 300

Ser Ser Cys Arg Tyr Leu Gln Arg Met Tyr Leu Asn Ala Cys Val Asp
305                 310                 315                 320

Ala Leu Lys Val Asn Val Val Tyr Asp Ile Gly Asn Pro Lys Gly Ile
                325                 330                 335
```

Lys Cys Val Arg Arg Gly Asp Leu Asn Phe Arg Phe Tyr Asp Lys Asn
                340                 345                 350

Pro Ile Val Pro Asn Val Lys Gln Phe Glu Tyr Asp Tyr Asn Gln His
            355                 360                 365

Lys Asp Lys Phe Ala Asp Gly Leu Cys Met Phe Trp Asn Cys Asn Val
        370                 375                 380

Asp Cys Tyr Pro Asp Asn Ser Leu Val Cys Arg Tyr Asp Thr Arg Asn
385                 390                 395                 400

Leu Ser Val Phe Asn Leu Pro Gly Cys Asn Gly Gly Ser Leu Tyr Val
                405                 410                 415

Asn Lys His Ala Phe His Thr Pro Lys Phe Asp Arg Thr Ser Phe Arg
            420                 425                 430

Asn Leu Lys Ala Met Pro Phe Phe Tyr Asp Ser Ser Pro Cys Glu
        435                 440                 445

Thr Ile Gln Leu Asp Gly Val Ala Gln Asp Leu Val Ser Leu Ala Thr
    450                 455                 460

Lys Asp Cys Ile Thr Lys Cys Asn Ile Gly Gly Ala Val Cys Lys Lys
465                 470                 475                 480

His Ala Gln Met Tyr Ala Asp Phe Val Thr Ser Tyr Asn Ala Ala Val
                485                 490                 495

Thr Ala Gly Phe Thr Phe Trp Val Thr Asn Asn Phe Asn Pro Tyr Asn
            500                 505                 510

Leu Trp Lys Ser Phe Ser Ala Leu Gln
        515                 520

<210> SEQ ID NO 8
<211> LENGTH: 338
<212> TYPE: PRT
<213> ORGANISM: Infectious bronchitis virus

<400> SEQUENCE: 8

Ser Ile Asp Asn Ile Ala Tyr Asn Met Tyr Lys Gly Gly His Tyr Asp
1               5                   10                  15

Ala Ile Ala Gly Glu Met Pro Thr Ile Val Thr Gly Asp Lys Val Phe
            20                  25                  30

Val Ile Asp Gln Gly Val Glu Lys Ala Val Phe Phe Asn Gln Thr Ile
        35                  40                  45

Leu Pro Thr Ser Val Ala Phe Glu Leu Tyr Ala Lys Arg Asn Ile Arg
    50                  55                  60

Thr Leu Pro Asn Asn Arg Ile Leu Lys Gly Leu Gly Val Asp Val Thr
65                  70                  75                  80

Asn Gly Phe Val Ile Trp Asp Tyr Thr Asn Gln Thr Pro Leu Tyr Arg
                85                  90                  95

Asn Thr Val Lys Val Cys Ala Tyr Thr Asp Ile Glu Pro Asn Gly Leu
            100                 105                 110

Ile Val Leu Tyr Asp Asp Arg Tyr Gly Asp Tyr Gln Ser Phe Leu Ala
        115                 120                 125

Ala Asp Asn Ala Val Leu Val Ser Thr Gln Cys Tyr Lys Arg Tyr Ser
    130                 135                 140

Tyr Val Glu Ile Pro Ser Asn Leu Leu Val Gln Asn Gly Ile Pro Leu
145                 150                 155                 160

Lys Asp Gly Ala Asn Leu Tyr Val Tyr Lys Arg Val Asn Gly Ala Phe
                165                 170                 175

Val Thr Leu Pro Asn Thr Leu Asn Thr Gln Gly Arg Ser Tyr Glu Thr
            180                 185                 190

```
Phe Glu Pro Arg Ser Asp Val Glu Arg Asp Phe Leu Asp Met Ser Glu
            195                 200                 205

Glu Ser Phe Val Glu Lys Tyr Gly Lys Glu Leu Gly Leu Gln His Ile
        210                 215                 220

Leu Tyr Gly Glu Val Asp Lys Pro Gln Leu Gly Gly Leu His Thr Val
225                 230                 235                 240

Ile Gly Met Cys Arg Leu Leu Arg Ala Asn Lys Leu Asn Ala Lys Ser
                245                 250                 255

Val Thr Asn Ser Asp Ser Asp Val Met Gln Asn Tyr Phe Val Leu Ala
            260                 265                 270

Asp Asn Gly Ser Tyr Lys Gln Val Cys Thr Val Asp Leu Leu
            275                 280                 285

Asp Asp Phe Leu Glu Leu Leu Arg Asn Ile Leu Lys Glu Tyr Gly Thr
        290                 295                 300

Asn Lys Ser Lys Val Val Thr Val Ser Ile Asp Tyr His Ser Ile Asn
305                 310                 315                 320

Phe Met Thr Trp Phe Glu Asp Gly Ile Ile Lys Thr Cys Tyr Pro Gln
                325                 330                 335

Leu Gln

<210> SEQ ID NO 9
<211> LENGTH: 302
<212> TYPE: PRT
<213> ORGANISM: Infectious bronchitis virus

<400> SEQUENCE: 9

Ser Ala Trp Thr Cys Gly Tyr Asn Met Pro Glu Leu Tyr Lys Val Gln
1               5                   10                  15

Asn Cys Val Met Glu Pro Cys Asn Ile Pro Asn Tyr Gly Val Gly Ile
            20                  25                  30

Ala Leu Pro Ser Gly Ile Met Met Asn Val Ala Lys Tyr Thr Gln Leu
        35                  40                  45

Cys Gln Tyr Leu Ser Lys Thr Thr Met Cys Val Pro His Asn Met Arg
    50                  55                  60

Val Met His Phe Gly Ala Gly Ser Asp Lys Gly Val Ala Pro Gly Ser
65                  70                  75                  80

Thr Val Leu Lys Gln Trp Leu Pro Glu Gly Thr Leu Leu Val Asp Asn
                85                  90                  95

Asp Ile Val Asp Tyr Val Ser Asp Ala His Val Ser Val Leu Ser Asp
            100                 105                 110

Cys Asn Lys Tyr Lys Thr Glu His Lys Phe Asp Leu Val Ile Ser Asp
        115                 120                 125

Met Tyr Thr Asp Asn Asp Ser Lys Arg Lys His Glu Gly Val Ile Ala
    130                 135                 140

Asn Asn Gly Asn Asp Asp Val Phe Ile Tyr Leu Ser Ser Phe Leu Arg
145                 150                 155                 160

Asn Asn Leu Ala Leu Gly Gly Ser Phe Ala Val Lys Val Thr Glu Thr
                165                 170                 175

Ser Trp His Glu Val Leu Tyr Asp Ile Ala Gln Asp Cys Ala Trp Trp
            180                 185                 190

Thr Met Phe Cys Thr Ala Val Asn Ala Ser Ser Glu Ala Phe Leu
        195                 200                 205

Val Gly Val Asn Tyr Leu Gly Ala Ser Glu Lys Val Lys Val Ser Gly
    210                 215                 220
```

```
Lys Thr Leu His Ala Asn Tyr Ile Phe Trp Arg Asn Cys Asn Tyr Leu
225                 230                 235                 240

Gln Thr Ser Ala Tyr Ser Ile Phe Asp Val Ala Lys Phe Asp Leu Arg
            245                 250                 255

Leu Lys Ala Thr Pro Val Val Asn Leu Lys Thr Glu Gln Lys Thr Asp
        260                 265                 270

Leu Val Phe Asn Leu Ile Lys Cys Gly Lys Leu Leu Val Arg Asp Val
    275                 280                 285

Gly Asn Thr Ser Phe Thr Ser Asp Ser Phe Val Cys Thr Met
290                 295                 300

<210> SEQ ID NO 10
<211> LENGTH: 145
<212> TYPE: PRT
<213> ORGANISM: Artificial Sequence
<220> FEATURE:
<223> OTHER INFORMATION: Mutated Nsp10 sequence

<400> SEQUENCE: 10

Ser Lys Gly His Glu Thr Glu Glu Val Asp Ala Val Gly Ile Leu Ser
1               5                   10                  15

Leu Cys Ser Phe Ala Val Asp Pro Ala Asp Thr Tyr Cys Lys Tyr Val
            20                  25                  30

Ala Ala Gly Asn Gln Pro Leu Gly Asn Cys Val Lys Met Leu Thr Val
        35                  40                  45

His Asn Gly Ser Gly Phe Ala Ile Thr Ser Lys Pro Ser Pro Thr Pro
    50                  55                  60

Asp Gln Asp Ser Tyr Gly Gly Ala Ser Val Cys Leu Tyr Cys Arg Ala
65                  70                  75                  80

His Ile Ala His Leu Gly Gly Ala Gly Asn Leu Asp Gly Arg Cys Gln
                85                  90                  95

Phe Lys Gly Ser Phe Val Gln Ile Pro Thr Thr Glu Lys Asp Pro Val
            100                 105                 110

Gly Phe Cys Leu Arg Asn Lys Val Cys Thr Val Cys Gln Cys Trp Ile
        115                 120                 125

Gly Tyr Gly Cys Gln Cys Asp Ser Leu Arg Gln Pro Lys Pro Ser Val
    130                 135                 140

Gln
145

<210> SEQ ID NO 11
<211> LENGTH: 521
<212> TYPE: PRT
<213> ORGANISM: Artificial Sequence
<220> FEATURE:
<223> OTHER INFORMATION: Mutated Nsp14 sequence

<400> SEQUENCE: 11

Gly Thr Gly Leu Phe Lys Ile Cys Asn Lys Glu Phe Ser Gly Val His
1               5                   10                  15

Pro Ala Tyr Ala Val Thr Thr Lys Ala Leu Ala Ala Thr Tyr Lys Val
            20                  25                  30

Asn Asp Glu Leu Ala Ala Leu Val Asn Val Glu Ala Gly Ser Glu Ile
        35                  40                  45

Thr Tyr Lys His Leu Ile Ser Leu Leu Gly Phe Lys Met Ser Val Asn
    50                  55                  60

Val Glu Gly Cys His Asn Met Phe Ile Thr Arg Asp Glu Ala Ile Arg
```

```
                65                  70                  75                  80
Asn Val Arg Gly Trp Val Gly Phe Asp Val Glu Ala Thr His Ala Cys
                    85                  90                  95

Gly Thr Asn Ile Gly Thr Asn Leu Pro Phe Gln Val Gly Phe Ser Thr
                100                 105                 110

Gly Ala Asp Phe Val Val Thr Pro Glu Gly Leu Val Asp Thr Ser Ile
                115                 120                 125

Gly Asn Asn Phe Glu Pro Val Asn Ser Lys Ala Pro Pro Gly Glu Gln
            130                 135                 140

Phe Asn His Leu Arg Ala Leu Phe Lys Ser Ala Lys Pro Trp His Val
145                 150                 155                 160

Val Arg Pro Arg Ile Val Gln Met Leu Ala Asp Asn Leu Cys Asn Val
                    165                 170                 175

Ser Asp Cys Val Val Phe Val Thr Trp Cys His Gly Leu Glu Leu Thr
                180                 185                 190

Thr Leu Arg Tyr Phe Val Lys Ile Gly Lys Asp Gln Val Cys Ser Cys
                195                 200                 205

Gly Ser Arg Ala Thr Thr Phe Asn Ser His Thr Gln Ala Tyr Ala Cys
                210                 215                 220

Trp Lys His Cys Leu Gly Phe Asp Phe Val Tyr Asn Pro Leu Leu Val
225                 230                 235                 240

Asp Ile Gln Gln Trp Gly Tyr Ser Gly Asn Leu Gln Phe Asn His Asp
                    245                 250                 255

Leu His Cys Asn Val His Gly His Ala His Val Ala Ser Ala Asp Ala
                260                 265                 270

Ile Met Thr Arg Cys Leu Ala Ile Asn Asn Ala Phe Cys Gln Asp Val
                275                 280                 285

Asn Trp Asp Leu Thr Tyr Pro His Ile Ala Asn Glu Asp Glu Val Asn
                290                 295                 300

Ser Ser Cys Arg Tyr Leu Gln Arg Met Tyr Leu Asn Ala Cys Val Asp
305                 310                 315                 320

Ala Leu Lys Val Asn Val Val Tyr Asp Ile Gly Asn Pro Lys Gly Ile
                    325                 330                 335

Lys Cys Val Arg Arg Gly Asp Leu Asn Phe Arg Phe Tyr Asp Lys Asn
                340                 345                 350

Pro Ile Val Pro Asn Val Lys Gln Phe Glu Tyr Asp Tyr Asn Gln His
                355                 360                 365

Lys Asp Lys Phe Ala Asp Gly Leu Cys Met Phe Trp Asn Cys Asn Val
                370                 375                 380

Asp Cys Tyr Pro Asp Asn Ser Leu Leu Cys Arg Tyr Asp Thr Arg Asn
385                 390                 395                 400

Leu Ser Val Phe Asn Leu Pro Gly Cys Asn Gly Gly Ser Leu Tyr Val
                    405                 410                 415

Asn Lys His Ala Phe His Thr Pro Lys Phe Asp Arg Thr Ser Phe Arg
                420                 425                 430

Asn Leu Lys Ala Met Pro Phe Phe Tyr Asp Ser Ser Pro Cys Glu
                435                 440                 445

Thr Ile Gln Leu Asp Gly Val Ala Gln Asp Leu Val Ser Leu Ala Thr
                450                 455                 460

Lys Asp Cys Ile Thr Lys Cys Asn Ile Gly Gly Ala Val Cys Lys Lys
465                 470                 475                 480

His Ala Gln Met Tyr Ala Asp Phe Val Thr Ser Tyr Asn Ala Ala Val
                    485                 490                 495
```

```
Thr Ala Gly Phe Thr Phe Trp Val Thr Asn Asn Phe Asn Pro Tyr Asn
                500                 505                 510

Leu Trp Lys Ser Phe Ser Ala Leu Gln
        515                 520

<210> SEQ ID NO 12
<211> LENGTH: 338
<212> TYPE: PRT
<213> ORGANISM: Artificial Sequence
<220> FEATURE:
<223> OTHER INFORMATION: Mutated Nsp15 sequence

<400> SEQUENCE: 12

Ser Ile Asp Asn Ile Ala Tyr Asn Met Tyr Lys Gly Gly His Tyr Asp
1               5                   10                  15

Ala Ile Ala Gly Glu Met Pro Thr Ile Val Thr Gly Asp Lys Val Phe
            20                  25                  30

Val Ile Asp Gln Gly Val Glu Lys Ala Val Phe Phe Asn Gln Thr Ile
        35                  40                  45

Leu Pro Thr Ser Val Ala Phe Glu Leu Tyr Ala Lys Arg Asn Ile Arg
    50                  55                  60

Thr Leu Pro Asn Asn Arg Ile Leu Lys Gly Leu Gly Val Asp Val Thr
65                  70                  75                  80

Asn Gly Phe Val Ile Trp Asp Tyr Thr Asn Gln Thr Pro Leu Tyr Arg
                85                  90                  95

Asn Thr Val Lys Val Cys Ala Tyr Thr Asp Ile Glu Pro Asn Gly Leu
            100                 105                 110

Ile Val Leu Tyr Asp Asp Arg Tyr Gly Asp Tyr Gln Ser Phe Leu Ala
        115                 120                 125

Ala Asp Asn Ala Val Leu Val Ser Thr Gln Cys Tyr Lys Arg Tyr Ser
    130                 135                 140

Tyr Val Glu Ile Pro Ser Asn Leu Leu Val Gln Asn Gly Ile Pro Leu
145                 150                 155                 160

Lys Asp Gly Ala Asn Leu Tyr Val Tyr Lys Arg Val Asn Gly Ala Phe
                165                 170                 175

Val Thr Leu Pro Asn Thr Ile Asn Thr Gln Gly Arg Ser Tyr Glu Thr
            180                 185                 190

Phe Glu Pro Arg Ser Asp Val Glu Arg Asp Phe Leu Asp Met Ser Glu
        195                 200                 205

Glu Ser Phe Val Glu Lys Tyr Gly Lys Glu Leu Gly Leu Gln His Ile
    210                 215                 220

Leu Tyr Gly Glu Val Asp Lys Pro Gln Leu Gly Gly Leu His Thr Val
225                 230                 235                 240

Ile Gly Met Cys Arg Leu Leu Arg Ala Asn Lys Leu Asn Ala Lys Ser
                245                 250                 255

Val Thr Asn Ser Asp Ser Asp Val Met Gln Asn Tyr Phe Val Leu Ala
            260                 265                 270

Asp Asn Gly Ser Tyr Lys Gln Val Cys Thr Val Val Asp Leu Leu Leu
        275                 280                 285

Asp Asp Phe Leu Glu Leu Leu Arg Asn Ile Leu Lys Glu Tyr Gly Thr
    290                 295                 300

Asn Lys Ser Lys Val Val Thr Val Ser Ile Asp Tyr His Ser Ile Asn
305                 310                 315                 320

Phe Met Thr Trp Phe Glu Asp Gly Ile Ile Lys Thr Cys Tyr Pro Gln
                325                 330                 335
```

Leu Gln

```
<210> SEQ ID NO 13
<211> LENGTH: 302
<212> TYPE: PRT
<213> ORGANISM: Artificial Sequence
<220> FEATURE:
<223> OTHER INFORMATION: Mutated Nsp16 sequence

<400> SEQUENCE: 13

Ser Ala Trp Thr Cys Gly Tyr Asn Met Pro Glu Leu Tyr Lys Val Gln
1               5                   10                  15

Asn Cys Val Met Glu Pro Cys Asn Ile Pro Asn Tyr Gly Val Gly Ile
            20                  25                  30

Ala Leu Pro Ser Gly Ile Met Met Asn Val Ala Lys Tyr Thr Gln Leu
        35                  40                  45

Cys Gln Tyr Leu Ser Lys Thr Thr Met Cys Val Pro His Asn Met Arg
    50                  55                  60

Val Met His Phe Gly Ala Gly Ser Asp Lys Gly Val Ala Pro Gly Ser
65                  70                  75                  80

Thr Val Leu Lys Gln Trp Leu Pro Glu Gly Thr Leu Leu Val Asp Asn
                85                  90                  95

Asp Ile Val Asp Tyr Val Ser Asp Ala His Val Ser Val Leu Ser Asp
            100                 105                 110

Cys Asn Lys Tyr Lys Thr Glu His Lys Phe Asp Leu Val Ile Ser Asp
        115                 120                 125

Met Tyr Thr Asp Asn Asp Ser Lys Arg Lys His Glu Gly Val Ile Ala
130                 135                 140

Asn Asn Gly Asn Asp Asp Val Phe Ile Tyr Leu Ser Ser Phe Leu Arg
145                 150                 155                 160

Asn Asn Leu Ala Leu Gly Gly Ser Phe Ala Val Lys Val Thr Glu Thr
                165                 170                 175

Ser Trp His Glu Val Leu Tyr Asp Ile Ala Gln Asp Cys Ala Trp Trp
            180                 185                 190

Thr Met Phe Cys Thr Ala Val Asn Ala Ser Ser Ser Glu Ala Phe Leu
        195                 200                 205

Ile Gly Val Asn Tyr Leu Gly Ala Ser Glu Lys Val Lys Val Ser Gly
    210                 215                 220

Lys Thr Leu His Ala Asn Tyr Ile Phe Trp Arg Asn Cys Asn Tyr Leu
225                 230                 235                 240

Gln Thr Ser Ala Tyr Ser Ile Phe Asp Val Ala Lys Phe Asp Leu Arg
                245                 250                 255

Leu Lys Ala Thr Pro Val Val Asn Leu Lys Thr Glu Gln Lys Thr Asp
            260                 265                 270

Leu Val Phe Asn Leu Ile Lys Cys Gly Lys Leu Leu Val Arg Asp Val
        275                 280                 285

Gly Asn Thr Ser Phe Thr Ser Asp Ser Phe Val Cys Thr Met
    290                 295                 300
```